United States Patent
Kao et al.

(10) Patent No.: US 12,371,473 B2
(45) Date of Patent: *Jul. 29, 2025

(54) THERAPEUTIC BIOLOGIC FOR TREATMENT OF HEPATOCELLULAR CARCINOMA

(71) Applicant: Circular Commitment Company, Taipei (TW)

(72) Inventors: Kuo-Jang Kao, Gainesville, FL (US); Yun-Hsin Wang, Taipei (TW)

(73) Assignee: Circular Commitment Company, Taipei (TW)

( * ) Notice: Subject to any disclaimer, the term of this patent is extended or adjusted under 35 U.S.C. 154(b) by 336 days.

This patent is subject to a terminal disclaimer.

(21) Appl. No.: 17/813,857

(22) Filed: Jul. 20, 2022

(65) Prior Publication Data

US 2022/0372109 A1    Nov. 24, 2022

Related U.S. Application Data

(62) Division of application No. 16/513,148, filed on Jul. 16, 2019, now Pat. No. 11,485,771, which is a division of application No. 15/270,430, filed on Sep. 20, 2016, now Pat. No. 10,400,026, which is a division of application No. 14/539,577, filed on Nov. 12, 2014, now Pat. No. 9,493,552.

(60) Provisional application No. 61/904,951, filed on Nov. 15, 2013.

(51) Int. Cl.
| | | |
|---|---|---|
| *A61K 47/64* | (2017.01) | |
| *A61K 47/65* | (2017.01) | |
| *A61K 47/68* | (2017.01) | |
| *C07K 14/745* | (2006.01) | |
| *C07K 16/30* | (2006.01) | |
| *A61K 39/00* | (2006.01) | |
| *C07K 16/28* | (2006.01) | |

(52) U.S. Cl.
CPC ............ *C07K 14/745* (2013.01); *A61K 47/65* (2017.08); *A61K 47/6811* (2017.08); *A61K 47/6849* (2017.08); *A61K 47/6851* (2017.08); *C07K 16/30* (2013.01); *A61K 2039/505* (2013.01); *C07K 16/28* (2013.01); *C07K 2317/24* (2013.01); *C07K 2317/34* (2013.01); *C07K 2317/55* (2013.01); *C07K 2317/565* (2013.01); *C07K 2317/92* (2013.01); *C07K 2319/035* (2013.01); *C07K 2319/33* (2013.01)

(58) Field of Classification Search
CPC ..... A61K 47/64; A61K 47/68; A61K 47/6835
USPC .......................................... 424/178.1, 180.1
See application file for complete search history.

(56) References Cited

U.S. PATENT DOCUMENTS

| | | | |
|---|---|---|---|
| 6,875,570 B2 | 4/2005 | Gerlach et al. | |
| 8,815,240 B2* | 8/2014 | Kao ................. | G01N 33/57438 530/389.1 |
| 8,821,880 B2* | 9/2014 | Kao ....................... | A61K 45/06 436/64 |
| 9,394,359 B2* | 7/2016 | Kao ....................... | A61P 35/00 |
| 9,493,522 B2 | 11/2016 | Wells et al. | |
| 9,493,552 B2 | 11/2016 | Kao et al. | |
| 9,545,443 B2* | 1/2017 | Kao ................. | A61K 51/1018 |
| 10,370,445 B2* | 8/2019 | Kao ....................... | A61P 43/00 |
| 10,400,026 B2 | 9/2019 | Kao et al. | |
| 10,906,959 B2 | 2/2021 | Kao et al. | |
| 11,339,217 B2* | 5/2022 | Kao ................. | A61K 39/39558 |
| 2003/0232753 A1 | 12/2003 | Thorpe et al. | |
| 2008/0233117 A1 | 9/2008 | Roberts et al. | |
| 2009/0169638 A1 | 7/2009 | Davis et al. | |
| 2011/0085973 A1 | 4/2011 | Kao et al. | |
| 2011/0159498 A1 | 6/2011 | Kao et al. | |
| 2011/0262349 A1 | 10/2011 | Kao et al. | |
| 2012/0178908 A1 | 7/2012 | Hilden et al. | |
| 2014/0322131 A1 | 10/2014 | Kao et al. | |
| 2015/0017171 A1 | 1/2015 | Kao et al. | |
| 2015/0140021 A1 | 5/2015 | Kao et al. | |
| 2017/0000898 A1 | 1/2017 | Kao et al. | |
| 2017/0145092 A1 | 5/2017 | Kao | |
| 2018/0362614 A1 | 12/2018 | Kao et al. | |
| 2019/0309062 A1 | 10/2019 | Kao et al. | |
| 2019/0338016 A1 | 11/2019 | Kao et al. | |

FOREIGN PATENT DOCUMENTS

| | | |
|---|---|---|
| CN | 1251532 A | 4/2000 |
| JP | 2013-503140 A | 1/2013 |
| TW | 200714294 A | 4/2007 |
| WO | WO 1996/001653 | 1/1996 |
| WO | WO 1998/031394 A2 | 7/1998 |

(Continued)

OTHER PUBLICATIONS

Almagro & Franssen, Frontiers in Bioscience, 13:1619-33 (2008).*

(Continued)

*Primary Examiner* — Lynn A Bristol
(74) *Attorney, Agent, or Firm* — Hamilton, Brook, Smith & Reynolds, P.C.

(57) ABSTRACT

The invention provides conjugates comprising a coagulating agent conjugated to an antibody, where the antibody specifically binds an extracellular domain epitope of a mammalian PLVAP protein. These agents specifically target HCC tumors and treat the HCC. The invention also provides methods of using these conjugates, such as methods of treating HCC by administering the conjugates provided by the invention or compositions provided by the invention, such as pharmaceutical compositions.

19 Claims, 26 Drawing Sheets
(12 of 26 Drawing Sheet(s) Filed in Color)
Specification includes a Sequence Listing.

(56) References Cited

FOREIGN PATENT DOCUMENTS

| WO | WO 2003/010336 A2 | 2/2003 |
|---|---|---|
| WO | WO 2003/023008 A2 | 3/2003 |
| WO | WO 2003/024392 A2 | 3/2003 |
| WO | WO 2006/105361 A2 | 10/2006 |
| WO | WO 2006/110593 A2 | 10/2006 |
| WO | WO 2008/091781 A1 | 7/2008 |
| WO | WO 2009/117096 A1 | 9/2009 |
| WO | WO 2009/126271 A1 | 10/2009 |
| WO | WO 2010/051105 A1 | 5/2010 |
| WO | WO 2011/023785 A1 | 3/2011 |

OTHER PUBLICATIONS

Edwards et al., J Mol Biol 334:103-118 (2003).*
Marchalonis et al., Dev & Comp Immunol. 30:223-247 (2006).*
Lippow et al., Nature Biotechnology, 25(10):1171-1176 (2007).*
Sulea et al., Scientific Reports, 8(260):1-11 (2018).*
Hasegawa et al., MABS, vol. 9, No. 5, pp. 854-873 (2017).*
Altshuler et al., Biochemistry (Moscow), 75(13):1584-1605 (2010).*
Vajda et al., Current Opinion in Structural Biology, 67 pp. 226-231 (2021).*
Marks et al., J. Biol. Chem. 295(29) 9823-9837 (2020).*
Akbar et al., Cell Reports 34, 108856, Mar. 16, 2021.*
Lo et al., BMC Genomics vol. 22, Article No. 116 (2021).*
ThermoFisher product data sheet (High Five™ Cells in Express Five™ Medium; pp. 1-6 (Dec. 31, 2024)).*
U.S. Appl. No. 19/014,483, Kao; Kuo-Jang.*
"*Homo sapiens* plasmalemma vesicle associated protein (PLVAP), mRNA." GenBank [online] [retreived on Nov. 26, 2011]. Retreived from the Internet URL: http://www.ncbi.nlm.nih.gov/nuccore/13775237?sat-OLD06&satkey=7209055.
"Survival Rates for Liver Cancer", 2 pages. URL: http://www/cancer.org/camcer/livercancer/detailedguide/liver-cancer-survival-rates, downloaded from American Cancer Society website on Aug. 25, 2015.
URL: http://www/cancer.org/camcer/livercancer/detailedguide/liver-cancer-survival-rates, downloaded from American Cancer Society website on Aug. 25, 2015.
Bergers, G., and Coussens, L. M., "Extrinsic regulators of epithelial tumor progression: metalloproteinases," Current Opinion in Genetics & Development, 10: 120-127 (2000).
Bernard, A., et al., "A Unique Epitope on the CD2 Molecule Defined by the Monoclonal Antibody 9-1: Epitope-Specific Modulation of the E-Rosette Receptor and Effects on T-Cell Functions," Human Immunology, 17: 388-405 (1986).
Brorson K., et al., "Mutational Analysis of Avidity and Fine Specificity of Anti-Levan Antibodies", J. Immunol. 163; 6694-6701 (1999).
Bruix, J. and Sherman, M., "Management of Hepatocellular Carcinoma: An Update", Hepatology, 53(3): 1020-1022 (2011).
Brummell et al., "Probing the combining site of an anti-carbohydrate antibody by saturation-mutagensis: role of the heavy chain DCR3 residues", Biochemistry 32; 1180-1187 (1993).
Burks et al., "In vitro scanning saturation mutagenesis of an antibody binding pocket", PNAS 94; 412-417 (1997).
Caldas, C., et al., "Humanization of the anti-CD18 antibody 6.7: an unexpected effect of a framework residue in binding to antigen," Molecular Immunology, 39: 941-952 (2003).
Carson-Walter, E. B., et al., "Plasmalemmal Vesicle Associated Protein-1 Is a Novel Marker Implicated in Brain Tumor Angiogenesis," Clin. Cancer Res., 11(21): 7643-7650 (2005).
Casset, F., et al., "A peptide mimetic of an anti-CD4 monoclonal antibody by rational design," Biochemical and Biophysical Research Communications, 307: 198-205 (2003).
Chen, X. et al., "Fusion Protein Linkers: Property, Design and Functionality," Adv. Drug Deliv. Rev, vol. 65; No. 10; 1357-1369 (2013).

Chien, N. C., et al., "Significant structural and functional change of an antigen-binding site by a distant amino acid substitution: Proposal of a structural mechanism," Proc. Natl. Acad. Sci. USA, 86: 5532-5536 (1989).
Colman, "A Structural View of Immune Recognition by antibodies", Research in Immunol. 145; 33-36 (1994).
De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol., 169: 3076-3084 (2002).
Dennis, C., "Off by a whisker," Nature, 442: 739-741 (2006).
Developmental Studies Hybridoma Bank (search for MECA-32 antibody; pp. 1-12; Jul. 31, 2018).
Din HM et al., Relationship between tissue factor expression and angiogenesis of hepatocellular carcinoma and its clinical significance. J. Hepatopancreatobiliary Surgery, Sep. 2008, vol. 20, No. 5, pp. 331-335.
Frankel A.E. et al., Characterization of diphtheria fusion proteins targeted to the human interleukin-3 receptor, Protein engineering, 2000, V. 13, N. 8, p. 575-581, abstract, p. 579-580.
Giusti, A. M., et al., "Somatic diversification of S107 from an antiphosphocholine to an anti-DNA autoantibody is due to a single base change in its heavy chain variable region," Proc. Natl. Acad. Sci. USA, 84: 2926-2930 (1987).
Gotoh, K., et al., "Apg-2 has a chaperone-like activity similar to Hsp110 and is overexpressed in hepatocellular carcinomas," FEBS Letters, 560: 19-24 (2004).
Gray, D., et al., "Maternal Embryonic Leucine Zipper Kinase/Murine Protein Serine-Threonine Kinase 38 Is a Promising Therapeutic Target for Multiple Cancers," Cancer Res., 65(21): 9751-9761 (2005).
Gura, T., "Systems for Identifying New Drugs Are Often Faulty," Science, 278: 1041-1042 (1997).
Güssow, D., and Seemann, G., "Humanization of Monoclonal Antibodies," Methods in Enzymology, 203: 99-121 (1991).
Hayward, D. G., et al., "The Centrosomal Kinase Nek2 Displays Elevated Levels of Protein Expression in Human Breast Cancer," Cancer Research, 64: 7370-7376 (2004).
Hegmans, J. P. J., et al., "Proteomic Analysis of Exosomes Secreted by Human Mesothelioma Cells," Am. J. Pathol., 164(5): 1807-1815 (2004).
Henry, M. D., et al., "A Prostate-Specific Membrane Antigen-Targeted Monoclonal Antibody-Chemotherapeutic Cojugate Designed for the Treatment of Prostate Cancer," Cancer Research, 64: 7995-8001 (2004).
Herrnberger, L et al., "The role of plasmalemma vesicle-associated protein (PLVAP) in andothelial cells of Schlemm's canal and ocular capillaries," Experimental Eye Research, vol. 105; 27-33 (2012).
Ho, S., et al., "Internal Radiation Therapy for Patients with Primary or Metastatic Hepatic Cancer," Cancer, 83: 1894-1907 (1998).
Holm, P., et al., "Functional mapping and single chain construction of the anti-cytokeratin 8 monoclonal antibody TS1," Molecular Immunology, 44: 1075-1084 (2007).
Hu P. et al., Comparison of the three different targeted tissue factor fusion proteins for inducing a tumor vessel thrombosis, Cancer Research, 2003, V. 63, N. 16, p. 5046-5053, Full Text, pp. 5046-5048.
Huang, M. et al., "The Mechanism of an Inhibitory Antibody on TF-initiated Blood Coagulation Revealed by the Crystal Structures of Human Tissue Factor, Fab 5G9 and TF 5G9 Complex," J. Mol. Biol., vol. 275; 873-894 (1998).
Huang ZJ et al., Humanised monoclonal antibody TNT-3 mediated truncated tissue factor for the treatment of H22 hepatoma-bearing mice. Chin J Oncol., Apr. 2012, vol. 34, No. 4, pp. 249-253.
Huang, X., et al., "Tumor Infarction in Mice by Antibody-Directed Targeting of Tissue Factor to Tumor Vasculature", Science, 275: 547-550 (1997).
Jang et al., "The structural basis for DNA binding by an anti-DNA autoantibody", Molec. Immunol. 35; 1207-1217 (1998).
Jemal, A., et al., "Global Cancer Statistics", CA Cancer J Clin, 51: 69-90 (2011).

(56) References Cited

OTHER PUBLICATIONS

Jiang, B., et al., "A Novel Peptide Isolated from a Phage Display Peptide Library with Trastuzumab Can Mimic Antigen Epitope of HER-2," J. Biol. Chem., 280(6): 4656-4662 (2005).
Kelland, L. R., "'Of mice and men': values and liabilities of the athymic nude mouse model in anticancer drug development," Eur. J. Cancer, 40: 827-836 (2004).
Keuschnigg, J., et al., "The Prototype Endothelial Marker PAL-E is a Leukocyte Trafficking Molecule", Blood, 114(2): 478-484 (2009).
Klein, F. et al., Somatic mutations of the Immunoglobulin Framework are Generally Required for Broad and Potent HIV-1 Neutralization, Cell, vol. 153; No. 1; 126-138 (2013).
Kobayashi et al., "Tryptophan H33 plays an important role in pyrimidine (6-4) pyrimidone photoproduct binding by a high-affinity antibody", Protein Engineering 12; 879-844 (1999).
Lee, J.-S., et al., "Classification and Prediction of Survival in Hepatocellular Carcinoma by Gene Expression Profiling," Hepatology, 40: 667-676 (2004).
Lin, M.-L., et al., "Involvement of maternal embryonic leucine zipper kinase (MELK) in mammmary carcinogenesis through interaction with Bcl-G, a pro-apoptotic member of the Bcl-2 family," Breast Cancer Research, 9: R17 (2007).
Liu, Z., et al., "Fine mapping of the antigen-antibody interaction of scFv215, a recombinant antibody inhibiting RNA polymerase II from Drosophila melanogaster," J. Mol. Recognit., 12: 103-111 (1999).
Llovet, J.M., et al., "Systematic Review of Randomized Trials for Unresectable Hepatocellular Carcinoma: Chemoembolization Improves Survival", Hepatology, 37: 429-442 (2003).
Llovet, J.M., et al., "Sorafenib in Advanced Hepatocellular Carcinoma", The New England Journal of Medicine, 359: 378-390 (2008).
MacCallum, R. M., et al., "Antibody-antigen Interactions: Contact Analysis and Binding Site Topography," J. Mol. Biol., 262: 732-745 (1996).
Mackman, Nigel, "Role of Tissue Factor in Hemostasis, Thrombosis, and Vascular Development", Arterioscler Thromb Vasc Biol, 24: 1015-1022 (2004).
Madden, S.L., et al., "Vascular Gene Expression in Nonneoplastic and Malignant Brain", American Journal of Pathology, 165(2): 601-608 (2004).
Mariuzza, R. A., et al., "The Structural Basis of Antigen-Antibody Recognition," Ann. Rev. Biophys. Biophys. Chem., 16: 139-159 (1987).
Mcdevitt, M. R., et al., "An α-Particle Emitting Antibody ([213Bi]J591) for Radioimmunotherapy of Prostate Cancer," Cancer Research, 60: 6095-6100 (2000).
Murata, S., et al., "Transcatheter Arterial Chemoembolization Based on Hepatic Hemodynamics for Hepatocellular Carcinoma", The Scientific World Journal, Article ID 479805; 8 pages (2013).
Nishi, Y., et al., "Histopathological manifestations of membranoproliferative glomerulonephritis and glomerular expression of plasmalemmal vesicle-associated protein-1 in a patient with polycythemia vera," Clinical Nephrology, vol. 74; 393-398 (2010).
Nuyten, D. S. A., et al., "Using Microarray Analysis as a Prognostic and Predictive Tool in Oncology: Focus on Breast Cancer and Normal Tissue Toxicity," Seminars in Radiation Oncology, 18: 105-114 (2008).
Ørntoft, T. F., et al., "Genome-wide Study of Gene Copy Numbers, Transcripts, and Protein Levels in Pairs of Non-invasive and Invasive Human Transitional Cell Carconomas," Molecular & Cellular Proteomics, 1: 37-45 (2002).
Pakula A.A. et al., Genetic analysis of protein stability and function, Annual review of genetics, 1989, V. 23, N. 1, p. 289-310, p. 305-306.
Perz, J.F., et al., "The Contributions of Hepatitis B Virus and Hepatitis C virus Infections to Cirrhosis and Primary Liver Cancer Worldwide", Journal of Hepatology, 45: 529-538 (2006).

Petersen, L.C., et al., "Characterization of Recombinant Murine Factor IIa and Recombinant Murine Tissue Factor: A Human-Murine Compatibility Study", Thrombosis Res, 116: 75-85 (2005).
Pettersen, R. D., et al., "CD47 Signals T Cell Death," J. Immunol., 162: 7031-7040 (1999).
Philipp, J., et al., "Soluble Tissue Factor Induces Coagulation on Tumor Endothelial Cells In Vivo if Coadministered With Low-Dose Lipopolysaccharides", Arterioscler Thromb Vasc Biol, 23: 905-910 (2003).
Ran, S. et al., "Infraction of Solid Hodgkin's Tumors in Mice by Antibody-directed Targeting of Tissue Factor to Tumor Vasculature," Cancer Research, vol. 58; 4646-4653 (1998).
Rantakari P. et al., The endothelial protein PLVAP in lymphatics controls the entry of lymphocytes and antigens into lymph nodes, Nature immunology, 2015, V. 16, N. 4, p. 386-401, Full Text, p. 387-389.
Rhodes, D. R., et al., "Large-scale meta-analysis of cancer microarray data identifies common transcriptional profiles of neoplastic transformation and progression," PNAS, 101(25): 9309-9314 (2004).
Rudikoff, S., et al., "Single amino acid substitution altering antigen-binding specificity," Proc. Natl. Acad. Sci. USA, 79: 1979-1983 (1982).
Safdari, Y. et al., "Antibody humanization methods—a review and update," Biotechnology and Genetic Engineering Reviews, vol. 29; No. 2; 175-186 (2013).
Saijo, N., "What are the reasons for negative phase III trials of molecular-target-based drugs?" Cancer Sci., 95: 772-776 (2004).
Schier, R., et al., "Isolation of Picomolar Affinity Anti-c-crbB-2 Single-chain Fv by Molecular Evolution of the Complementarity Determining Regions in the Center of the Antibody Binding Site," J. Mol. Biol., 263: 551-567 (1996).
Shchegolev A.A et al., Vascularization of the tissue of hepatocellular carcinoma depends on the degree of its differentiation, Bulletin of Experimental Biology and Medicine, 2012, p. 153, N. 4, p. 480-484, Full Text.
Siegel, R., et al., "Cancer Statistics, 2012", CA Cancer J Clin, 62: 10-29 (2012).
Simard, E.P., et al., "Cancers With Increasing Incidence Trends in the United States: 1999 Through 2008", CA Cancer J Clin, 62: 118-128 (2012).
Simonetti, R.G., et al., "Hepatocellular Carcinoma. A Worldwide Problem and the Major Risk Factors", Dig Dis Sci, 36: 962-972 (1991).
Skerra A. et al., Assembly of a functional immunoglobulin Fv fragment in *Escherichia coli*, Science, 1988, V. 240, N. 4855, p. 1038-1041, p. 1039-1040.
Snyder, L.A., et al., "Expression of Human Tissue Factor Under the Control of the Mouse Tissue Factor Promoter Mediates Normal Hemostasis in Knock-In Mice", Journal of Thrombosis and Haemostasis, 6: 306-314 (2007).
Sotiriou, C. et al., "Gene Expression Profiling in Breast Cancer: Understanding the Molecular Basis of Histologic Grade to Improve Prognosis," Journal of the National Cancer Institute, vol. 98; No. 4; 262-272 (2006).
Stan, R.-V., et al., "Immunoisolation and Partial Characterization of Endothelial Plasmalemmal Vesicles (Caveolae)," Molecular Biology of the Cell, 8: 595-605 (1997).
Stan, R. V., et al., "PV1 Is a Key Structural Component for the Formation of the Stomatal and Fenestral Diaphragms," Molecular Biology of the Cell, 15: 3615-3630 (2004).
Stan, R.-V., et al., "PV-1 is a Component of the Fenestral and Stomatal Diaphragms in Fenestrated Endothelia", PNAS, 96(23): 13202-13207 (1999).
Stancovski, I., et al., "Mechanistic aspects of the opposing effects of monoclonal antibodies to the ERBB2 receptor on tumor growth," Proc. Natl. Acad. Sci. USA, 88: 8691-8695 (1991).
Strickland, L. A., et al., "Plasmalemmal vesicle-associated protein (PLVAP) is expressed by tumour endothelium and is upregulated by vascular endothelial growth factor-A (VEGF)," J. Pathol., 206: 466-475 (2005).
Thorgeirsson, S. S., et al., "Molecular prognostication of liver cancer: End of the beginning," Journal of Hepatology, 44: 798-805 (2006).

(56) References Cited

OTHER PUBLICATIONS

Vajdos, F. F., et al., "Comprehensive Functional Maps of the Antigen-binding Site of an Anti-ErbB2 Antibody Obtained with Shotgun Scanning Mutagenesis," J. Mol. Biol., 320: 415-428 (2002).
Van 't Veer, L. J., et al., "Gene expression profiling predicts clinical outcome of breast cancer," Nature, 415: 530-536 (2002).
Wang et al., "Plasmalemmal Vesicle Associated Protein (PLVAP) as a therapeutic target for treatment of hepatocellular carcinoma", BMC Cancer 14: 815-826 (2014).
Winkler, K., et al., "Changing the Antigen Binding Specificity by Single Point Mutations of an Anti-p24 (HIV-1) Antibody," J. Immunol., 165: 4505-4514 (2000).
Wolff, A. C., et al., "American Society of Clinical Oncology/ College of American Pathologists Guideline Recommendations for Human Epidermal Growth Factor Receptor 2 Testing in Breast Cancer," Arch. Pathol. Lab. Med., 131: 18-43 (2007).
Wu, H., et al., "Humanization of a Murine Monoclonal Antibody by Simultaneous Optimization of Framework and CDR Residues," J. Mol. Biol., 294(1): 151-162 (1999).
Corrected Notice of Allowability from U.S. Appl. No. 13/126,734, mailed Apr. 8, 2014.
European Search Report for European Patent Application No. EP14275235, "Therapeutic Biologic for Treatment of Hepatocellular Carcinoma", dated Aug. 6, 2015. (4261.1003-007).
Final Office Action from U.S. Appl. No. 12/933,248, mailed Nov. 22, 2013.
Final Office Action from U.S. Appl. No. 14/539,577, mailed Apr. 18, 2016.
Final Office Action from U.S. Appl. No. 15/270,430, mailed Aug. 6, 2018.
International Preliminary Report on Patentability from International Application No. PCT/US2009/001689, "Methods and Agents for the Diagnosis and Treatment of Hepatocellular Carcinoma," mailed Sep. 30, 2010.
International Preliminary Report on Patentability from International Application No. PCT/US2009/002196, "Methods, Agents and Kits for the Detection of Cancer," dated Oct. 12, 2010.
International Preliminary Report on Patentability from International Application No. PCT/US2009/056382, "Methods and Agents for the Diagnosis and Treatment of Hepatocellular Carcinoma," mailed May 12, 2011.
International Search Report and Written Opinion of the International Searching Authority from International Application No. PCT/US2009/001689, "Methods and Agents for the Diagnosis and Treatment of Hepatocellular Carcinoma," mailed Jul. 23, 2009.
International Search Report and Written Opinion of the International Searching Authority from International Application No. PCT/US2009/002196, "Methods, Agents and Kits for the Detection of Cancer," mailed Jul. 24, 2009.
International Search Report and Written Opinion of the International Searching Authority from International Application No. PCT/US2009/056382, "Methods and Agents for the Diagnosis and Treatment of Hepatocellular Carcinoma," mailed Dec. 21, 2009.
Interview Summary for U.S. Appl. No. 12/933,248, mailed May 29, 2014.
Interview Summary for U.S. Appl. No. 13/126,734, mailed Feb. 6, 2014.
Notice of Abandonment for U.S. Appl. No. 12/937,207, mailed Sep. 26, 2013.
Notice of Allowance for U.S. Appl. No. 14/335,129, mailed Sep. 13, 2016.
Notice of Allowance for U.S. Appl. No. 14/336,441, mailed Apr. 12, 2016.
Notice of Allowance from U.S. Appl. No. 12/933,248, mailed Feb. 14, 2014.
Notice of Allowance from U.S. Appl. No. 13/126,734, mailed Mar. 12, 2014.
Notice of Allowance for U.S. Appl. No. 14/539,577, mailed Jun. 30, 2016.
Notice of Allowance for U.S. Appl. No. 15/370,711, mailed Mar. 27, 2019.
Notice of Allowance for U.S. Appl. No. 15/270,430, mailed Apr. 24, 2019.
Office Action for U.S. Appl. No. 14/335,129, mailed Feb. 19, 2016.
Office Action for U.S. Appl. No. 14/336,441, mailed Dec. 30, 2015.
Office Action from U.S. Appl. No. 12/933,248, mailed May 21, 2013.
Office Action from U.S. Appl. No. 15/270,430, mailed Mar. 2, 2018.
Office Action from U.S. Appl. No. 15/270,430, mailed Nov. 13, 2018.
Office Action from U.S. Appl. No. 13/126,734, mailed Aug. 28, 2013.
Office Action from U.S. Appl. No. 14/539,577, entitled: "Therapeutic Biologic for Treatment of Hepatocellular Carcinoma", mailed Jan. 8, 2016.
Office Action for U.S. Appl. No. 15/370,711, mailed Oct. 19, 2018.
Response to Rule 312 Communication for U.S. Appl. No. 13/126,734, entitled: "Methods and Agents for the Diagnosis and Treatment of Hepatocellular Carcinoma", mailed Aug. 4, 2014.
Response to Rule 312 Communication for U.S. Appl. No. 14/336,441, entitled: "Methods and Agents for the Diagnosis and Treatment of Hepatocellular Carcinoma", mailed May 20, 2016.
Singapore International Search Report for Application No. 10201407557V, entitled: "Therapeutic Biologic for Treatment of Hepatocellular Carcinoma ," mailed Aug. 8, 2017.
Office Action for U.S. Appl. No. 16/116,644, mailed May 18, 2020.
Final Office Action for U.S. Appl. No. 16/116,644, mailed Sep. 8, 2020.
Notice of Allowance for U.S. Appl. No. 16/116,644, mailed Sep. 23, 2020.
Notice of Allowance for U.S. Appl. No. 16/450,370, mailed Feb. 11, 2022.
Office Action for U.S. Appl. No. 16/513,148, mailed Mar. 23, 2022.
Burrows, F.J., et al., "A Murine Model for Antibody-Directed Targeting of Vascular Endothelial Cells in Solid Tumors", Cancer Research, 52: 5954-5962 (1992).
Gonzales et al., "Minimizing the immunogenicity of antibodies for clinical application", Tumour. Biol., vol. 26, No. 1, Jan.-Feb. 2005, pp. 31-43.
Notice of Allowance for U.S. Appl. No. 16/513,148, mailed Aug. 23, 2022.
Yang Jiahui et al. "Therapeutic potential and challenges of targeting receptor tyrosine kinase ROR1 with monoclonal antibodies in B-cell malignancies." PloS one vol. 6; No. 6; e21018; 15 pages (2011).

* cited by examiner

```
mglamehggs yaraggssrg cwyylryffl fvsliqflii lglvlfmvyg nvhvstesnl
qaterraegl ysqllgltas qsnltkelnf ttrakdaimq mwlnarrdld rinasfrqcq
gdrviytnnq rymaaiilse kqcrdqfkdm nkscdallfm lnqkvktlev eiakektict
kdkesvllnk rvaeeqlvec vktrelqhqe rqlakeqlqk vqalclpldk dkfemdlrnl
wrdsiiprsl dnlgynlyhp lgselasirr acdhmpslms skveelarsl radiervare
nsdlqrqkle aqqglrasqe akqkvekeaq areaklqaec srqtqlalee kavlrkerdn
lakeleeekkr eaeqlrmela irnsaldtci ktksqpmmpv srpmgpvpnp qpidpaslee
fkrkilesqr ppagipvaps sg (SEQ ID NO: 2)
```

FIG. 19

EVQLQQSGAEFVRSGASVKLSCTASGFNIKDYYIHWVKQRPEQGLEWIGWIDPENGDIEYAPKFQGKAT
MTADTSSNTAYLQFSSLTSEDTAVYYCLYQEGSWGQGTTLTVSSA (SEQ ID NO: 3)

FIG. 20

DVVMTQTPLTLSVTIGQPASISCKSSQSLLNSDGKTYLNWLLQRPGQSPKRLIYLVSKLDSGVPDRF
TGSGSGTDFTLKISRVEAEDLGVYYCWQGTHFPFTFGGGTKLEIK (SEQ ID NO: 4)

FIG. 21

QVQLQQPGAELVRPGASVKLSCKASGYTFTSNYINWVKQRPGQGLEWIGNIYPSDGFTNYNQKFKDRAT
LTVDKSSSTAYMQLSSPTSEDSAVYYCTRNFDVWGAGTTVTVSSA (SEQ ID NO: 5)

FIG. 22

DVVMTQTPLSLPVSLGDQASISCRSSQSLVHSNGNTYLQWYLQKPGQSPKLLIYTVSNRFSGVPDRFSG
SGSGPDFTLKISRVEAEDLGVYFCSQSTHVPFTFGSGTKLEIK (SEQ ID NO: 6)

FIG. 23

```
MQVQLVQSGS ELKKPGASVK VSCKASGYTF TSNYINWVRQ APGQGLEWMG NIYPSDGFTN
YNQKFKDRVT ITVDKSTSTA YMELSSLRSE DTAVYYCTRN FDVWGQGTTV TVSSASTKGP
SVFPLAPCSR STSESTAALG CLVKDYFPEP VTVSWNSGAL TSGVHTFPAV LQSSGLYSLS
SVVTVPSSSL GTKTYTCNVD HKPSNTKVDK RVESKYGPPC PSCPGgggsg gggsggggsS
GTTNTVAAYN LTWKSTNFKT ILEWEPKPVN QVYTVQISTK SGDWKSKCFY TTDTECDLTD
EIVKDVKQTY LARVFSYPAG NVESTGSAGE PLYENSPEFT PYLETNLGQP TIQSFEQVGT
KVNVTVEDER TLVRRNNTFL SLRDVFGKDL IYTLYYWKSS SSGKKTAKTN TNEFLIDVDK
GENYCFSVQA VIPSRTVNRK STDSPVECMG QEKGEFRE (SEQ ID NO: 23)
```

FIG. 24

SEQUENCE LISTING

```
Sequence total quantity: 50
SEQ ID NO: 1              moltype = AA  length = 219
FEATURE                   Location/Qualifiers
source                    1..219
                          mol_type = protein
                          organism = Homo sapiens
SEQUENCE: 1
SGTTNTVAAY NLTWKSTNFK TILEWEPKPV NQVYTVQIST KSGDWKSKCF YTTDTECDLT   60
DEIVKDVKQT YLARVFSYPA GNVESTGSAG EPLYENSPEF TPYLETNLGQ PTIQSFEQVG  120
TKVNVTVEDE RTLVRRNNTF LSLRDVFGKD LIYTLYYWKS SSSGKKTAKT NTNEFLIDVD  180
KGENYCFSVQ AVIPSRTVNR KSTDSPVECM GQEKGEFRE                         219

SEQ ID NO: 2              moltype = AA  length = 442
FEATURE                   Location/Qualifiers
source                    1..442
                          mol_type = protein
                          organism = Homo sapiens
SEQUENCE: 2
MGLAMEHGGS YARAGGSSRG CWYYLRYFFL FVSLIQFLII LGLVLFMVYG NVHVSTESNL   60
QATERRAEGL YSQLLGLTAS QSNLTKELNF TTRAKDAIMQ MWLNARRDLD RINASFRQCQ  120
GDRVIYTNNQ RYMAAIILSE KQCRDQFKDM NKSCDALLFM LNQKVKTLEV EIAKEKTICT  180
KDKESVLLNK RVAEEQLVEC VKTRELQHQE RQLAKEQLQK VQALCLPLDK DKFEMDLRNL  240
WRDSIIPRSL DNLGYNLYHP LGSELASIRR ACDHMPSLMS SKVEELARSL RADIERVARE  300
NSDLQRQKLE AQQGLRASQE AKQKVEKEAQ AREAKLQAEC SRQTQLALEE KAVLRKERDN  360
LAKELEEKKR EAEQLRMELA IRNSALDTCI KTKSQPMMPV SRPMGPVPNP QPIDPASLEE  420
FKRKILESQR PPAGIPVAPS SG                                           442

SEQ ID NO: 3              moltype = AA  length = 114
FEATURE                   Location/Qualifiers
source                    1..114
                          mol_type = protein
```

```
                            organism = Mus musculus
SEQUENCE: 3
EVQLQQSGAE FVRSGASVKL SCTASGFNIK DYYIHWVKQR PEQGLEWIGW IDPENGDIEY    60
APKFQGKATM TADTSSNTAY LQFSSLTSED TAVYYCLYQE GSWGQGTTLT VSSA         114

SEQ ID NO: 4              moltype = AA  length = 112
FEATURE                   Location/Qualifiers
source                    1..112
                          mol_type = protein
                          organism = Mus musculus
SEQUENCE: 4
DVVMTQTPLT LSVTIGQPAS ISCKSSQSLL NSDGKTYLNW LLQRPGQSPK RLIYLVSKLD    60
SGVPDRFTGS GSGTDFTLKI SRVEAEDLGV YYCWQGTHFP FTFGGGTKLE IK           112

SEQ ID NO: 5              moltype = AA  length = 114
FEATURE                   Location/Qualifiers
source                    1..114
                          mol_type = protein
                          organism = Mus musculus
SEQUENCE: 5
QVQLQQPGAE LVRPGASVKL SCKASGYTFT SNYINWVKQR PGQGLEWIGN IYPSDGFTNY    60
NQKFKDRATL TVDKSSSTAY MQLSSPTSED SAVYYCTRNF DVWGAGTTVT VSSA         114

SEQ ID NO: 6              moltype = AA  length = 112
FEATURE                   Location/Qualifiers
source                    1..112
                          mol_type = protein
                          organism = Mus musculus
SEQUENCE: 6
DVVMTQTPLS LPVSLGDQAS ISCRSSQSLV HSNGNTYLQW YLQKPGQSPK LLIYTVSNRF    60
SGVPDRFSGS GSGPDFTLKI SRVEAEDLGV YFCSQSTHVP FTFGSGTKLE IK           112

SEQ ID NO: 7              moltype = AA  length = 113
FEATURE                   Location/Qualifiers
REGION                    1..113
                          note = humanized-heavy chain variable region
source                    1..113
                          mol_type = protein
                          organism = synthetic construct
SEQUENCE: 7
EVQLVQSGAE FKKPGASVKL SCTASGFNIK DYYIHWVKQA PGQGLEWIGW IDPENGDIEY    60
APKFQGRATM TADTSTNTAY LEFSSLRSED TAVYYCLYQE GSWGQGTTVT VSS          113

SEQ ID NO: 8              moltype = AA  length = 113
FEATURE                   Location/Qualifiers
REGION                    1..113
                          note = humanized-heavy chain variable region
source                    1..113
                          mol_type = protein
                          organism = synthetic construct
SEQUENCE: 8
EVQLVQSGAE VKKPGASVKL SCTASGFNIK DYYIHWVRQA PGQGLEWIGW IDPENGDIEY    60
APKFQGRATM TADTSTNTAY LEFSSLRSED TAVYYCLYQE GSWGQGTTVT VSS          113

SEQ ID NO: 9              moltype = AA  length = 113
FEATURE                   Location/Qualifiers
REGION                    1..113
                          note = humanized-heavy chain variable region
source                    1..113
                          mol_type = protein
                          organism = synthetic construct
SEQUENCE: 9
EVQLVQSGAE VKKPGASVKV SCTASGFNIK DYYIHWVRQA PGQGLEWIGW IDPENGDIEY    60
APKFQGRATI TADTSTNTAY MEFSSLRSED TAVYYCLYQE GSWGQGTTVT VSS          113

SEQ ID NO: 10             moltype = AA  length = 113
FEATURE                   Location/Qualifiers
REGION                    1..113
                          note = humanized-heavy chain variable region
source                    1..113
                          mol_type = protein
                          organism = synthetic construct
SEQUENCE: 10
EVQLVQSGAE VKKPGASVKV SCTASGFNIK DYYIHWVRQA PGQGLEWIGW IDPENGDIEY    60
APKFQGRATI TADTSTDTAY MEFSSLRSED TAVYYCLYQE GSWGQGTTVT VSS          113

SEQ ID NO: 11             moltype = AA  length = 113
FEATURE                   Location/Qualifiers
REGION                    1..113
```

-continued

```
                         note = humanized-heavy chain variable region
source                   1..113
                         mol_type = protein
                         organism = synthetic construct
SEQUENCE: 11
EVQLVQSGAE VKKPGASVKV SCTASGFNIK DYYIHWVRQA PGQGLEWIGW IDPENGDIEY    60
APKFQGRVTI TADTSTDTAY MELSSLRSED TAVYYCLYQE GSWGQGTTVT VSS          113

SEQ ID NO: 12            moltype = AA   length = 112
FEATURE                  Location/Qualifiers
REGION                   1..112
                         note = humanized-light chain variable region
source                   1..112
                         mol_type = protein
                         organism = synthetic construct
SEQUENCE: 12
DVVMTQSPLT LSVTLGQPAS ISCKSSQSLL NSDGKTYLNW LQQRPGQSPR RLIYLVSKLD    60
SGVPDRFTGS GSGTDFTLKI SRVEAEDVGV YYCWQGTHFP FTFGGGTKVE IK           112

SEQ ID NO: 13            moltype = AA   length = 112
FEATURE                  Location/Qualifiers
REGION                   1..112
                         note = humanized-light chain variable region
source                   1..112
                         mol_type = protein
                         organism = synthetic construct
SEQUENCE: 13
DVVMTQSPLS LPVTLGQPAS ISCKSSQSLL NSDGKTYLNW LQQRPGQSPR RLIYLVSKLD    60
SGVPDRFTGS GSGTDFTLKI SRVEAEDVGV YYCWQGTHFP FTFGGGTKVE IK           112

SEQ ID NO: 14            moltype = AA   length = 112
FEATURE                  Location/Qualifiers
REGION                   1..112
                         note = humanized-light chain variable region
source                   1..112
                         mol_type = protein
                         organism = synthetic construct
SEQUENCE: 14
DVVMTQSPLS LPVTLGQPAS ISCKSSQSLL NSDGKTYLNW LQQRPGQSPR RLIYLVSKLD    60
SGVPDRFSGS GSGTDFTLKI SRVEAEDVGV YYCWQGTHFP FTFGGGTKVE IK           112

SEQ ID NO: 15            moltype = AA   length = 113
FEATURE                  Location/Qualifiers
REGION                   1..113
                         note = humanized-heavy chain variable region
source                   1..113
                         mol_type = protein
                         organism = synthetic construct
SEQUENCE: 15
QVQLVQSGAE LKKPGASVKL SCKASGYTFT SNYINWVKQA PGQGLEWIGN IYPSDGFTNY    60
NQKFKDRATL TVDKSTSTAY MELSSLRSED SAVYYCTRNF DVWGQGTTVT VSS          113

SEQ ID NO: 16            moltype = AA   length = 113
FEATURE                  Location/Qualifiers
REGION                   1..113
                         note = humanized-heavy chain variable region
source                   1..113
                         mol_type = protein
                         organism = synthetic construct
SEQUENCE: 16
QVQLVQSGSE LKKPGASVKL SCKASGYTFT SNYINWVKQA PGQGLEWIGN IYPSDGFTNY    60
NQKFKDRATL TVDKSTSTAY MELSSLRSED TAVYYCTRNF DVWGQGTTVT VSS          113

SEQ ID NO: 17            moltype = AA   length = 113
FEATURE                  Location/Qualifiers
REGION                   1..113
                         note = humanized-heavy chain variable region
source                   1..113
                         mol_type = protein
                         organism = synthetic construct
SEQUENCE: 17
QVQLVQSGSE LKKPGASVKL SCKASGYTFT SNYINWVRQA PGQGLEWIGN IYPSDGFTNY    60
NQKFKDRVTL TVDKSTSTAY MELSSLRSED TAVYYCTRNF DVWGQGTTVT VSS          113

SEQ ID NO: 18            moltype = AA   length = 113
FEATURE                  Location/Qualifiers
REGION                   1..113
                         note = humanized-heavy chain variable region
source                   1..113
```

```
                         mol_type = protein
                         organism = synthetic construct
SEQUENCE: 18
QVQLVQSGSE LKKPGASVKV SCKASGYTFT SNYINWVRQA PGQGLEWIGN IYPSDGFTNY    60
NQKFKDRVTI TVDKSTSTAY MELSSLRSED TAVYYCTRNF DVWGQGTTVT VSS          113

SEQ ID NO: 19            moltype = AA    length = 113
FEATURE                  Location/Qualifiers
REGION                   1..113
                         note = humanized-heavy chain variable region
source                   1..113
                         mol_type = protein
                         organism = synthetic construct
SEQUENCE: 19
QVQLVQSGSE LKKPGASVKV SCKASGYTFT SNYINWVRQA PGQGLEWMGN IYPSDGFTNY    60
NQKFKDRVTI TVDKSTSTAY MELSSLRSED TAVYYCTRNF DVWGQGTTVT VSS          113

SEQ ID NO: 20            moltype = AA    length = 112
FEATURE                  Location/Qualifiers
REGION                   1..112
                         note = humanized-light chain variable region
source                   1..112
                         mol_type = protein
                         organism = synthetic construct
SEQUENCE: 20
DVVMTQSPLS LPVTLGQPAS ISCRSSQSLV HSNGNTYLQW YLQKPGQSPQ LLIYTVSNRF    60
SGVPDRFSGS GSGPDFTLKI SRVEAEDVGV YFCSQSTHVP FTFGQGTKLE IK          112

SEQ ID NO: 21            moltype = AA    length = 112
FEATURE                  Location/Qualifiers
REGION                   1..112
                         note = humanized-light chain variable region
source                   1..112
                         mol_type = protein
                         organism = synthetic construct
SEQUENCE: 21
DVVMTQSPLS LPVTLGQPAS ISCRSSQSLV HSNGNTYLQW YLQKPGQSPQ LLIYTVSNRF    60
SGVPDRFSGS GSGTDFTLKI SRVEAEDVGV YFCSQSTHVP FTFGQGTKLE IK          112

SEQ ID NO: 22            moltype = AA    length = 112
FEATURE                  Location/Qualifiers
REGION                   1..112
                         note = humanized-light chain variable region
source                   1..112
                         mol_type = protein
                         organism = synthetic construct
SEQUENCE: 22
DVVMTQSPLS LPVTLGQPAS ISCRSSQSLV HSNGNTYLQW YLQKPGQSPQ LLIYTVSNRF    60
SGVPDRFSGS GSGPDFTLKI SRVEAEDVGV YYCSQSTHVP FTFGQGTKLE IK          112

SEQ ID NO: 23            moltype = AA    length = 458
FEATURE                  Location/Qualifiers
REGION                   1..458
                         note = Antibody conjugate
source                   1..458
                         mol_type = protein
                         organism = synthetic construct
SEQUENCE: 23
MQVQLVQSGS ELKKPGASVK VSCKASGYTF TSNYINWVRQ APGQGLEWMG NIYPSDGFTN    60
YNQKFKDRVT ITVDKSTSTA YMELSSLRSE DTAVYYCTRN FDVWGQGTTV TVSSASTKGP   120
SVFPLAPCSR STSESTAALG CLVKDYFPEP VTVSWNSGAL TSGVHTFPAV LQSSGLYSLS   180
SVVTVPSSSL GTKTYTCNVD HKPSNTKVDK RVESKYGPPC PSCPGGGGSG GGGSGGGGSS   240
GTTNTVAAYN LTWKSTNFKT ILEWEPKPVN QVYTVQISTK SGDWKSKCFY TTDTECDLTD   300
EIVKDVKQTY LARVFSYPAG NVESTGSAGE PLYENSPEFT PYLETNLGQP TIQSFEQVGT   360
KVNVTVEDER TLVRRNNTFL SLRDVFGKDL IYTLYYWKSS SSGKKTAKTN TNEFLIDVDK   420
GENYCFSVQA VIPSRTVNRK STDSPVECMG QEKGEFRE                           458

SEQ ID NO: 24            moltype = AA    length = 438
FEATURE                  Location/Qualifiers
source                   1..438
                         mol_type = protein
                         organism = Mus musculus
SEQUENCE: 24
MGLSMDRSPY ARTGDQQRGC WYYLRYFFLF VSLIQFLIIL GLVLFMIYGN VHATTESSLR    60
ATEIRADSLY SQVVGLSASQ ANLSKQLNIS LLVKETVMQQ LLTTRREMER INASFRQCQG   120
DLITYINYNR FIAAIILSEK QCQEQLKEVN KTCEALLFKL GEKVKTLEME VAKEKAVCSK   180
DKESLLAGKR QAEEQLEACG KAREROQQEQ QVTEENLRKV QSLCIPLDQE KFQADVLSAW   240
RDSLIYRTLE TLPYHYQLMP EYASLRRTCE SLPGIMTTKI EELARGLRAG IERVTRENAE   300
LRRQKLELER AAQAAQEARA RAGTEAQARE TQLRAECARQ TQLALEEKAA LRAQRDNLER   360
```

```
ELEARKRELE QLRTEVDVRI SALDTCVKAK SLPAVPPRVS GPPPNPPPID PASLEEFKKR    420
ILESQRLPVV NPAAQPSG                                                 438

SEQ ID NO: 25              moltype = AA  length = 12
FEATURE                    Location/Qualifiers
source                     1..12
                           mol_type = protein
                           organism = Homo sapiens
SEQUENCE: 25
PPAGIPVAPS SG                                                        12

SEQ ID NO: 26              moltype = AA  length = 26
FEATURE                    Location/Qualifiers
source                     1..26
                           mol_type = protein
                           organism = Homo sapiens
SEQUENCE: 26
LAIRNSALDT CIKTKSQPMM PVSRPM                                         26

SEQ ID NO: 27              moltype = DNA  length = 23
FEATURE                    Location/Qualifiers
misc_feature               1..23
                           note = Primer sequence
source                     1..23
                           mol_type = other DNA
                           organism = synthetic construct
SEQUENCE: 27
tgtcctgatc agtaacactg tcc                                            23

SEQ ID NO: 28              moltype = DNA  length = 26
FEATURE                    Location/Qualifiers
misc_feature               1..26
                           note = Primer sequence
source                     1..26
                           mol_type = other DNA
                           organism = synthetic construct
SEQUENCE: 28
tgagagtgta gagtccagac tgcagg                                         26

SEQ ID NO: 29              moltype = DNA  length = 29
FEATURE                    Location/Qualifiers
misc_feature               1..29
                           note = Primer sequence
source                     1..29
                           mol_type = other DNA
                           organism = synthetic construct
SEQUENCE: 29
gatcctgaca tccagatgac ccagactcc                                      29

SEQ ID NO: 30              moltype = DNA  length = 26
FEATURE                    Location/Qualifiers
misc_feature               1..26
                           note = Primer sequence
source                     1..26
                           mol_type = other DNA
                           organism = synthetic construct
SEQUENCE: 30
cacactcatt cctgttgaag ctcttg                                         26

SEQ ID NO: 31              moltype = DNA  length = 23
FEATURE                    Location/Qualifiers
misc_feature               1..23
                           note = Primer sequence
source                     1..23
                           mol_type = other DNA
                           organism = synthetic construct
SEQUENCE: 31
gacatccaga tgacccagac tcc                                            23

SEQ ID NO: 32              moltype = DNA  length = 55
FEATURE                    Location/Qualifiers
misc_feature               1..55
                           note = Primer sequence
source                     1..55
                           mol_type = other DNA
                           organism = synthetic construct
SEQUENCE: 32
agagccacct ccgcctgaac cgcctccacc tgtacatcca caaggattgc attcc          55
```

| SEQ ID NO: 33 | moltype = DNA length = 52 |
|---|---|
| FEATURE | Location/Qualifiers |
| misc_feature | 1..52 |
| | note = Primer sequence |
| source | 1..52 |
| | mol_type = other DNA |
| | organism = synthetic construct |

SEQUENCE: 33
ggcggaggtg gctctggcgg tgcggatcg tcaggcacta caaatactgt gg          52

| SEQ ID NO: 34 | moltype = DNA length = 24 |
|---|---|
| FEATURE | Location/Qualifiers |
| misc_feature | 1..24 |
| | note = Primer sequence |
| source | 1..24 |
| | mol_type = other DNA |
| | organism = synthetic construct |

SEQUENCE: 34
cagtgtgagg tgcaactggt ggag          24

| SEQ ID NO: 35 | moltype = DNA length = 40 |
|---|---|
| FEATURE | Location/Qualifiers |
| misc_feature | 1..40 |
| | note = Primer sequence |
| source | 1..40 |
| | mol_type = other DNA |
| | organism = synthetic construct |

SEQUENCE: 35
acaattcccc tctagatttt gtttaacttt aagaaggaga          40

| SEQ ID NO: 36 | moltype = DNA length = 39 |
|---|---|
| FEATURE | Location/Qualifiers |
| misc_feature | 1..39 |
| | note = Primer sequence |
| source | 1..39 |
| | mol_type = other DNA |
| | organism = synthetic construct |

SEQUENCE: 36
caaaattatt tctagatttc gggctttgtt agcagccgg          39

| SEQ ID NO: 37 | moltype = DNA length = 28 |
|---|---|
| FEATURE | Location/Qualifiers |
| misc_feature | 1..28 |
| | note = Primer sequence |
| source | 1..28 |
| | mol_type = other DNA |
| | organism = synthetic construct |

SEQUENCE: 37
tatggatgtt gtgatgaccc aatctcca          28

| SEQ ID NO: 38 | moltype = DNA length = 24 |
|---|---|
| FEATURE | Location/Qualifiers |
| misc_feature | 1..24 |
| | note = Primer sequence |
| source | 1..24 |
| | mol_type = other DNA |
| | organism = synthetic construct |

SEQUENCE: 38
ggccgctaac actctcccct gttg          24

| SEQ ID NO: 39 | moltype = DNA length = 27 |
|---|---|
| FEATURE | Location/Qualifiers |
| misc_feature | 1..27 |
| | note = Primer sequence |
| source | 1..27 |
| | mol_type = other DNA |
| | organism = synthetic construct |

SEQUENCE: 39
tatgcaggtc caactggtgc agtctgg          27

| SEQ ID NO: 40 | moltype = DNA length = 54 |
|---|---|
| FEATURE | Location/Qualifiers |
| misc_feature | 1..54 |
| | note = Primer sequence |
| source | 1..54 |
| | mol_type = other DNA |
| | organism = synthetic construct |

SEQUENCE: 40
agagccacct ccgcctgaac cgcctccacc tgggcatgat gggcatgggg gacc          54

| SEQ ID NO: 41 | moltype = DNA   length = 52 |
| --- | --- |
| FEATURE | Location/Qualifiers |
| misc_feature | 1..52 |
| | note = Primer sequence |
| source | 1..52 |
| | mol_type = other DNA |
| | organism = synthetic construct |

SEQUENCE: 41
ggcggaggtg gctctggcgg tggcggatcg tcaggcacta caaatactgt gg        52

| SEQ ID NO: 42 | moltype = DNA   length = 33 |
| --- | --- |
| FEATURE | Location/Qualifiers |
| misc_feature | 1..33 |
| | note = Primer sequence |
| source | 1..33 |
| | mol_type = other DNA |
| | organism = synthetic construct |

SEQUENCE: 42
ggccgctatt ctctgaattc ccctttctcc tgg        33

| SEQ ID NO: 43 | moltype = DNA   length = 40 |
| --- | --- |
| FEATURE | Location/Qualifiers |
| misc_feature | 1..40 |
| | note = Primer sequence |
| source | 1..40 |
| | mol_type = other DNA |
| | organism = synthetic construct |

SEQUENCE: 43
acaattcccc tctagatttt gtttaacttt aagaaggaga        40

| SEQ ID NO: 44 | moltype = DNA   length = 39 |
| --- | --- |
| FEATURE | Location/Qualifiers |
| misc_feature | 1..39 |
| | note = Primer sequence |
| source | 1..39 |
| | mol_type = other DNA |
| | organism = synthetic construct |

SEQUENCE: 44
caaaattatt tctagatttc gggctttgtt agcagccgg        39

| SEQ ID NO: 45 | moltype = DNA   length = 30 |
| --- | --- |
| FEATURE | Location/Qualifiers |
| misc_feature | 1..30 |
| | note = Primer sequence |
| source | 1..30 |
| | mol_type = other DNA |
| | organism = synthetic construct |

SEQUENCE: 45
catatgaacg tgcacgtgag cacagagtcc        30

| SEQ ID NO: 46 | moltype = DNA   length = 28 |
| --- | --- |
| FEATURE | Location/Qualifiers |
| misc_feature | 1..28 |
| | note = Primer sequence |
| source | 1..28 |
| | mol_type = other DNA |
| | organism = synthetic construct |

SEQUENCE: 46
ggatcctgag catatccctg catcctcc        28

| SEQ ID NO: 47 | moltype = DNA   length = 27 |
| --- | --- |
| FEATURE | Location/Qualifiers |
| misc_feature | 1..27 |
| | note = Primer sequence |
| source | 1..27 |
| | mol_type = other DNA |
| | organism = synthetic construct |

SEQUENCE: 47
catatgtatg gcaatgtgca cgccacc        27

| SEQ ID NO: 48 | moltype = DNA   length = 29 |
| --- | --- |
| FEATURE | Location/Qualifiers |
| misc_feature | 1..29 |
| | note = Primer sequence |
| source | 1..29 |
| | mol_type = other DNA |
| | organism = synthetic construct |

SEQUENCE: 48

```
ctcgagatcc acaggtgggc gattctggc                                              29

SEQ ID NO: 49          moltype = AA  length = 5
FEATURE                Location/Qualifiers
source                 1..5
                       mol_type = protein
                       organism = synthetic construct
SEQUENCE: 49
GGGGS                                                                         5

SEQ ID NO: 50          moltype = AA  length = 15
FEATURE                Location/Qualifiers
source                 1..15
                       mol_type = protein
                       organism = synthetic construct
SEQUENCE: 50
GGGGSGGGGS GGGGS                                                             15
```

THERAPEUTIC BIOLOGIC FOR TREATMENT OF HEPATOCELLULAR CARCINOMA

RELATED APPLICATIONS

This application is a Divisional of U.S. patent application Ser. No. 16/513,148, filed Jul. 16, 2019, now U.S. Pat. No. 11,485,771, which is a Divisional of U.S. patent application Ser. No. 15/270,430, filed Sep. 20, 2016, now U.S. Pat. No. 10,400,026, issued Sep. 3, 2019, which is a Divisional of U.S. patent application Ser. No. 14/539,577, filed Nov. 12, 2014, now U.S. Pat. No. 9,493,552, issued Nov. 15, 2016, which claims the benefit of U.S. Provisional Application No. 61/904,951, filed on Nov. 15, 2013. The entire teachings of the above applications are incorporated herein by reference.

INCORPORATION BY REFERENCE OF MATERIAL IN XML

This application incorporates by reference the Sequence Listing contained in the following extensible Markup Language (XML) file being submitted concurrently herewith:
 a) File name: 4261.1003-023_SL.xml; created Nov. 4, 2024; 63,662 Bytes in size.

BACKGROUND OF THE INVENTION

Primary liver cancer is the fifth most common cancer in men and the seventh in women worldwide. Globally, it is the second leading cause of cancer death in men and the sixth leading cause of cancer death among women. Hepatocellular carcinoma (HCC) accounts for 85% of primary liver cancer. HCC is endemic in southeast Asia and Sub-Saharan Africa. The incidence in western countries has increased in recent years and is expected to continue to increase. HCC is the fifth and the ninth leading cause of cancer deaths for men and women in the U.S. The 5 years overall survival for HCC is only 15%.

In view of the significant incidence of this disease, and its immense tolls on patients, their support systems and society at large, further improvement in treatment of HCC patients with intermediate and advance stage disease is urgently needed—more specifically, a need exists for agents that can specifically target HCC tumors and, e.g., reduce the volume of the tumors to treat the HCC and/or eliminate th tumors, as well as methods of making and using the same.

SUMMARY OF THE INVENTION

The invention provides, inter alia, agents that specifically target vascular endothelial cells of HCC tumors and treat the HCC, along with associated methods of using these agents. In a first aspect, the invention provides conjugates comprising a coagulating agent conjugated to an antibody, where the antibody specifically binds an extracellular domain epitope of a mammalian PLVAP protein.

In some embodiments, the coagulating agent is a coagulating protein. In more particular embodiments, the coagulating protein is a tissue factor. In still more particular embodiments, the tissue factor comprises an amino acid sequence at least about: 40, 45, 50, 55, 60, 65, 70, 75, 80, 85, 90, 95, 96, 97, 98, 99%, or more identical to SEQ ID NO: 1; e.g., at least 80, 85, 90, 95, 96, 97, 98, 99%, or more identical to SEQ ID NO: 1; e.g., at least 95, 96, 97, 98, 99%, or more identical to SEQ ID NO: 1.

In a related aspect, the invention provides conjugates comprising a tissue factor with an amino acid sequence at least 40, 45, 50, 55, 60, 65, 70, 75, 80, 85, 90, 95, 96, 97, 98, 99%, or more identical to SEQ ID NO: 1 conjugated, by a peptide bond, to an antibody, wherein the antibody specifically binds an epitope in an extracellular domain of a human PLVAP protein.

In any of the preceding aspects and embodiments, the mammalian PLVAP protein can comprise an amino acid sequence at least 50, 55, 60, 65, 70, 75, 80, 85, 90, 95, 96, 97, 98, 99%, or more identical to SEQ ID NO: 2; more preferably at least 80, 85, 90, 95, 96, 97, 98, 99%, or more identical to SEQ ID NO: 2; still more preferably at least 95, 96, 97, 98, 99%, or more identical to SEQ ID NO: 2.

For any of the preceding aspects and embodiments, the antibody can specifically bind an epitope selected from PPAGIPVAPSSG (SEQ ID NO: 25) or LAIRN-SALDTCIKTKSQPMMPVSRPM (SEQ ID NO: 26). In more particular embodiments, the antibody specifically binds the epitope PPAGIPVAPSSG (SEQ ID NO: 25).

For the conjugates of any of the preceding aspects and embodiments, in some embodiments, the coagulating protein and antibody are chemically cross-linked. In other embodiments, the coagulating protein and antibody are linked by a peptide bond.

In the conjugates of any one of the preceding aspects and embodiments, the antibody can be an immunoglobulin comprising a light chain variable region and a heavy chain variable region. In more particular embodiments, the coagulating protein and antibody are linked by a peptide bond between the carboxy terminus of a protein comprising the heavy chain variable region and the amino terminus of the coagulating protein. In other embodiments, the coagulating protein and antibody are linked by a peptide bond between the carboxy terminus of a protein comprising the light chain variable region and the amino terminus of the coagulating protein.

In some embodiments, in the conjugate of any one of the preceding aspects or embodiments, the coagulating protein and antibody are linked by a peptide bond by a linker peptide. In more particular embodiments, the linker peptide comprises $(Gly_4\text{-}Ser \text{ (SEQ ID NO: 49)})_n$, wherein n is 1, 2, 3, 4, 5, or 6; more preferably wherein n is 3.

In certain embodiments, the conjugate of any one of the preceding aspects or embodiments, the antibody is an immunoglobulin comprising:
 i) a heavy chain variable region comprising the CDRs of the variable region comprising the amino acid sequence of SEQ ID NO: 3 and a light chain variable region comprising the CDRs of the variable region comprising the amino acid sequence of SEQ ID NO: 4, optionally wherein the variable light chain and variable heavy chain have up to 1, 2, 3, or 4 conservative amino acid substitutions in each CDR; or
 ii) a heavy chain variable region comprising the CDRs of the variable region comprising the amino acid sequence of SEQ ID NO: 5 and a light chain variable region comprising the CDRs of the variable region comprising the amino acid sequence of SEQ ID NO: 6, optionally wherein the variable light chain and variable heavy chain have up to 1, 2, 3, or 4 conservative amino acid substitutions in each CDR.

In more particular embodiments, the light chain variable region and/or heavy chain variable region are humanized. In still more particular embodiments, the light chain variable region and heavy chain variable region are given by:

i) a heavy chain variable region selected from SEQ ID NO: 7, 8, 9, 10, or 11, more particularly wherein the heavy chain variable region is SEQ ID NO: 11; and a light chain variable region selected from SEQ ID NO: 12, 13, or 14, more particularly wherein the light chain variable region is SEQ ID NO: 13; or ii) a heavy chain variable region selected from SEQ ID NO: 15, 16, 17, 18, or 19, more particularly wherein the heavy chain variable region is SEQ ID NO: 19; and a light chain variable region selected from SEQ ID NO: 20, 21, or 22, more particularly wherein the light chain variable region is SEQ ID NO: 22.

In certain embodiments of any of the preceding aspects and embodiments, the conjugate comprises an amino acid sequence at least 80, 85, 90, 95, 96, 97, 98, 99%, or more identical to the amino acid sequence of SEQ ID NO: 23.

In a related aspect, the invention provides a nucleic acid encoding the conjugate of any one of the preceding aspects and embodiments. In a particular embodiment, the nucleic acids provided by the invention are contained in a vector. In a related embodiment, the vector can be in a host cell, and in certain embodiments, the host cell is a bacteria (such as, e.g., *Escherichia coli*). In other embodiments, the host cell is a eukaryotic cell (e.g., a fungus, such as yeast, including budding yeast; an insect cell, such as Sf0, Sf21, or high five cells; or mammalian cells, such as CHO, VERO, or COS cells).

In another related aspect, the invention provides pharmaceutical compositions comprising the conjugate of any of the preceding aspects and embodiments, wherein the composition further comprises a suitable carrier, excipient, or contrast medium. In more particular embodiments, the composition is in a dosage form suitable for administration to a subject.

In another aspect, the invention provides methods of making the conjugate of any one of the preceding aspects and embodiments by culturing the host cell of any one of the preceding aspects and embodiments under conditions that support the expression of the conjugate by the host and isolating the expressed conjugate.

In yet another embodiment, the invention provides methods of: treating a tumor with PLVAP-positive vasculature, treating hepatocellular carcinoma (HCC), reducing volume of a tumor with PLVAP-positive vasculature, or inducing thrombosis and tumor necrosis of a tumor with PLVAP-positive vasculature, in a mammalian subject in need thereof. In these methods, a therapeutically effective amount of the conjugate of any one of the preceding aspects and embodiments or a pharmaceutical composition of any one of the preceding aspects and embodiments are provided (e.g., administered, by any suitable means) to the subject (e.g., a human).

In some embodiments, the HCC tumor volume is reduced following thrombosis and tumor necrosis induced by the conjugate.

In certain embodiments, the conjugate is administered intravascularly to the tumor, e.g., HCC, of the subject. In more particular embodiments, the conjugate is infused directly into one or more tumor-feeding arteries.

In some embodiments, the subject is undergoing concurrent or sequential treatment with one or more chemotherapeutic agents, radio-therapy, intratumoral alcohol injection, surgery, cryotherapy, radio frequency ablation, or a combination of one or more of the foregoing. In more particular embodiments, the conjugate is administered to the subject together with one or more chemotherapeutic agents. In still more particular embodiments, the one or more chemotherapeutic agents comprise a therapeutically effective amount of sorafenib (see, e.g., PubChem 216239), bevacizumAb, or other antiangeogenic therapeutic drugs. In certain embodiments, the conjugate is administered to the subject in a pharmaceutical composition further comprising the one or more chemotherapeutic agents.

In some embodiments, the conjugate is administered at a dose of about 5 to about 200 µg/cm$^3$ of tumor, more particularly about 10 to about 150 µg/cm$^3$ of tumor, and more particularly about 15 to about 100 µg/cm$^3$ of tumor.

In certain embodiments, the conjugate is administered in a single dose. In other embodiments, the conjugate is administered in 2, 3, 4, 5, 6, 7, 8, 9, 10 doses, or more. In more particular embodiments, the doses are administered over a period of 1, 2, 3, 4, 5, 6, 7, 8, 9, or 10 days; or 1, 2, 3, 4, 5, or 6 weeks; or 1, 2, 3, 4, 5, or 6 months, or more.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings.

In FIG. 13A, appearance of fibrin thrombi (arrows) in blood vessels was noticed at 2 hours after infusion. The number of blood vessels containing fibrin thrombi became more prominent thereafter (arrows). No fibrin thrombi were observed in tumor blood vessels before treatment (0 hour). Tumor tissue became completely necrotic at 48 and 72 hours. Photomicrographs were taken at 100× magnification. In FIG. 13B, tumor cells show slight separation with increased clear space between each other at 4 hours after treatment. This change became more prominent at 24 hours. Frank necrosis with loss of blue nuclear staining became apparent 48 hours after treatment, and became more pronounced at 72 hours. The photomicrographs were taken at 200× magnification.

FIG. 19 is an annotated sequence of SEQ ID NO: 2, wherein the extracellular region of the complete NP_112600.1 (hPLVAP) is underlined.

FIG. 20 is an annotated sequence of SEQ ID NO: 3 >KFCC-GY4_VH_domain_4, wherein the CDRs are underlined.

FIG. 21 is an annotated sequence of SEQ ID NO: 4 >KFCC-GY4_VL_domain_9, wherein the CDRs are underlined.

FIG. 22 is an annotated sequence of SEQ ID NO: 5 >KFCC-GY5_VH_14, wherein the CDRs are underlined.

FIG. 23 is an annotated sequence of SEQ ID NO: 6 >KFCC-GY5_VL_19, wherein the CDRs are underlined.

FIG. 24 is an annotated sequence of SEQ ID NO: 23, the recombinant CSR02-Fd-TF insert, wherein the VH domain of Fd (1-114) is underlined, the CH1 domain of Fd (115-216) is bolded, the hinge (217-225) is double-underlined, the linker (226-239) is represented by lowercase letters, and the extracellular domain of human tissue factor (240-458) is italicized.

DETAILED DESCRIPTION OF THE INVENTION

Figure 1:
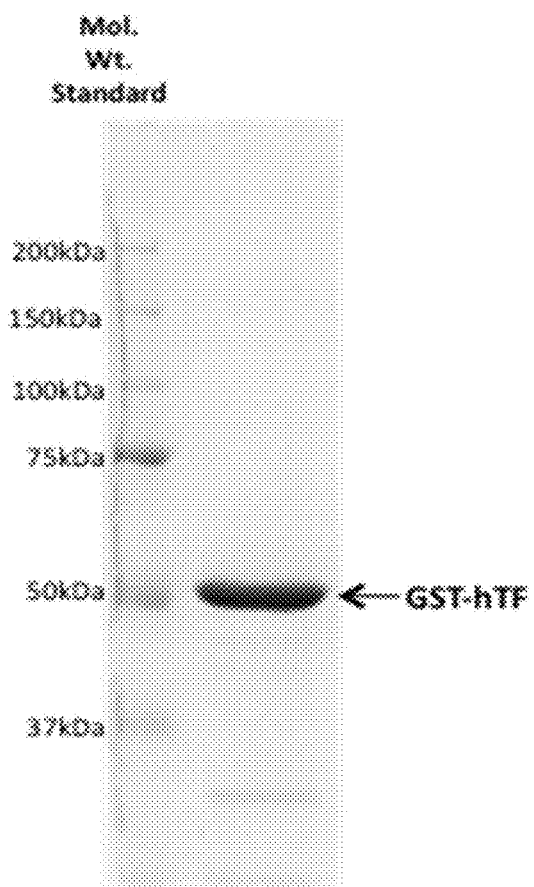
FIG. 1 is a picture of an electrophoretic gel, which shows SDS-PAGE analysis of purified GST-tagged human tissue factor protein. Ten percent polyacrylamide gel was used. Three micrograms of recombinant human tissue factor tagged with GST (GST-hTF) was loaded on the gel.

A description of example embodiments of the invention follows. Definitions of certain terms will be adhered to throughout the application.

Conjugates and Compositions Provided by the Invention

The invention provides conjugates comprising a coagulating agent conjugated to an antibody, where the antibody specifically binds an extracellular domain epitope of a mammalian PLVAP protein. Such conjugates are referred to as "conjugate(s) provided by the invention," "conjugate(s) of the invention," and the like, while compositions containing them, such as pharmaceutical compositions, are known as "composition(s) provided by the invention" and the like. The application may also refer to "conjugates(s) and composition(s) provided by the invention" to describe "conjugate(s) provided by the invention" and "composition(s) provided by the invention."

A "coagulating agent" promotes the formation of a thrombus in vivo in the circulatory system of a mammal, i.e., in the presence of a functional coagulation cascade and platelet activation pathway. A peptide "coagulating agent" is a "coagulating protein." Exemplary elements of the coagulation cascade include, e.g., Tissue factor, Hageman factor (human GeneID No. 2161), plasma thromboplastin (human GeneID No. 2160), thrombin (human GeneID No. 2147), Christmas factor (human GeneID No. 2158), stable factor VII (human GeneID No. 2155), and fibrin stabilizing factor (human GeneID Nos. 2162, 2165); see also human GeneID Nos. 2156, 2157, and 2159. Exemplary elements of the platelet activation pathway include, e.g., ADP, serotonin, platelet-activating factor (PAF; human GeneID No. 7941), Von Willebrand factor (vWF; human GeneID No. 7450), platelet factor 4 (human GeneID No. 5196), and thromboxane $A_2$ ($TXA_2$)). The coagulating agent can be a component or product of the coagulation cascade (i.e., a component of the intrinsic, extrinsic, or common pathway) or platelet activation pathway, as well as heterologous proteins, including coagulating venoms, such as convulxin (see, e.g., uniprot IDs 093426 and 093427 for reference protein sequences for the α and β subunits, respectively) and Russellysin (see, e.g., uniprot Q7LZ61), provided that the agent promotes thrombogenesis, e.g., in the presence of a functional coagulation cascade and platelet activation pathway.

In particular embodiments, the coagulating agent is a coagulating protein. The coagulating protein can be in the conjugate as a monomer, or an oligomer, such as a dimer, or trimer; or a polymer of higher order structure. In more particular embodiments, the coagulating protein is a tissue factor. A "tissue factor," also known as factor III, thromboplastin, and CD142, is a receptor for factor VII that promotes thrombogenesis. A tissue factor is exemplified by human GeneID No. 2152, and numerous homologues are known (see HomoloGene ID 1511), including proteins from human: NP_001984.1, mouse: NP_034301.3, chimp: XP_001156450.1, and dog NP_001019811.1. The human protein includes motifs such as a pair of fibronectin type 3 domains (c100065) conserved amongst homologues, as well as a pair of WKS motifs (Uniprot P13726.1), and an interferon-binding region (conserved domain CDD: 204189). In particular embodiments, the tissue factor is a soluble, extracellular portion of tissue factor, exemplified by SEQ ID NO: 1, which is amino acid 33-251 of NP_001984.1, and corresponding sequences as identifiable by alignments with homologous sequences from other organisms, as well as functional variants thereof, including substitutions and truncations (e.g., of 1, 2, 3, 4, 5, 6, 7, 8, 9, 10 residues, or more). In some embodiments the tissue factor comprises an amino acid sequence at least 40, 45, 50, 55, 60, 65, 70, 75, 80, 85, 90, 95, 96, 97, 98, 99%, or more identical to SEQ ID NO: 1; more preferably at least 80, 85, 90, 95, 96, 97, 98, 99%, or more identical to SEQ ID NO: 1; still more preferably at least 95, 96, 97, 98, 99%, or more identical to SEQ ID NO: 1. Variant tissue factors, with altered levels of activity, can be used in the invention as well, either as monomers, or, in some embodiments, multimers, such as dimers. These include the "coagulation-deficient" tissue factor, as described in U.S. Pat. No. 6,156,321, incorporated by reference in its entirety, which are 100-fold, or more, less active than native tissue factor, e.g., with regard to activating Factor VII.

"Antibody" encompasses both immunoglobulins (as well as antigen-binding fragments thereof) and non-immunoglobulin scaffolds that can be adapted and used similar to immunoglobulins—so-called antibody-mimetics. Exemplary antibody mimetics include those based on fibronectin 3 domains (Fn3 domains; also known as monobodies; see, e.g., Koide and Koide, *Methods Mol. Biol.* 352: 95-109) (2007)), Z domains of protein A (also known as affibodies; see, e.g., Nygren *FEBS J.* 275 (11): 2668-76 (2008), gamma-B crystalline or ubiquitin (affilins; see, e.g., Ebersbach, et al. *J. Mol. Biol.* 372 (1): 172-85 (2007)), lipocalins (anticalins; see, e.g., Skerra, *FEBSJ,* 275 (11): 2677-83 (2008)); A domains of membrane receptors (avimers; see, e.g., Silverman, et al. *Nat. Biotechnol.* 23 (12): 1556-61 (2005)); ankryn repeats (darpins; see, e.g., Stumpp et al., *Drug Discov. Today* 13 (15-16): 695-701 (2008)); SH3 domain of Fyn (fynomers; see, e.g., Grabulovski et al., *J Biol Chem* 282 (5): 3196-3204(2007)), and Kunitz type domains (Kunitz domain peptides; see, e.g., Nixon and Wood C R, *Curr Opin Drug Discov Devel* 9 (2): 261-8 (2006)).

Antibodies for use in the conjugates provided by the invention specifically bind an extracellular domain epitope of a mammalian PLVAP protein. Exemplary extracellular domain epitopes of a mammalian PLVAP include regions corresponding to (e.g., as evaluated by sequence alignments, such as BLASTp, ClustalW, COBALT, et cetera, using default parameters) to the extracellular domain of a PLVAP (from about amino acid 49 and on in SEQ ID NO: 2), or, more particularly, in the C-terminus of PLVAP, such as: from about amino acid 238 and on in SEQ ID NO: 24 (NP_115774.2, the mouse PLVAP reference sequence, e.g., such as a peptide consisting of the amino acid sequence of amino acids 238-413 of SEQ ID NO: 24), or sequences contained in about amino acid 370 to about 442 of SEQ ID NO: 2, (the human PLVAP reference sequence, NP_112600.1), such as amino acids 378 to 404 of SEQ ID NO: 2 or amino acids 431 to 442 of SEQ ID NO: 2. In particular embodiments, the antibodies for use in the conjugates provided by the invention specifically bind to an epitope in amino acids 378 to 404 of SEQ ID NO: 2 or amino acids 431 to 442 of SEQ ID NO: 2; and/or a corresponding primate homologue of either of these, such as corresponding sequences from *Macaca fascicularis* (XP_005588437.1) and *Macaca mulatta* (AFH29537.1).

In particular embodiments, the antibody is an immunoglobulin. "Immunoglobulin" refers to both full-length immunoglobulins, as well as antigen-binding fragments of immunoglobulins, such as Fab, F(ab')2, Fv, scFv, Fd, dAb, and other immunoglobulin fragments that retain antigen-binding function. Immunoglobulins will have at least 3 CDRs (complementarity determining regions) in their antigen-binding domain, and, in more particular embodiments, 4, 5,or 6 CDRS, and still more particularly, 6 CDRs in an antigen-binding domain. Immunoglobulins for use in the invention include, for example, human, orangutan, mouse, rat, goat, sheep, rabbit and chicken antibodies. Immunoglobulins may be polyclonal, monoclonal, monospecific, polyspecific, non-specific, humanized, camelized, single-chain, chimeric, synthetic, recombinant, hybrid, mutated, or CDR-grafted. Particular immunoglobulins for use in the invention include those with the CDRs of the antibodies produced by murine hybridoma KFCC-GY4 (ATCC® Patent Deposit Designation PTA-9963) or murine hybridoma KFCC-GY5 (ATCC® Patent Deposit Designation PTA-9964), or conservative substitutions thereof, e.g., in particular embodiments, with up to about: 1, 2, 3, 4, 5, 6, 7, 8, 9, 10, 11, 12, 13, 14, 15, 16, 17, or 18 conservative amino acid substitutions (more particularly 1, 2, 3, 4, 5, or more substitutions) in the antigen-binding domain, e.g., up to about: 1, 2, 3, or 4 conservative substitutions in each CDR; more particularly up to 1 or 2 conservative substitutions in each CDR. In certain embodiments, the immunoglobulin comprises humanized heavy and light variable domains. The KFCC-GY4 and KFCC-GY5 antibodies, including the amino acid sequences of their variable domains and CDRs are described in U.S. Patent Application Publication Nos. US 2011/0085973 (first describing the monoclonal antibodies, which were generated in mouse) and US 2011/0262349 (describing particular chimeric and humanized variants), both of which are incorporated by reference in their entirety. See also SEQ ID NOs: 3-22, providing variable domain sequences, and identified CDRs for these antibodies.

"PLVAP," also known as plasmalemma vesicle associated protein, PV1, FELS, and gp68, is a protein expressed in tumor vasculature, such as HCC tumor vasculature, and is described in human GeneID No. 83483. PLVAPs have been identified in several organisms (see HomoloGene ID 10578), such as: human (NP_112600.1, see also SEQ ID NO: 2), chimp (XP_512490.3), mouse (NP_115774.2), and dog (XP_541953.3) and comprise a PV-1 domain (pfam06637). Antibodies that specifically bind a PLVAP, such as a mammalian PLVAP, in some embodiments, bind an extra cellular domain of PLVAP, which corresponds to approximately amino acids 49-442 or 51-442 of SEQ ID NO: 2. In particular embodiments, the mammalian PLVAP comprises an amino acid sequence at least 50, 55, 60, 65, 70, 75, 80, 85, 90, 95, 96, 97, 98, 99%, or more identical to SEQ ID NO: 2 (or an extracellular domain thereof); more preferably at least 80, 85, 90, 95, 96, 97, 98, 99%, or more identical to SEQ ID NO: 2 (or an extracellular domain thereof); still more preferably at least 95, 96, 97, 98, 99%, or more identical to SEQ ID NO: 2 (or an extracellular domain thereof). In some embodiments, the PLVAP protein includes substitutions (e.g., of 1, 2, 3, 4, 5, residues or more) and/or truncations (e.g., of 1, 2, 3, 4, 5, 6, 7, 8, 9, 10 residues, or more), relative to SEQ ID NO: 2, or an extracellular domain thereof.

A linker peptide for use consonant with the invention can couple the antibody and coagulating agent, e.g., coagulating protein, by a peptide bond—e.g., the antibody (e.g., one of the variable domains of an immunoglobulin) and coagulating protein can be expressed as a single polypeptide chain. The linker peptide can vary in length from, e.g., about: 3, 4, 5, 6, 7, 8, 9, 10, 15, 20, 25, 30, 35, 40, 45, or 50 amino acids, or more, e.g., about: 75, 100, 150, 200, 250, or 300amino acids. In some embodiments, the linker comprises a hinge region, analogous to the cysteine-rich and proline-rich domains found in naturally-occurring immunoglobulins, and optionally including a further linker peptide, such as (Gly$_4$-Ser)$_3$(SEQ ID NO: 50), to space the antibody (e.g., immunoglobulin) and coagulating agent (e.g., coagulating protein).

Conjugates provided by the invention can optionally comprise a label, such as a detectable label, such as a fluorescent, enzymatic, or radio label. In certain embodiments, the conjugate provided by the invention is biotinylated.

In a related aspect the invention provides nucleic acids encoding the conjugates provided by the invention, vectors containing the nucleic acids, and host cells containing the nucleic acids and vectors. Exemplary nucleic acids include those encoding proteins at least 80, 85, 90, 95, 96, 97, 98, 99%, or more identical to a conjugate provided by the invention, including, in particular embodiments, the conjugate having the amino acid sequence of SEQ ID NO: 23. In other embodiments, the nucleic acid can hybridize under highly stringent hybridization conditions to a nucleic acid encoding a conjugate provided by the invention. "Highly stringent hybridization" conditions are: at least about 6× SSC and 1% SDS at 65° C., with a first wash for 10 minutes at about 42° C. with about 20% (v/v) formamide in 0.1× SSC, with a subsequent wash with 0.2×SSC and 0.1% SDS at 65° C. In particular embodiments, a nucleic acid provided by the invention can be codon modified, e.g., for the particular host cell used for production of the conjugate. Vectors encoding a nucleic acid provided by the invention can contain additional sequences required for, e.g., expression of a conjugate provided by the invention (such as regulatory sequences, promoters, and enhancers) as well as certain suitable ancillary sequences, such as one or more replication origins, one or more selectable markers, and integration sequences (e.g., for integration into a host genome, either by random integration, transposable elements, or site specific integration, e.g., by homologous recombination, such as by targeted nucleases).

In related aspects, the invention provides methods of making the conjugates provided by the invention, e.g., by culturing a host cell containing a nucleic acid provided by the invention under conditions that support the expression of the conjugate by the host (e.g., if a promoter is inducible, by adding the inducing agent, et cetera), and then isolating the expressed conjugate. Suitable hosts include bacteria (e.g., *Escherichia coli*) as well as eukaryotic cells, such as a fungus, such as yeast, including budding yeast; an insect cell, such as Sf0, Sf21, or high five cells; or mammalian cells, such as CHO, VERO, or COS cells, or mesenchymal stem cells (MSCs).

The conjugates provided by the invention can usefully be formulated in compositions, such as pharmaceutical compositions—e.g., where a conjugate provided by the invention is compounded with a suitable carrier or excipient. Any suitable pharmaceutical carrier can be used in the invention. In particular embodiments, the carrier will promote the stability of the conjugate, e.g., when lyophilized for storage or transportation, and support the stability of the conjugates provided by the invention when in a solution, such as an aqueous solution after reconstitution, consistent with best pharmaceutical practices. Pharmaceutical compositions can include one or more of: a buffer (such as a histidine, phosphate, or succinate buffer), a bulking or caking agent (such as glycine or sorbitol, or a sugar, such as sucrose, dextrose, lactose, or fructose), a tonicity modifier (such as an inorganic salt, such as sodium chloride, potassium phosphate, or sodium phosphate), a preservative, wetting agents, emulsifiers, et cetera.

In particular embodiments, the conjugates provided by the invention are formulated in a pharmaceutical composition suitable for direct administration to HCC tumor vasculature, e.g., through transvascular administration, such as transarterial administration. In particular embodiments, the conjugates provided by the invention can be formulated in a lipidol oil. In other embodiments, the conjugates provided by the invention can be formulated with microparticles with an average diameter of between about 45 μm and about 90 μm, such as IVALON® embolic particles. Injection with presence of such excipients may increase the availability of the conjugates provided by the invention, when administered to the treated tumors, e.g., by inducing stasis of blood within tumor blood vessels after injection.

In some embodiments, the compositions provided by the invention can include a compatible water-soluble contrast medium (for radiographic, MRI, or ultrasound applications) to, for example, allow assessment of the distribution of the conjugate provided by the invention in the treated tumors by fluoroscopy and/or to assess the completeness of a tumor exposed to the conjugates provided by the invention.

The pharmaceutical compositions provided by the invention can be prepared in dosage form(s) for distribution and administration to a subject in need thereof (consonant with the methods provided by the invention), including kits of multiple dosage forms, which can contain one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, that notice reflects approval by the agency of manufacture, use of sale for human administration. The pack or kit can be labeled with information regarding mode of administration, sequence of drug administration (e.g., separately, sequentially or concurrently in the case of multi-agent kits), or the like. The pack or kit may also include means for reminding the patient to take the therapy. The pack or kit can be a single unit dosage of the combination therapy or it can be a plurality of unit dosages. In particular, the compound(s) can be separated, mixed together in any combination, present in a single form, e.g., vial or tablet. For the purpose of this invention, unit dosage is intended to mean a dosage that is dependent on the individual pharmacodynamics of each compound and administered in FDA approved dosages in standard time courses.

The conjugates provided by the invention, the pharmaceutical compositions provided by the invention, and kits provided by the invention containing them therefore are useful in methods of treating a subject with a tumor with PLVAP-positive vasculature, such as HCC, as well as methods of visualizing a tumor with PLVAP-positive vasculature.

Treatment Methods

The conjugates and compositions provided by the invention can be used in methods of, for example: treating a tumor with PLVAP-positive vasculature (such as HCC or glioblastoma), treating hepatocellular carcinoma (HCC), reducing tumor volume of a tumor with PLVAP-positive vasculature, or inducing thrombosis and tumor necrosis of a tumor with PLVAP-positive vasculature, in a mammalian subject in need thereof. These methods comprise administering a therapeutically effective amount of the conjugates provided by the invention or compositions provided by the invention to the subject.

A "subject" refers to a mammal, more particularly, a human patient (male or female), and in more particular embodiments, a human patient with HCC, glioblastoma, or any tumor with PLVAP-positive vasculature. While subjects may be of any stage of life and any age, e.g., neonate, infant, toddler, child, young adult, adult, or geriatric; in particular embodiments the subject is an adult, e.g., a human adult, i.e., about 18 years old, or older, e.g., about:18-70, 20-60, 25-55, 25-50, 30-50, 25-65 years old, as well as greater than about: 30, 40, 50, 60, 70, 80 or 90 years old. In more particular embodiments, the subject is 60 years old, or older, such as, more particularly, 65 years old, or older. In still more particular embodiments, the subject is between about 70 and about 79 years old.

As used herein, the terms "treat," "treating," or "treatment" mean to counteract a medical condition (e.g., HCC or a tumor with PLVAP-positive vasculature) so that the medical condition is improved according to a clinically-acceptable standard. For example, an improvement in HCC includes reduced tumor volume, reduced tumor blood flow, tumor necrosis and/or apoptosis, normalized hepatic function, et cetera.

A "therapeutically effective amount" is an amount sufficient to achieve the desired therapeutic or prophylactic effect under the conditions of administration, such as an amount sufficient to treat HCC. The effectiveness of a therapy can be determined by one skilled in the art using standard measures and routine methods. In particular embodiments, the conjugate is administered at a dose of about 5 to about 200 µg/cm$^3$ of tumor, more particularly about 10 to about 150 µg/cm$^3$ of tumor, and more particularly about 15 to about 100 µg/cm$^3$ of tumor. Dosages found to be effective in one organism, such as the mouse examples provided herein, can be converted for use in another organism, such as humans, using known methodologies. See, e.g., Reagan-Shaw et al., *FASEB J.* 22:659-61 (2008); Schein et al., *Clin. Pharmacol. Ther.* 11: 3-40 (1970); and Freireich et al., *Cancer Chemother. Reports* 50(4):219-244 (1966). For example, human equivalent dosing (HED) in mg/kg based on animal dosing can be given by the following equation: HED (mg/kg)=animal dose (mg/kg)×(Km$^{animal}$/Km$^{human}$), where Km=weight/surface area (kg/m$^2$). Exemplary conversion factors based on the above equation are shown in Table A.

TABLE A

| To: | From: | | | | |
|---|---|---|---|---|---|
| | Mouse (20 g) | Rat (150 g) | Monkey (3.5 kg) | Dog (8 kg) | Human (60 kg) |
| Mouse | 1 | 0.5 | 0.25 | 0.17 | 0.08 |
| Rat | 2 | 1 | 0.5 | 0.25 | 0.14 |
| Monkey | 4 | 2 | 1 | 0.6 | 0.33 |
| Dog | 6 | 4 | 1.7 | 1 | 0.5 |
| Human | 12 | 7 | 3 | 2 | 1 |

The conjugates provided by the invention and compositions provided by the invention can be provided (e.g., administered) to the subject by any suitable means, including, in particular embodiments, intravascularly to the tumor of the subject, e.g., the conjugate is infused directly into one or more tumor-feeding vessels of the HCC.

Subjects treated by the methods provided by the invention may be undergoing concurrent or sequential treatment with: one or more chemotherapeutic agents, radio-therapy, intratumoral alcohol injection, surgery, cryotherapy, radio frequency ablation, or a combination of one or more of the foregoing. In certain embodiments, the one or more chemotherapeutic agents include a therapeutically effective amount of sorafenib (see, e.g., PubChem 216239), bevacizumAb, or other antiangeogenic therapeutic drugs. For combination methods, the conjugate provided by the invention (or composition provided by the invention) can be administered concurrently (either in a single composition or in separate compositions) or sequentially (either before or after the other treatment).

Where the method employs a composition provided by the invention that includes a contrast agent, the methods provided by the invention can, in some embodiments, include the step of visualizing the tumor (e.g., HCC or glioblastoma) using the contrasting agent, e.g., by x-ray (including CAT scan), MRI, or ultrasound.

Subjects can be administered the conjugates or compositions provided by the invention in a single dose or, in other embodiments, in multiple doses, e.g., in 2, 3, 4, 5, 6, 7, 8, 9, 10 doses, or more. When administered multiple doses, the doses can be administered over a period of 1, 2, 3, 4, 5, 6, 7, 8, 9, or 10 days; or 1, 2, 3, 4, 5, or 6 weeks; or 1, 2, 3, 4, 5, or 6 months.

High risk groups for developing HCC can include subjects that: are HBV-positive; are HCV-positive; have impaired liver function; have liver cirrhosis; have mutations in one or more of TP53 (OMIM 191170), MET (OMIM 164860), CTNNB1 (OMIM 116806), CASP8 (OMIM 601763), PIK3CA (OMIM 171834), AXIN1 (OMIM 603816), PDGFRL (OMIM 604584), and APC (OMIM 611731); alpha-1-antitrypsin deficiency (OMIM 613490); hemochromatosis (OMIM 235200); tyrosinemia (OMIM 276700); and combinations of the foregoing. Accordingly, in certain embodiments, the methods provided by the invention entail the step of providing a subject with (or suspected of having) HCC, who has one or more of these mutations, e.g., the subject is identified as having one of the mutations (or any mutation that is associated with increased pathogenicity of the HCC) before administration of the conjugate provided by the invention.

The conjugates provided by the invention and compositions provided by the invention can be administered to the subject (such as a human) by any suitable route and by any suitable means. For example, the conjugate or composition can be administered intravascularly to the HCC of the subject, e.g., by infusion directly into one or more tumor-feeding vessels, such as a hepatic artery or a femoral artery or through the hepatic portal vein. The conjugates provided by the invention and compositions provided by the invention can be administered to the subject alone or together (either in the same composition, or concurrent or sequential administration) with one or more chemotherapeutic agents, such as one or more of sorafenib (see, e.g., PubChem 216239), bevacizumAb, or other antiangeogenic therapeutic drugs.

In any of the methods provided by the invention the conjugate is administered at a dose of about 5 µg/cm$^3$ of tumor to about 200 µg/cm$^3$ of tumor, more particularly about 10 to about 150 µg/cm$^3$ of tumor, and more particularly about 15 to about 100 µg/cm$^3$ of tumor. The conjugates provided by the invention or compositions provided by the invention can be administered in a single dose, or in multiple doses, such as 2, 3, 4, 5, 6, 7, 8, 9, 10 doses, or more. Multiple does can be over any useful period, such as 1, 2, 3, 4, 5, 6, 7, 8, 9, or 10 days; or 1, 2, 3, 4, 5, or 6 weeks; or 1, 2, 3, 4, 5, or 6 months.

Exemplification

PLVAP gene expression is restricted to vascular endothelial cells of HCC and not in non-tumorous liver tissue. PLVAP protein is a structural protein of vascular endothelia fenestrae and caveolae. It is not known to be involved in signaling. Anti-PLVAP antibody treatment was recently reported to affect leukocyte trafficking crossing vascular endothelial cells in mice.

In this patent application, we describe the development of a novel therapeutic biologic for treatment of HCC by exploiting differential expression of PLVAP in vascular endothelial cells of HCC not in non-tumorous liver tissue. For our approach, we develop this therapeutic biologic by co-expressing human tissue factor protein on anti-PLVAP antibody or its Fab fragment. Human tissue factor is a potent trigger of blood coagulation. Infusion of such a therapeutic agent developed by us into blood vessels of HCC can lead to its binding to tumor vascular endothelial cells and trigger blood clot formation in all blood vessels of HCC. The thrombosis of HCC tumor blood vessels leads to deprivation of tumor blood supply and ischemic necrosis. Using a HCC xenograft model in SCID mice, we showed that infusion into tumor feeding artery of the developed anti-PLVAP monoclonal antibody, or its Fab fragment, with human tissue factor successfully induced massive ischemic necrosis of the tumor xenografts and suppressed tumor growth. Systemic administration of such a therapeutic agent through a peripheral vein was ineffective. Thus, infusion of this novel agent into tumor feeding arteries is preferred to achieve therapeutic effect.

Materials and Methods

Rat Anti-Mouse PLVAP MECA32 Monoclonal Antibody (mAb)

MECA 32 hybridoma was obtained from Developmental Studies Hybridoma Bank at University of Iowa (Iowa City, IA). The hybridoma cells were cultured in RPMI medium containing 10% low-IgG fetal bovine serum, 1% GLUTA-MAX™ supplement (Life Technologies, Carlsbad, CA), 1% Antibiotics-antimycotics (Life Technologies) and 1% HEPES (Life Technologies). Rat anti-mouse PLVAP MECA32 mAb was purified from thick culture supernatant of MECA 32 hybridoma cells using HiTrap® Protein G column from GE Healthcare Life Sciences according to the instruction of the manufacturer. The purified antibody was dialyzed into phosphate buffered saline (PBS), pH 7.4. The concentration of antibody was determined by absorbance at 280 nm wave length using extinction coefficient of 1.37 for 1 mg/ml.

Production of Water-Soluble Extracellular Domain of Human Tissue Factor Protein

To produce recombinant water soluble extracellular portion of human tissue factor protein (hTF), a PCR fragment for the extracellular domain of human tissue factor cDNA (amino acid residues 33 to 251) was prepared from a full length cDNA clone of human tissue factor (NM001993.2) (OriGene Corp., Rockville, MD). Primers used for PCR contained restriction sequences for BamH1 and Sal1 at the 5' end of both forward and backward primers, respectively. The amplified cDNA fragment was inserted into pGEX®-6P-1 plasmid (GE Healthcare Life Sciences) and tagged with glutathione transferase (GST). The expression construct described above was verified by DNA sequencing and transformed into *Escherichia coli* strain SHuffle™ T7 Express (New England Biolabs, Inc. Ipswich, MA) for production of hTF. The *E. coli* transformants were plated on selective medium. Later, a colony of 1-2 mm was selected randomly and inoculated into 4 ml of 2xYT medium containing 100 μg/ml ampicillin at 30° C. and incubated in a 230 rpm incubator shaker overnight. The following day, the overnight culture was inoculated into 400 ml of 2xYT medium containing 100 μg/ml ampicillin and continued to grow at 30° C. in a 230 rpm incubator shaker overnight. When the absorbance at 600 nm reached about 0.6~0.8, Isopropyl β-D-1-thiogalactopyranoside (IPTG) was added to a final concentration of 0.4 mM to induce protein production. Shaking was continued at 30° C. for about 20 hours. Following the induction with IPTG, the cells were harvested by centrifugation (10,000 x g; 20 min) and subjected to lysis in 1x PBS with 0.2% TWEEN® 80 detergent containing lysozyme and Benzonase® Nuclease (Novagen) at room temperature for 2 hours. Cell lysate was centrifuged at 10,000 rpm for 30 minutes at 4° C. Supernatant was collected and filtered as soluble fraction.

The recombinant human tissue factor tagged with GST (GST-hTF) was purified from GSTrap™ FF column (GE Healthcare Life Sciences, Piscataway, NJ) according to the instruction of the manufacturer. The eluted fractions containing the GST-hTF were identified with SDS-polyacrylamide gel electrophoresis (SDS-PAGE), pooled and dialyzed into PBS. The concentration of the purified protein was determined using Bradford protein assay (Bio-Rad laboratories, Hercules, CA) and bovine serum albumin as standard. The purified GST-hTF showed a protein band with expected molecular weight of 50 kDa in SDS-PAGE gel (10% polyacrylamid) (FIG. 1). The tissue factor activity of the purified protein was assayed against a commercial human tissue factor using a chromogenic assay. The purified GST-hTF was assayed against a commercial hTF standard and had hTF activity of 3 ug per microgram protein. The procedure of this hTF activity assay is detailed in a later section.

Figure 2:
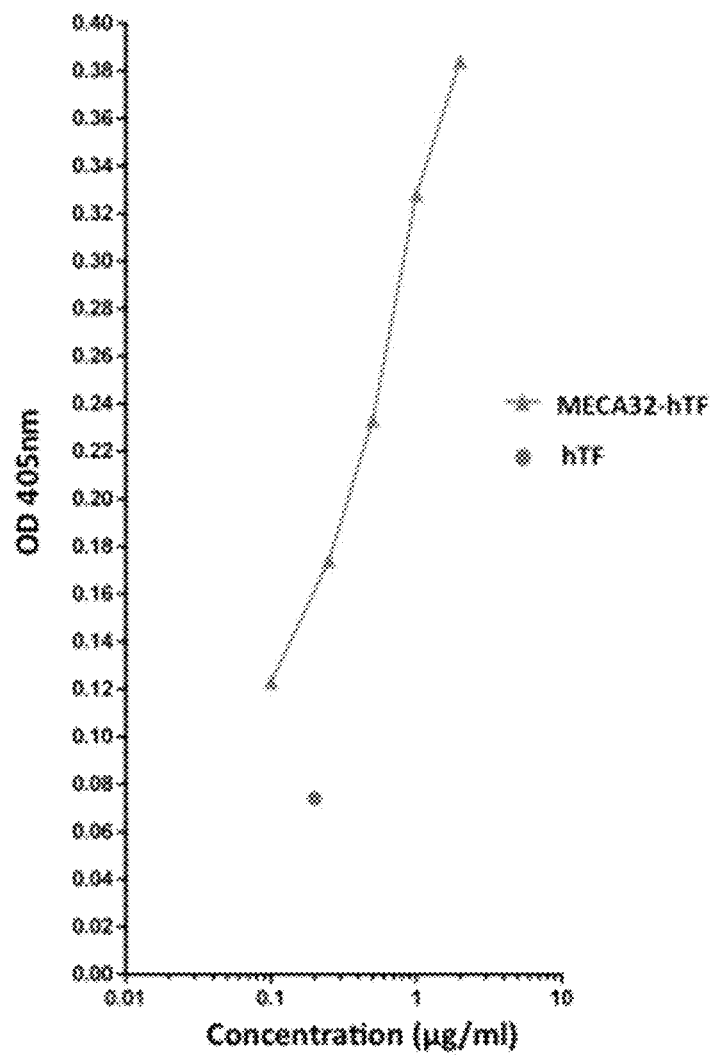
FIG. 2 is a graph of OD405nm as a function of protein concentration, illustrating the binding of MECA32 chemically conjugated with human tissue factor (MECA32-hTF) to human PLVAP by enzyme-linked immunoassay. Each well of the assay plate was coated with water soluble extracellular domain of mouse PLVAP protein. After blocking, the coated wells were incubated with increasing concentrations of MECA32-hTF. One well was incubated with human tissue factor (hTF). Binding of MECA32-hTF to PLVAP was detected with biotinylated anti-hTF antibody from R&D Systems, Inc. (Minneapolis, Minn.) and strepavidin-alkaline phosphotase conjugate from Thermo Scientific, Inc. (Rockford, Ill.). The result showed that MECA32-hTF bound to mouse PLVAP and carried hTF detectible with anti-hTF antibody. Control soluble hTF without antibody (solid circle) could not bind to PLVAP and be detected.

Conjugation of Recombinant GST-hTF to Rat Anti-Mouse PLVAP MECA32 Monoclonal Antibody First, the purified MECA32 mAb was dialyzed in 0.1 M IVIES buffer containing 0.5M NaCl at pH 6.0. IVIES is 2-(N-morpholino) ethanesulfonic acid. The antibody was adjusted to 1 mg/ml using the same IVIES buffer. To 1 ml of MECA32 mAb, 1.2 mg EDC (1-Ethyl-3-[3-dimethylaminopropyl]carbodiimide hydrochloride) and 3.3 mg of sulfo-NHS (N-hydroxysulfosuccinimide) were added. After gentle vortexing to dissolve the added reagents, the mixture was incubated at room temperature for one hour. Zeba desalting column pre-equilibrated with PBS coupling buffer was used to recover activated MECA32 mAb. PBS coupling buffer consisted 140 mM NaCl, 10 mM sodium phosphate and 3 mM KCl at pH 7.4-7.5. Next, the equal number of GST-hTF (0.33mg in 0.66 ml) was added to the activated MECA32-mAb. The mixture was incubated on a rotary mixer for 3 hours at room temperature. The reaction was then quenched by addition of hydroxylamine to a final concentration of 10 mM. The antibody conjugated with human tissue factor protein was dialyzed against 1x phosphate buffered saline extensively to remove all small organic chemicals. The concentration of antibody was determined by absorbance at 280 nm. The extinction coefficient of 1.37 for 1 mg/ml was used for determination of antibody concentration. The antibody conjugated with human tissue factor was measured for the tissue factor activity using a chromogenic assay. The recombinant human tissue factor purchased from R&D Systems (Minneapolis, Minn.) was used as a standard for the assay. The purified TF conjugate of MECA32 monoclonal antibody (MECA32-TF) was assayed for binding to mouse PLVAP and the presence of human tissue factor on the antibody bound to mouse PLVAP (FIG. 2).

Development of a plasmid construct to express Fab fragment of MECA32 anti-mouse PLVAP monoclonal antibody co-expressing hTF (MECA32-Fab-TF)

Preparation of a plasmid construct to produce MECA32-Fab-TF was accomplished in four steps. The first step was to prepare cDNAs of variable domain of MECA32 mAb light chain (VL) and variable domain of MECA32 mAb heavy chain (VH), and determine their DNA sequences for preparation of primers to be used in the second step. The second step was to prepare full length cDNA for kappa light chain of MECA32 mAb with a His-tag at the carboxyl terminus, and inserted into pET26b plasmid vector. The third step was to prepare a cDNA of VH1 and CH1 domains (Fd) plus hinge region of MECA32 mAb heavy chain with a linker sequence at the 3' end, and cDNA for hTF and a linker sequence at the 5' end. The overlapping PCR was then used to stitch two cDNAs together. This cDNA of MECA32-Fd-hinge-linker-TF was inserted into pET26b plasmid vector. The fourth step was to construct a bicistronic plasmid vector from the plasmids prepared from the second and the third steps. These four steps are described in more details below and summarized in FIGS. 3A and 3B.

First Step: Cloning cDNAs of VL Domain of MECA32 mAb Kappa Light Chain and VH Domain of MECA32 mAb Heavy Chain for Nucleic Acid Sequencing The cDNAs coding variable domains of MECA32 mAb light chain (VL) and heavy chain (VH) were prepared using FirstChoice® RLM-RACE kit (Ambion, Inc., Austin, TX) according to manufacturer's instruction. Briefly, total RNA isolated from MECA32 hybridoma was used as template to amplify variable domain of light (VL) and heavy chains (VH) by reverse transcription PCR using primers complementary to the nucleotide sequences of the constant domain of the kappa light chain next to VL domain (5' TGTCCTGATCAGTAACACTGTCC3') (SEQ ID NO: 27) and CHI domain of the heavy chain next to VH domain (5'TGAGAGTGTAGAGTCCAGACTGCAGG3') (SEQ ID NO: 28), separately.

PCR products were analyzed and isolated from the 1.5% agarose gel using the QIAquick® gel extraction kit (Qiagen, Mississauga, Ontario, Canada). The purified PCR fragments were inserted into the plasmid vector, pGEM®-T-easy vector (Promega, Madison, WI, USA) and transformed into *Escherichia coli* strain YE707-J (Yeastern Biotech, Taipei, Taiwan). Plasmids containing inserts of the VL and the VH domains were prepared from the transformed *E. coli* and used for determination of DNA sequences of the VL and VH domains. The sequences then were used to design primers to be used in the second and the third steps.

Second Step: Preparation of a cDNA Consisting of MECA32 mAb Kappa Light Chain and His-Tag, and Inserting it into pET-26b Plasmid Vector The sequence of the VL chain from the first step was used to design appropriate primer for obtaining full length kappa light chain cDNA sequence of MECA32 antibody. First, full-length kappa chain cDNA of MECA32 mAb was generated by RT-PCR from total RNA of MECA32 hybridoma cells using primers listed below:

```
Forward primer:
                                  (SEQ ID NO: 29)
5'GATCCTGACATCCAGATGACCCAGACTCC3'
and Reverse primer:
                                  (SEQ ID NO: 30)
5'CACACTCATTCCTGTTGAAGCTCTTG3'.
```

Figure 3A:
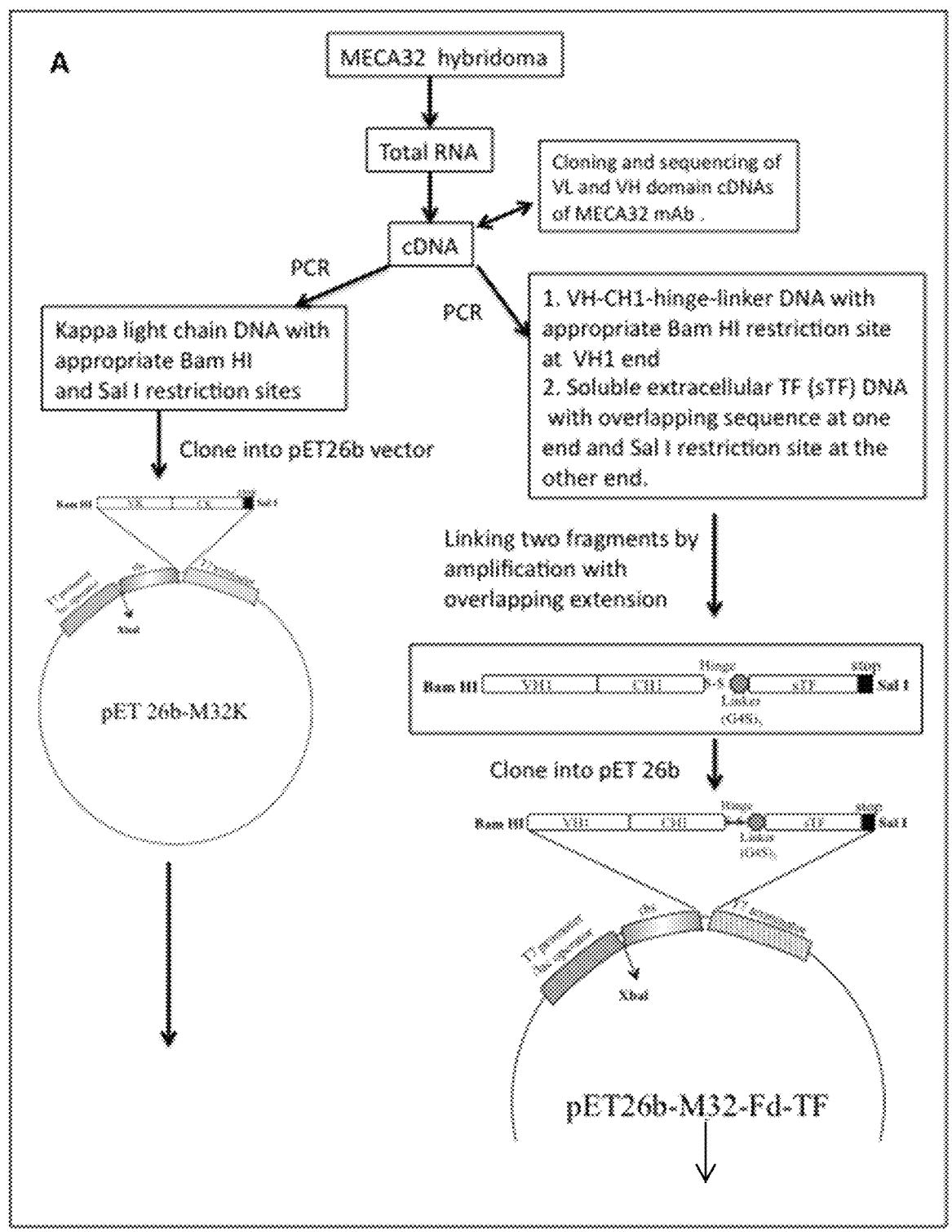
FIGS. 3A and 3B are diagrams showing construction of MECA32-Fab-TF expression vectors. Linker sequence (G$_4$S)$_3$ (SEQ ID NO: 50) shown is the same linker sequence that corresponds to amino acid positions 225-239 of SEQ ID NO: 23.

The purified PCR fragment with BamHI and Sal I restriction sites was inserted into the plasmid vector pET26b with a (His)$_6$-tag at the carboxyl terminus of the CK domain and this plasmid was designated as pET26b-M32K (FIG. 3A).

Third Step: Preparation of MECA32-Fd-hinge-linker-TF cDNA and Inserting into pET26b Plasmid Vector We first prepared a cDNA consisting of MECA32 mAb Fd, hinge region plus and linker sequence by PCR using cDNA template from MECA32 hybridoma cells and the following primer pair:

```
Forward primer:
                                  (SEQ ID NO: 31)
5'GACATCCAGATGACCCAGACTCC3'
and Hinge linker Reverse primer:
                                  (SEQ ID NO: 32)
5'AGAGCCACCTCCGCCTGAACCGCCTCC

ACCTGTACATCCACAAGGATTGCATTCC3'.
```

Next, we prepared a cDNA consisting of (Gly4Ser)3 (SEQ IS NO: 50) linker sequence and extracellular domain of human tissue factor (AA. 33-251) (hTF) by PCR using cloned hTF cDNA template and the following primer pair:

```
hTF linker forward primer:
                                  (SEQ ID NO: 33)

5'GGCGGAGGTGGCTCTGGCGGTGGCGGA

TCGTCAGGCACTACAAATACT GTGG3'
and

TF reverse primer:
                                  (SEQ ID NO: 34)
5'CAGTGTGAGGTGCAACTGGTGGAG3'.
```

Two PCR products were stitched by overlapping extension. The final fused PCR product was inserted into pET-26b vector. This vector was designated as pET26b-M32-Fd-TF (FIG. 3A).

Fourth Step: Construction of a biscistronic plasmid vector containing both MECA32 Fd-hinge-(Gly$_4$Ser)$_3$linker-TF and MECA32 Kappa Light Chain with a His-tag We generated a DNA fragment by PCR using pET26b-M32-Fd-TF as a template and the following primer pair:

```
26b-RBS-F:
                                  (SEQ ID NO: 35)
5'ACAATTCCCCTCTAGATTTTGTTTAACT

TTAAGAAGGAGA 3'
and

26b-Termination-R:
                                  (SEQ ID NO: 36)
5'CAAAATTATTTCTAGATTTCGGGCTTTG

TTAGCAGCCGG 3'.
```

Figure 3B:
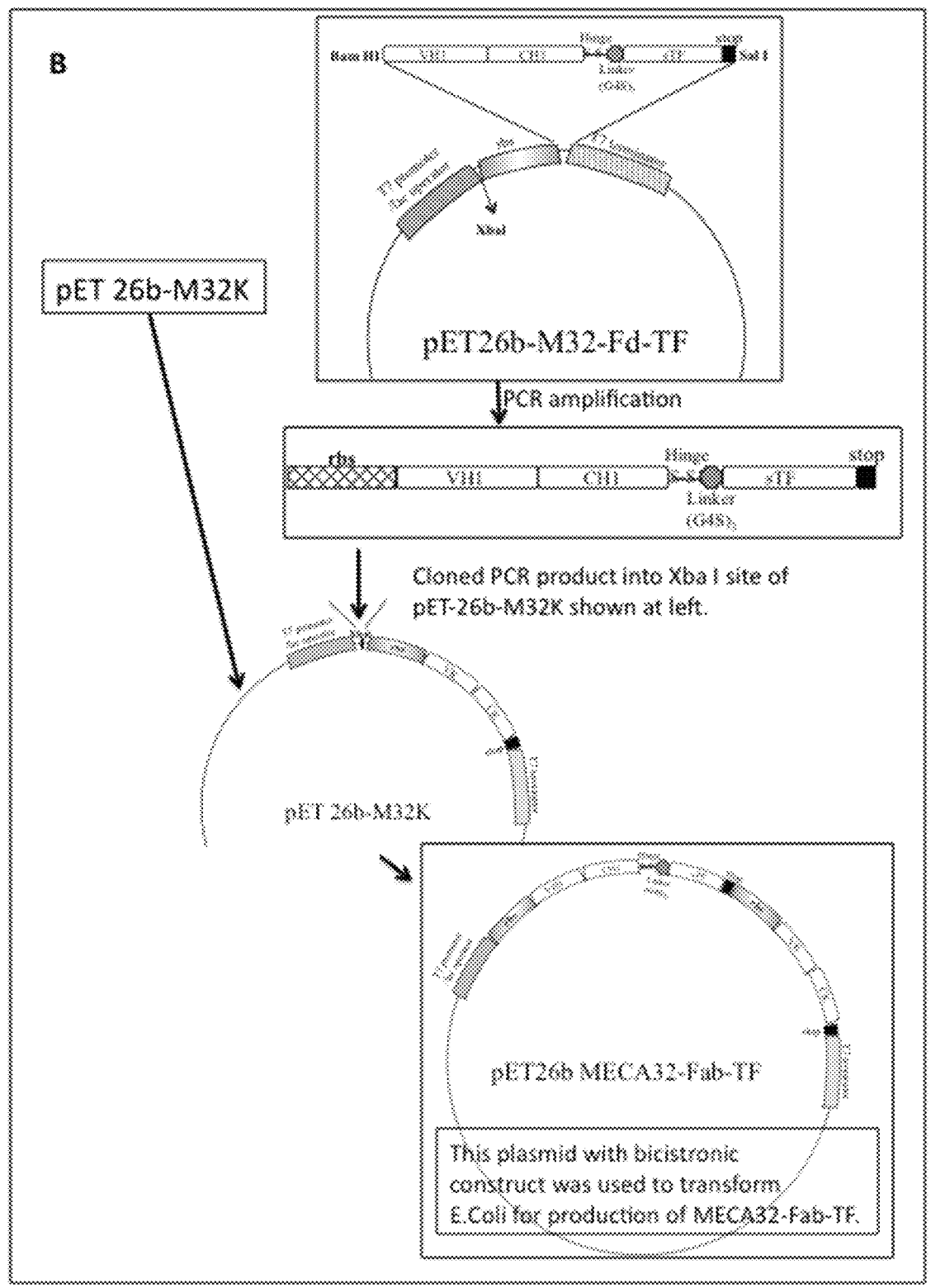

This DNA fragment included a ribosome binding sequence (rbs), VH1 and CH1 of MECA32 mAb heavy chain, hinge region, linker sequence, hTF, and a stop codon. This fragment was then inserted into Xba I restriction site of pET26b-M32K. The sequence of the entire insert was verified by DNA sequencing using the dye-deoxy method. This plasmid construct was designated as pET26b MECA32-Fab-TF (FIG. 3B) and transformed into the E. coli SHuffle® T7 Express strain (New England Biolabs Corp.) for protein expression. The diagrams summarizing the construction steps of this bicistronic plasmid expression vector for production of MECA32-Fab-TF is shown in FIGS. 3A and 3B.

Production of Fab of MECA32 Anti-Mouse PLVAP Monoclonal Antibody Co-Expressing Human Tissue Factor (MECA32-Fab-TF)

To produce MECA32-Fab-TF, a colony (1-2mm) of fresh E. coli culture was inoculated into 4 ml of 2xYT medium containing 30 μg/ml kanamycin at 30° C., 230 rpm overnight. Next morning, the overnight culture was inoculated into 400 ml of 2xYT medium containing 30 μg/ml kanamycin and continued to grow at 30° C., 250 rpm. When the absorbance at 600nm reached ~0.6-0.8, isopropyl β-D-1-thiogalactopyranoside (IPTG) was added to a final concentration of 0.4 mM for induction of recombinant protein production. Shaking was continued at 30° C. for about 20 h.

The cells were harvested by centrifugation at 10000×g for 20 min at room temperature and used to isolate inclusion bodies. The cell paste was suspended in 4 ml of 10 mM Tris/HCl, pH 7.5, containing 150 mM NaCl, 1 mM MgCl$_2$, 0.17 mg/ml PMSF and 2 mg/ml hen's-egg white lysozyme (Sigma). Benzonase® nuclease (250 units; EM Science) was added and the suspension was mixed gently at room temperature for 1.5 hour then centrifuged at 12000×g for 15 min. The pellet was resuspended in 10 mM Tris/HCl, pH 7.5, containing 1 mM EDTA and 3% Nonidet™ P40 detergent (2 ml), sonicated for 1 min at 50% power and centrifuged at 12000 g for 20 min. The pellet was re-suspended in water, sonicated for 20-30 seconds at 50% power and centrifuged at 12000×g for 20 min. The wash with water was repeated, and the final pellet, highly enriched for the inclusion bodies, was suspended in buffer containing 6 M guanidinium chloride, 0.5 M NaCl, 20 mM phosphate and 10 mM 2-mercaptoethanol, pH 8 by gentle mixing at room temperature overnight. The solution was held at room temperature overnight then diluted to a protein concentration of about 1 mg/ml in 6 M urea/50 mM Tris/HCl, pH 8 and dialyzed at 4° C. overnight against 10-20 volumes of the same buffer. Then, the dialysis was changed to a buffer containing 2 M urea, 50 mM Tris/HCl, 300 mM NaCl, 2.5 mM GSH, 0.5 mM GSSG, pH 8 (folding buffer). After dialysis for 2 days, the buffer was replaced with fresh folding buffer and the dialysis was continued for 2 more days. Next, dialysis buffer was changed to a buffer of 1M urea, 50mM Tris-HCl, 300 mM NaCl pH8 and the dialysis was continued for one more day. The dialysis was then carried out in the same buffer with sequentially reduced concentrations of urea from 0.8M urea for 6 hours, 0.56M urea overnight, and 0.28M urea for 6 hours. Finally, the dialysis was carried out in folding buffer without urea and continue overnight. The refolded supernatant was loaded onto a nickel nitrilotriacetic acid (Ni-NTA; GE Healthcare) column and eluted with 500mM immidazol in 50 mM sodium phosphate and 0.3M NaCl at pH7.0. Recombinant MECA32-Fab-TF was further purified by HiLoad® 16/60 Superdex® 75 prep grade (GE Healthcare) gel filtration column chromatography. Eluates containing target MECA32-Fab-TF were analyzed by SDS-PAGE and pooled. MECA32-Fab-TF was characterized by ELISA to confirm binding to mouse PLVAP. Tissue factor specific activity of MECA32-Fab-TF was measured using a chromogenic TF assay.

Development of plasmid construct to express recombinant Fab fragment of CSRO2 anti-human PLVAP monoclonal antibody co-expressing water-soluble human tissue factor (CSRO2-Fab-TF)

We also produced recombinant anti-human PLVAP CSRO2-Fab-TF protein similar to MECA32-Fab-TF. This protein was developed based on the anti-human PLVAP mAb CSRO2. The structure of this recombinant protein was substantially similar to MECA32-Fab-TF described above, except for the different Ab domains and absence of His-tag at the carboxyl end of the kappa light chain. His-tag was eliminated because his-tag was not required for purification of CSRO2-Fab-TF. CSRO2-Fab-TF was purified by using anti-human kappa light chain KappaSelect affinity column chromatography (GE Healthcare Life Sciences, Piscataway, NJ). CSRO2 mAb is a humanized monoclonal antibody against human PLVAP.

The procedure used to prepare the plasmid construct for production of CSRO2-Fab-TF was similar to the making of the plasmid construct for MECA32-Fab-TF with some modification. The first step described earlier for cloning cDNAs to obtain DNA sequences of 5'-ends of antibody heavy chain and light chain was be skipped, because cDNA sequences for CSRO2 mAb heavy chain and light chain were already known. Therefore, only three steps were required to prepare CSRO2-Fab-TF expression construct. These three steps are described below.

First Step: Insertion of CSRO2 mAb Light Chain cDNA into pET26b Plasmid Vector

Total RNA from NSO cell line producing CSR02 mAb was reverse-transcribed to cDNA using oligo-dT as primer. Kappa light chain cDNA of CSR02 was generated by PCR using the oligo-dT-primed cDNA as template and the primer pair shown below:

```
CSRO2-VK3F-26b F Nde I forward primer:
                                  (SEQ ID NO: 37)
5'TATGGATGTTGTGATGACCCAATCTCCA 3'

Kappa-R-26b-Not 1 reverse primer:
                                  (SEQ ID NO: 38)
5'GGCCGCTAACACTCTCCCCTGTTG 3'.
```

The purified PCR DNA fragment for CSRO2mAb light chain was then inserted into the Nde I and Not I sites of plasmid vector pET26b to generate pET26b-cVK3.

Second Step: Construction of a pET26b Plasmid Vector Inserted with cDNA for Expression of a Fusion Polypeptide Comprised of VH1, CH1 and Hinge Region of CSRO2 mAb Plus (Gly$_4$Ser)$_3$ Linker Sequence and Extracellular Domain of Human Tissue Factor (AA. 33-251) (hTF)

This plasmid was constructed by PCR using cDNA prepared from NSO cell line and cloned human tissue factor cDNA as templates. The following primer pairs were used for PCR:

I) Primer Pair for VH1-CH1-Hinge Region of CSRO2 mAb Heavy Chain and Linker Sequence:

```
VH5-pro26b-NdeI-F forward primer:
                                  (SEQ ID NO: 39)
5'TATGCAGGTCCAACTGGTGCAGTCTGG 3'
and Hinge linker R:
                                  (SEQ ID NO: 40)
5'AGAGCCACCTCCGCCTGAACCGCCTCCACCT

GGGCATGATGGGCATGGGGGACC 3'.
```

Primer Pair for Linker Sequence-hTF-Plus Restriction Site for Insertion:

```
hTF linker F:
                                  (SEQ ID NO: 41)
5'GGCGGAGGTGGCTCTGGCGGTGGCGGA

TCGTCAGGCACTACAAATACTGTGG 3'
```

-continued hTF R-Not 1:

(SEQ ID NO: 42)

5'GGCCGCTATTCTCTGAATTCCCCTTTCTCCTGG 3'.

The PCR fragments generated from the two PCR reactions described above were further fused and amplified by overlapping extension. The fused cDNA was inserted into pET26b plasmid vector which was designated as pET26b-VH5-Fd-TF.

Third Step: Construction of a Biscistronic Plasmid Vector Containing cDNAs for both CSRO2 mAb Fd-hinge-(Gly4Ser)3linker-TF and CSRO2 mAb Kappa Light Chain We generated a DNA fragment by PCR using pET-26b-VH5-Fd-TF as template and the following primer pair:

26b-RBS-F:

(SEQ ID NO: 43)

5'ACAATTCCCCTCTAGATTTTGTTTAACTTTAAGAAGGAGA 3' and

26b-Termination-R:

(SEQ ID NO: 44)

5'CAAAATTATTTCTAGATTTCGGGCTTTGTTAGCAGCCGG 3'.

Figure 4:
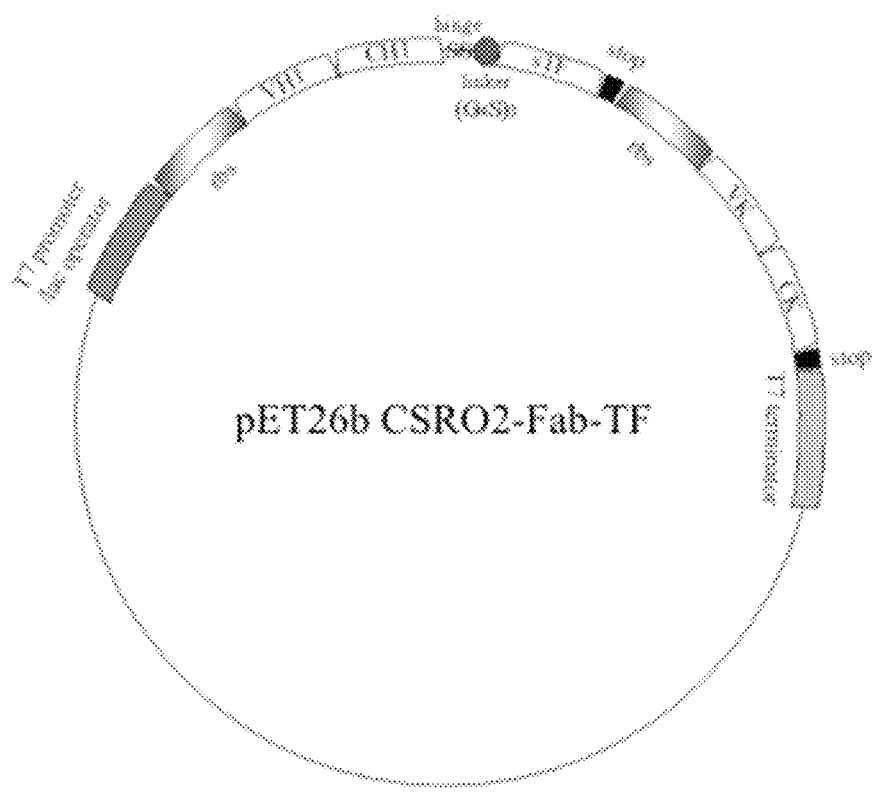
FIG. 4 is a diagram of the expression construct for CSRO2-Fab-TF. Linker sequence (G$_4$S)$_3$ (SEQ ID NO: 50) corresponds to amino acid positions 225-239 of SEQ ID NO: 23.

The amplified DNA fragment included a ribosome binding site (rbs); VH1, CH1 and hinge sequence of CSRO2 heavy chain; linker sequence; soluble human tissue factor; and a stop codon. This DNA fragment was inserted into the Xba I site of pET26b-cVK3 vector to derive a new biscistronic plasmid vector designated as pET26b CSR02-Fab-TF (FIG. 4). This plasmid was used to express both kappa light chain and fusion heavy chain under the control of a single promoter. The sequence of the entire insert was verified by DNA sequencing using the dye-deoxy method.

Production of Recombinant Fab Fragment of CSRO2 Anti-Human PLVAP Monoclonal Antibody Co-Expressing Water-Soluble Human Tissue Factor (CSRO2-Fab-TF)

Expression of recombinant CSR02-Fab-TF protein. Transformation of *Escherichia coli* Shuffle® T7 Express (New England Biolabs) was performed by incubating competent cells with pET-26b CSR02-Fab-TF plasmid DNA on ice for 5 min, heating for exactly 30 seconds in a 42° C. water bath and followed by placing on ice for 2 minutes. Prior to plating on selective medium, the transformants were incubated at 30° C. while shaking at 250 rpm with SOC medium (0.5% Yeast Extract; 2% Tryptone; 10 mM NaCl; 2.5 mM KCl; 10 mM $MgCl_2$; 10 mM $MgSO_4$; 20 mM Glucose) for 60 min. Expression of CSR02-Fab-TF was induced with 0.05 mM of isopropyl-ß-D-thiogalactopyranoside for 16 hours at 30° C. or 37° C. Following the induction, the bacterial cells were subjected to lysis by in 1× PBS with 0.2% TWEEN® 80 detergent in the presence of lysozyme and Benzonase® Nuclease at room temperature for 2 hours. Cell lysate was harvested by centrifuging at 10000 rpm for 30 minutes at 4° C. Supernatant was collected and filtered to isolate the soluble fraction.

Purification of CSR02-Fab-TF by KappaSelect and Capto AdhereMmultimodal Column Chromatography. KappaSelect column (1 ml) was equilibrated with phosphate buffered saline (PBS), pH 7.4 (0.01M phosphate buffer, 0.0027M KCl, 0.14M NaCl). *E. coli* cell lysates containing CSR02-Fab-TF was loaded at a flow ratel ml/min. After application of samples, the column was washed with the equilibration buffer till OD280 dropped to baseline. The rest of bound proteins were eluted with 0.1M glycine buffer, pH 2.7 containing 0.25 M sucrose. The eluate was immediately adjusted to physiological pH by adding 50 µl of 1M Tris-base buffer, pH9.0 per 1 ml eluate.

The eluted CSRO2-Fab-TF from KappaSelect column was further purified with a Capto™ Adhere column (5 ml) pre-equilibrated with 20 mM Tris buffer, pH 7.5. The CSR02-Fab-TF sample eluted from KappaSelect column was diluted 50 fold with 20 mM Tris buffer, pH 7.5 and followed by loading it onto a Capto™ Adhere column at a flow rate 1 ml/min. After application of the sample, the column was washed with equilibration buffer until OD280 dropped to baseline. The bound CSRO2-Fab-TF protein was then eluted with 20 mM Tris buffer, pH 7.5 containing 200 mM NaCl.

Production of Soluble Recombinant Human and Mouse PLVAP Proteins (hPLVAP and mPLVAP)

Production of (hPLVAP). Plasmid pGEM®-T Easy-hPLVAP$_{51-442}$ was generated by inserting a PCR fragment representing the truncated PLVAP (amino acid residues 51 to 442 comprising the extracellular domain of mouse PLVAP) into the Easy Vector (Promega). This PCR fragment was generated from a cDNA clone of human PLVAP (NM_031310) (OriGene, Rockville, Md.) by PCR using the following primer pair:

(SEQ ID NO: 45)

5'-CATATGAACGTGCACGTGAGCACAGAGTCC-3' and (SEQ ID NO: 46)

5'-GGATCCTGAGCATATCCCTGCATCCTCC-3'.

For construction of plasmid pET-15b-hPLVAP$_{51-442}$ to produce recombinant PLVAP protein, a cDNA fragment encoding the amino acid residues 51 to 442 of PLVAP with NdeI/Bam HI recognition sequences (boxed sequences) at the ends was excised from pGEM®-T Easy-hPLVAP$_{51-442}$ and inserted into pET-15b (Novagen). The expression construct described above was verified by DNA sequencing and transformed to *Escherichia coli* (Rosetta-gami™2(DE3) pLysS competent cells) (EMD Millipore Corp.).

Figure 5:
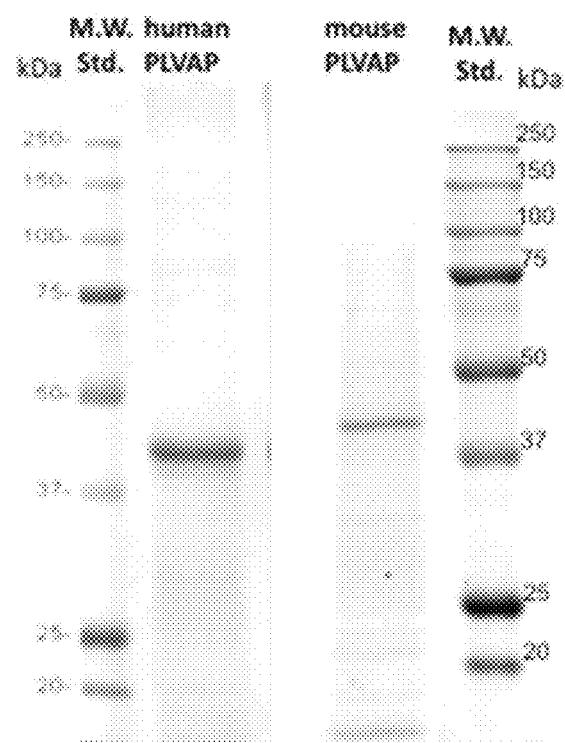
FIG. 5 is a picture of an SDS-PAGE of recombinant human PLVAP and mouse PLVAP. Recombinant human PLVAP (5 µg) and mouse PLVAP (2.5 µg) were analyzed with 12% polyacrylamide gel.

A His-tagged hPLVAP fusion proteins was produced and purified as described below. A colony (1-2 mm) of transformed *E. coli* from fresh culture was inoculated into 4 ml of TB medium containing 100 µg/ml ampicillin, 34 µg/ml chloramphenical, 12.5 µg/ml tetracycline at 37° C., 230 rpm overnight. The overnight culture was inoculated into 400 ml of TB medium containing 100 µg/ml ampicillin 34 µg/ml chloramphenical, 12.5 µg/ml tetracycline and continued to grow at 37° C., 250 rpm. When the absorbance at 600 nm reached about 0.6~0.8, isopropyl β-D-1-thiogalactopyranoside (IPTG) was added to a final concentration of 1.66 mM to induce protein production. Shaking was continued at 30° C. for about 20 h. Cells were harvested by centrifugation at 10000 g for 30 minutes at 4° C. The cell pellet was re-suspended in 12 ml equilibration-wash buffer (50 mM sodium phosphate, 300 mM NaCl, pH 7, 10 mM imidazol) supplemented with 8 M urea and stored at −20° C. for at least 2 hours. The thawed sample was sonicated for 10 seconds, with a 30 second pause between each burst to reduce the viscosity until it becomes translucent. The cell suspension was centrifuged at 10,000-12,000×g for 20 min at 4° C. to pellet any insoluble material. The supernatant from the previous step was applied to TALON® Resin column (Clontech) which has been equilibrated with 10 column volume of equilibration-wash buffer supplemented with 8 M urea. After washing the column with 10-20 column volumes of 1× equilibration-wash Buffer, recombinant polyhistidine-tagged human PLVAP protein was eluted with 5 column volumes of elution buffer (50 mM sodium phosphate, 300 mM NaCl, pH 7, 500 mM imidazol) containing 6 M urea. The purified recombinant protein in the eluate was dialyzed against 1× equilibration/wash buffer containing 3M urea at 4° C. for at least 4 hours, then buffer was changed to 1× equilibration-wash buffer containing 1M urea, and dialyze at 4° C. for at least 4 hours. Protein concentration was determined with Bradford dye binding assay (Bio-Rad, Hercules, CA). The protein was then digested with 1 unit of biotinylated thrombin (Novagen) for each mg of the recombinant PLVAP protein at 23° C. for 16 hours to remove polyhistidine-tag. Biotinylated thrombin was removed from the incubation by solid phase streptavidin-agarose. The resulting recombinant water soluble human PLVAP (hPLVAP) was dialyzed against 1× equilibration-wash buffer (50 mM sodium phosphate, 300 mM NaCl, pH 7) without urea. The protein concentration was determined and the protein was analyzed by SDS-PAGE for purity (FIG. 5).

Production of mPLVAP (mouse PLVAP). Plasmid pGEM-T Easy-mPLVAP$_{48-438}$ was generated by inserting a PCR fragment representing the truncated PLVAP (amino acid residues 48 to 438 comprising the extracellular domain of mouse PLVAP) into the pGEM® Easy Vector (Promega Corp.). This PCR fragment was prepared from a cDNA clone of mouse PLVAP (Invitrogen, Life Technologies Corp.) by PCR using the following primer pair:

```
mPLVAP CDS NdeI F:
                                       (SEQ ID NO: 47)
5'CATATGTATGGCAATGTGCACGCCACC3'
and mPLVAP Stop Xho I R:
                                       (SEQ ID NO: 48)
5'CTCGAGATCCACAGGTGGGCGATTCTGGC3'.
```

Next, a cDNA fragment encoding the amino acid residues 48 to 437 of PLVAP containing NdeI and XhoI recognition sequences at each end was excised from pGEM®-T Easy-mPLVAP$_{48-438}$ and inserted into pET-15b (Novagen-EMD Millipore, Darmstadt, Germany) for protein expression. After verification by DNA sequencing, this expression construct was transformed into *Escherichia coli* (Rosetta-gami™2(DE3)pLysS competent cells). Expression of His-tagged fusion mPLVAP protein in *Escherichia coli* Rosetta-gami2(DE3)pLysS competent cells was induced with 1 mM isopropyl-β-D-thiogalactopyranoside for 16 hours at 30° C. Following the induction, the bacterial cells were subjected to lysis by sonication in equilibration buffer (50 mM sodium phosphate, 300 mM NaCl, pH 7) supplemented with 8 M urea and separated into soluble and insoluble fractions by centrifugation at 15,652×g for 30 minutes at 4° C. To purify the His-PLVAP$_{48-438}$ protein, the soluble fraction was loaded onto a TALON® Metal Affinity Resin (Clontech, Palo Alto, CA) and was eluted with elution buffer (50 mM sodium phosphate, 300 mM NaCl, pH 7, 500 mM imidazole). The resulting mouse PLVAP$_{48-438}$ protein in the eluate was dialyzed against PBS. SDS-PAGE analysis of the purified His-mPLVAP is shown in FIG. 5.

Studies of CSRO2-Fab-TF and MECA32-Fab-TF Binding to Respective Human and Mouse PLVAP by ELISA In order to make sure that the recombinant anti-PLVAP-Fab-TF proteins can bind to human or mouse PLVAP protein, an ELISA assay was developed and used. First, each well of an ELISA plate was coated with 50 µl of 2.5 µg/ml human or mouse recombinant PLVAP protein in PBS-azide (0.02%) overnight at 4° C. Thereafter, the assays were carried out at room temperature. After three washes of each well with 150 µl washing buffer (PBS containing 0.2% Tween-20). Each well was blocked with 150 µl blocking buffer (PBS containing 2% BSA and 0.05% Tween-20) for 30 minutes. After three washes, 50 µl of anti-human PLVAP CSRO2-Fab-TF or anti-mouse PLVAP MECA32-Fab-TF was added into each well at different concentrations in duplicates. All wells were incubated for 45 minutes and washed three times. Wash well was then incubated with 50 µl biotinylated anti-human TF antibody (R&D Systems Corp.) at 1:500 dilutions in the blocking buffer for 45 minutes. After three washes, each well was incubated with 5000× diluted Streptavidin-alkaline phosphatase conjugate for 30 minutes. Each well was then incubated with 100 µl alkaline phosphatase substrate for 60 minutes and absorbance of each well was measured at 405 nm in a microplate reader.

The assay was also modified into a competitive binding assay. For the competitive binding assay, increasing concentrations of anti-PLVAP antibodies or Fab-TF were incubated with an optimal amount of biotinylated anti-PLVAP monoclonal antibody to compete for the binding to PLVAP. After incubation and washing, biotinylated antibody bound to PLVAP was quantified with streptavidin-alkaline phosphatase conjugate and chromogenic substrate.

Chromogenic Assay for Human Tissue Factor Activity

The TF activities of recombinant CSRO2-Fab-TF, MECA32-Fab-TF and MECA32 mAb crosslinked with human TF were measured using a chromogenic assay. This assay is based on binding of TF to factor VIIa and the ability of TF/FVIIa complex to activate factor X (FX), The TF activity was quantified indirectly by the amount of FXa produced. The FXa produced was measured kinetically according to the release of para-nitroamiline (pNA) from a FXa specific chromogenic, peptide substrate as an increase of absorbance at 405 nm. The IF activity was determined against a commercial water soluble recombinant IF standard (R&D systems Corp.). The chromogenic TF activity assay was based on the procedure reported by Philipp et al. See Philipp J, Dienst A, Unruh Maike, et al. "Soluble tissue factor induces coagulation on tumor endothelial cells in vivo if coadministered with low-dose lipopolysaccharides" *Arterioscler Thromb Vasc Biol.*; 23:905-910 (2003)

Hep3B HCC Xenograft Model in SCID Mice

Hep3B is a human HCC cell line. In order to demonstrate the therapeutic effectiveness of anti-PLVAP Fab-TF, we establish a HEP3B xenograft model in BALB/c C.B-17 SCID mice. Hep3B HCC xenograft was established by subcutaneous injection of 4 million Hep3B cells into right upper inner thigh of a 5 weeks old male C.B-17 SCID mouse under general anesthesia with inhalation of isoflurane. The cells were suspended in 60 µl of ice cold 75% BD MATRI-GEL™ (BD Bioscience Corp.) dissolved in Dulbecco's modified eagle medium (DMEM) (Life Technologies Corp.) without serum. Injection was carried out by using a 29 gauge insulin syringe.

Hep3 B cells used for injection were cultured in DMEM containing 10% fetal bovine serum, 1% GLUTA-MAX™ media, 1% antibiotics-antimycotics, and 1% HEPES. All reagents were purchased from Life Technologies. The cells for injection were harvested when they reached 80% confluency. The cells were lifted from the culture flask using trypsin-EDTA solution from Life Technologies according to the instruction of the manufacturer, and tumor cells were washed once with DMEM before suspending in ice cold 75% BD MATRIGEL™ matrix for injection. After injection, mice were followed regularly for growth of tumor xenograft. Normally, it took five to six weeks for tumors to become ready for the study.

Infusion of Anti-PLVAP Fab-TF into Tumor Feeding Artery

For treatment of Hep3B tumor xenograft with anti-PLVAP MECA32-Fab-TF, a mouse carrying Hep3B tumor xenograft was anesthetized with inhalation of isoflurane using a MATRX™ anesthesia machine. The mouse was laid in supine position under a dissecting microscope. The hair over the right inguinal area was removed with NAIR™ hair remover (Church & Dwight Co.) a day before infusion. After cleansing the skin with 75% alcohol, a 0.5 cm incision was made at the right inguinal area above tumor. The wound was deepened to expose right femoral artery and vein. Right femoral artery was then looped with a 6-0 nylon thread. The artery was gently retracted proximally. An arteriotomy was done with a micro-scissor distal to the retraction and a fine 33 gauge needle was inserted into the distal side. MECA32-Fab-TF or control antibody was infused slowly at a rate about 40 µl per minute. Injection was performed under close observation to ensure that there was no leakage. After infusion, the needle was withdrawn. The arteriotomy site was sealed with HISTOACRYL® adhesive (TissueSeal, AnnArbor, MI). The nylon for retraction was removed. After confirmation of adequate hemostasis, the incision wound was closed with continuous suture.

3D Sonography and Power Doppler for Measurement of Tumor Volume and Blood Flow

VEVO® 2100 High-Resolution Imaging System (Visual Sonics, Inc., Toronto, Canada) was used to acquire 3D tumor image according to the instruction of the manufacturer. Three perpendicular dimensions of the tumor were determined by taking the following measurements. Two perpendicular dimensions on the largest cross section area along tumor X and Y axes were measure first. The longest dimension along Z axis perpendicular to X and Y dimensions were then determined using the software provided by the vendor. Tumor volume was determined using the following formula for elliptical object: Volume=$\pi/6 \times length \times width \times height$. Tumor blood flow images were captured using 3D power Doppler according to the manual for a VEVO® 2100 High-Resolution Imaging System.

Measurement of Binding Affinities of MECA32-Fab-TF and CSRO2-Fab-TF

The assay used to determine binding affinity between anti-PLVAP-Fab-TF and target PLVAP was based on a chromogenic TF activity assay as described in the earlier section. Briefly, each well of an ELISA plate was coated with 2.5 µg/ml water soluble recombinant human or mouse PLVAP overnight. After washings and blocking as described for the ELISA to study CSRO2-Fab-TF and MECA32-Fab-TF binding to PLVAP, wells coated with human or mouse PLVAP protein were incubated with 50 µl of increasing concentrations of CSRO2-Fab-TF or MECA32-Fab-TF at 0.3125, 0.625, 1.25, 2.5, 5 and 10 µg/ml in duplicates. After incubation for 3 hours at room temperature, wells were washed and assayed for amounts of TF activity bound in wells using a TF standard curve as described in the earlier section for the chromogenic TF activity assay. The concentration of total CSRO2-Fab-TF or MECA32-Fab-TF added in each well was known and the concentration of bound CSRO2-Fab-TF or MECA32-Fab-TF in each well could be calculated from the assay results. These numbers were then analyzed using Scatchard plot analysis to determine the binding affinity of CSRO2-Fab-TF or MECA32-Fab-TF. See, e.g., Scatchard G. "The attractions of proteins for small molecules and ions" *Ann NY Acad Sci*. 51:660-672(1949).

Immunohistochemical (IHC) Staining of PLVAP in HEP3B Tumor Xenograft Using MECA32 Anti-PLVAP Monoclonal Antibodies To study expression of PLVAP in mouse Hep3B xenograft, sections of formalin fixed paraffin tissue block were processed for immunohistochemical staining by anti-PLVAP monoclonal antibodies. After de-paraffinization and rehydration of tissue sections following routine procedures, slides with tissue sections in a carrier were placed in a beaker and immersed in Target Retrieval Solution (Dako, Inc. Carpinteria, CA). The beaker was placed in an autoclave and heated at 121° C. for 10 minutes. After cooling, the slides were transferred into distilled water. The section on each slide was then treated with 200-400µl hydrogen peroxide in Ventana iView™ DAB Detection kit (Ventana Medical Systems, Inc.) to quench endogenous peroxidase. After rinsing slides with Tris-buffered saline (TBS) (Dako), Sections were incubated with 5 µg MECA32 anti-PLVAP monoclonal antibodies diluted in TBS containing 0.1% bovine serum albumin (TBS-BSA) with at 37° C. for 60 minutes. After washing by submerging slides in TBS buffers for 5 minutes three times, the sections were incubated with a biotinylated secondary antibody (e.g., biotinylated sheep anti-rat IgG for MECA32 mAb) at a dilution recommended by the vendor and incubated at room temperature for 15 minutes. The sections on slides were washed similarly as described above. The sections on slides were incubated with freshly prepared DAB substrate in the kit for 30 minutes. The slides were rinsed with distilled water a few times. After counter stain with Gill's hematoxylin solution for 15 seconds, the slides were rinsed with TBS followed with distilled water. After air-drying sections, the sections were covered with Permount medium and cover slips.

Results

PLVAP Expression in HCC and HEP3B Xenograft

Our earlier study showed that PLVAP is differentially expressed on vascular endothelial cells of HCC and not in vascular endothelial cells of non-tumorous liver tissue. The differential expression of PLVAP offered an opportunity to target HCC for therapeutic purpose. We conceived a novel approach of using anti-PLVAP monoclonal antibody or its Fab fragment serve as a carrier for a co-expressed blood coagulation triggering tissue factor protein for treatment of HCC. Infusion of such a therapeutic agent into tumor feeding artery was believed to result in binding of this therapeutic antibody or its Fab fragment to vascular endothelial cells of HCC, trigger blood clot formation in tumor blood vessels and lead to ischemic necrosis of tumor.

Figure 6A:
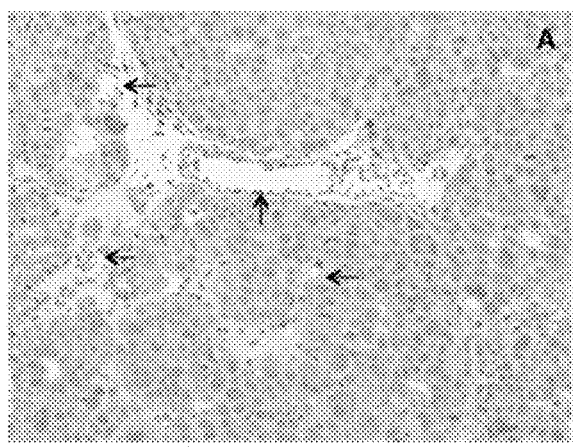
FIGS. 6A and 6B are micrographs illustrating immunohistochemical (IHC) staining of PLVAP expression in vascular endothelial cells of Hep3B tumor xenograft in SCID mouse. MECA32 anti-mouse PLVAP monoclonal antibody (10 µg/ml) was used for IHC staining (panel B). The left panel was the section of the same block stained with normal rat IgG at the same concentration as negative control (panel A). The result shows that vascular endothelial cells in Hep3B tumor xenograft like human HCC were stained positively for PLVAP expression (dark brown precipitates pointed by arrows in panel B). The PLVAP expressed by tumor vascular endothelial cells can therefore be targeted to assess therapeutic effects of MECA32-TF and MECA32-Fab-TF. The same vessels cannot be stained with control rat IgG (arrows in panel A).
Figure 6B:
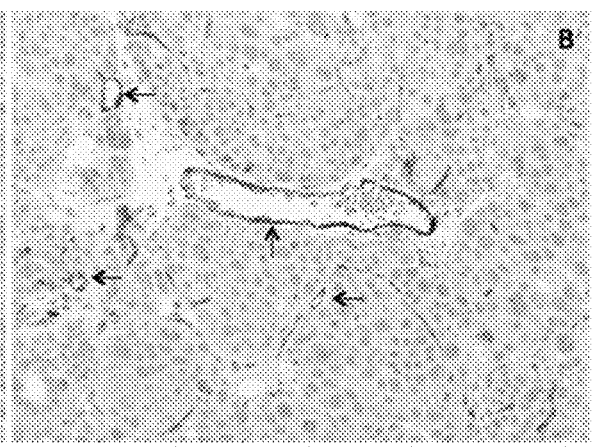

To demonstrate the feasibility of this approach, we established a human HCC xenogaft model in SCID mice using HEP3B HCC cell line. We then determined whether vascular endothelial cells grew into HEP3B tumor xenograft expressed mouse PLVAP by immuno-histochemical (IHC) staining using MECA32 anti-mouse PLVAP mAb. As shown in FIG. 6B, vascular endothelial cells of HEP3B tumor xenograft in SCID mice indeed expressed PLVAP like human HCC. Therefore, HEP3B xenograft could be used for the study to demonstrate anti-tumor effect of anti-PLVAP mAb or its Fab fragment conjugated with human tissue factor.

Effect of MECA32 mAb Conjugated with Soluble Human TF on HEP3 B Xenograft

Figure 7:
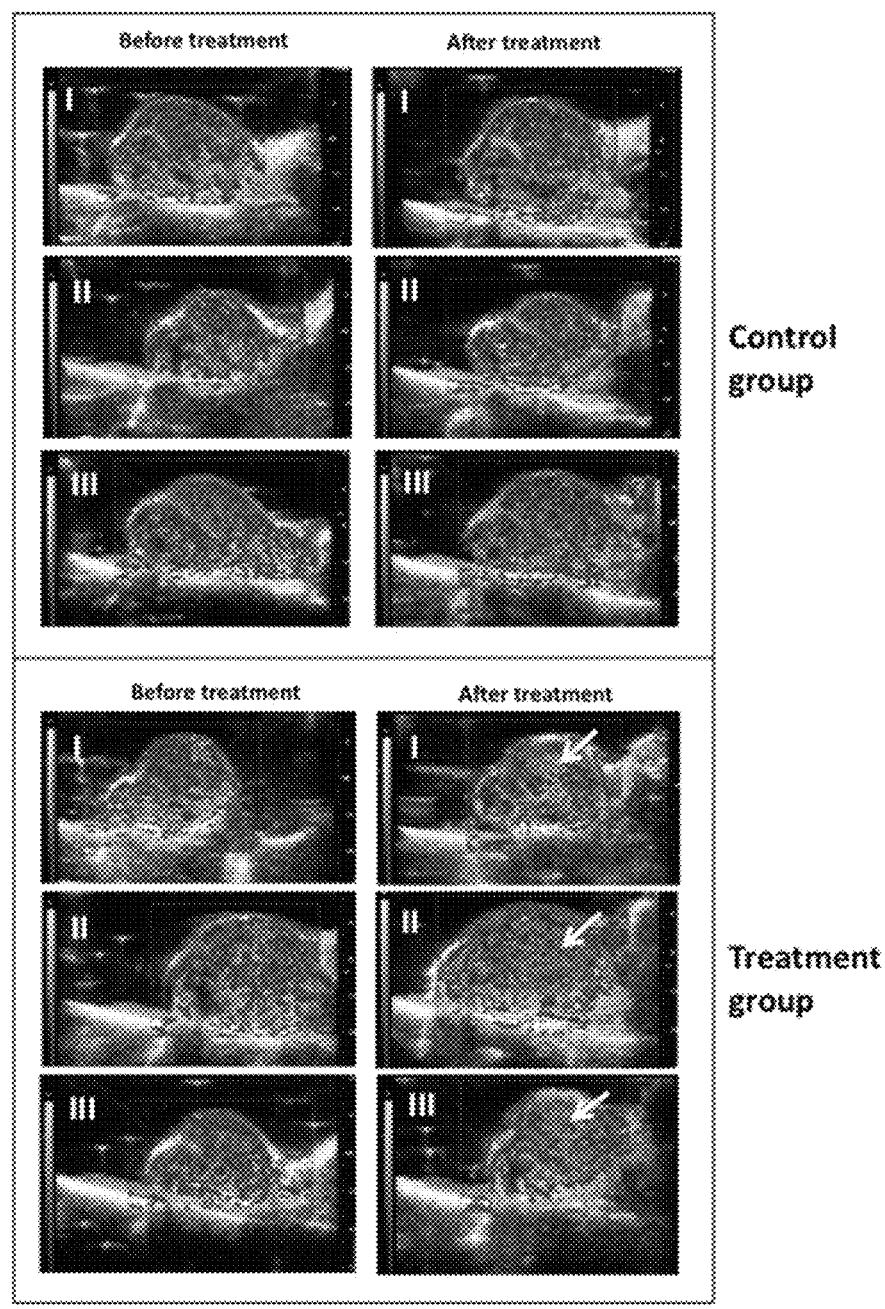
FIG. 7 shows pictures of blood flow in tumors by sonography, illustrating the effect of anti-PLVAP MECA32 monoclonal antibody (mAb) conjugated with recombinant human tissue factor (MECA32-TF) on tumor blood flow. Tumor blood flow was assessed with 3D Power Doppler sonography. Power Doppler was performed 48 hours before and 48 hours after the treatment. The result show that blood flow was significantly diminished in the group treated with 20 μg MECA32-TF (white arrows) but not in the control group treated with 24 μg MECA32 mAb. Red blood flow signals were present inside tumors before treatment.
Figure 8:
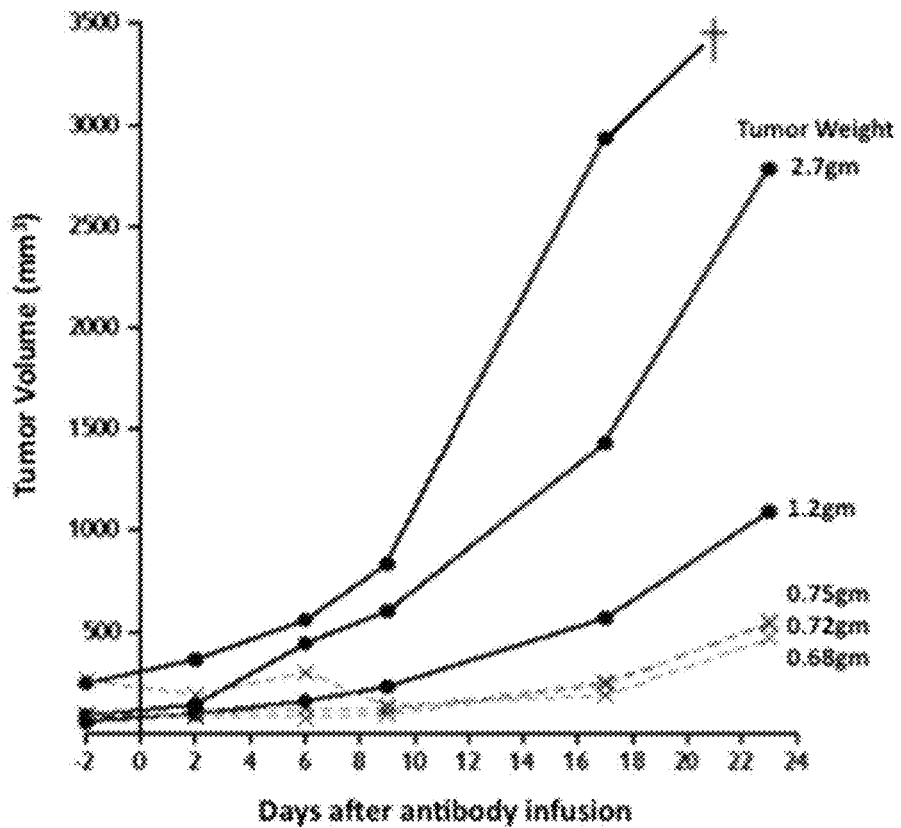
FIG. 8 is a line graph of tumor volume over time, illustrating the effect of MECA32-TF infusion on tumor growth. The result shown in this figure are from the same experiment described in FIG. 7. SCID mice bearing Hep3B tumor xenografts were treated by infusion of 20 μg MECA32-TF into a tumor feeding artery. The control group was treated with 24 μg MECA32 mAb. Tumor volumes were monitored using 3D sonography before and after treatment on day 0. One of the mice in the control group died on day 20 after the initial treatment due to rapid progressive tumor growth (†). The growth rates of the treatment group and the control group were compared using linear mixed-effects model and were significantly different (p=0.0002). The results of this study (FIGS. 7 and 8) demonstrated that anti-PLVAP antibody conjugated with tissue factor was able to block tumor blood flow and effectively inhibit tumor growth. Solid circle (•): MECA32 mAb control (n=3); Cross (x): MECA32-TF treatment group (n=3).

First, we treated SCID mice carrying HEP3B xenograft tumors with MECA32 mAb chemically conjugated with recombinant water soluble human tissue factor (MECA32-TF). Human TF was used, because human TF is effective to trigger blood coagulation in both human and mice and cDNA of human TF was commercially available. Each tumor-bearing mouse was treated by infusion of 24 µg MECA32-TF (treatment group) or 20 µg MECA32 mAb (control group) in 100 µl of phosphate buffered saline (PBS) into a tumor feeding right femoral artery under dissecting microscope. The slightly less amount of MECA32 mAb (20 µg) was used to adjust for higher molecular weight of MECA32-TF. 3D power Doppler was used to assess tumor blood flow 48 hours before and after treatment. The results showed significant reduction of intra-tumor blood flow signals after treatment with MECA32-TF in the treatment group and not in the control group (FIG. 7). Follow up of tumor growth showed significant suppression of tumor growth in the MECA32-TF treatment group and not in the control group (FIG. 8). The results of this study support that anti-PLVAP monoclonal antibody conjugated with human TF was effective for treatment of HCC xenografts.

Development and Characterization of MECA32-Fab-TF

For chemical conjugation of TF to MECA32 mAb, it was difficult to consistently and reproducibly control the numbers and the sites of TF protein molecules cross-linked to MECA32 mAb. MECA32-TF prepared by chemical cross-linking did not yield homogeneous product. The high molecular weight of MECA32-TF conjugate (approximately 170 kDa) also leads to long circulation half-life with increased chance of causing adverse side effects.

Figure 9:
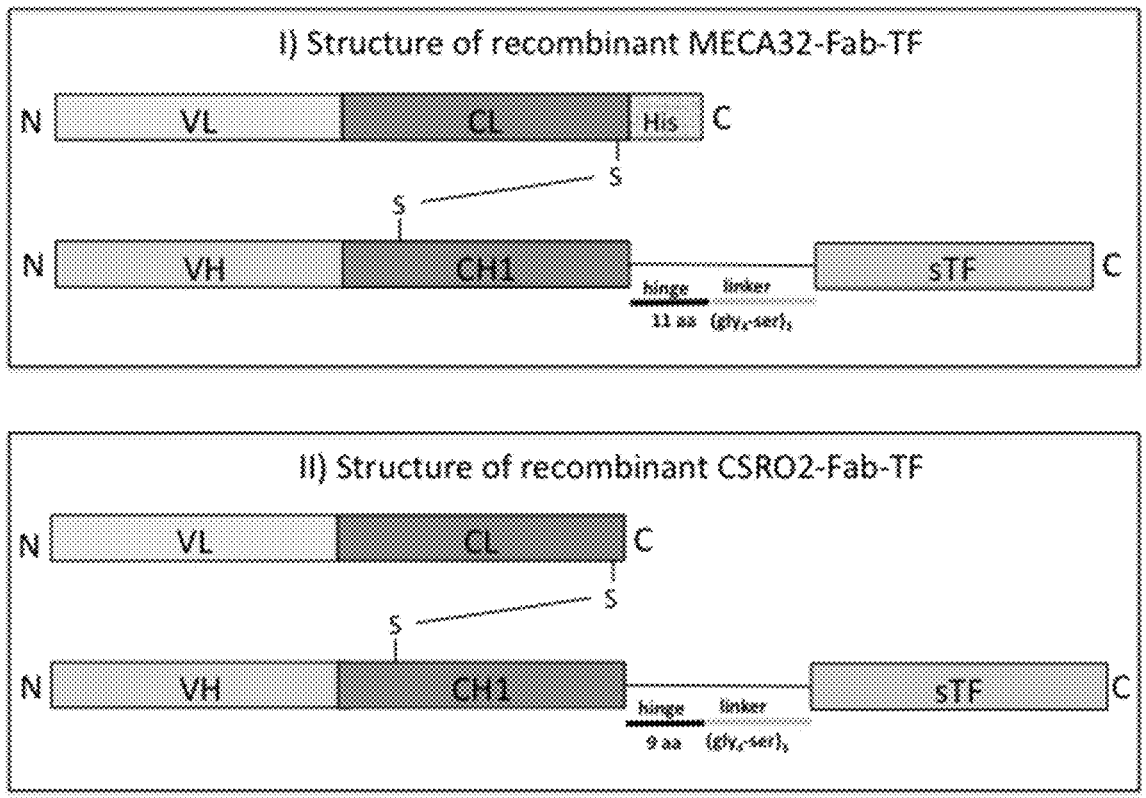
FIG. 9 is a picture providing diagrams of the structure of recombinant anti-mouse PLVAP MECA32-Fab-TF and anti-human PLVAP CSRO2-Fab-TF conjugates. The major difference between two anti-PLVAP Fab-TFs is that there is a histidine-tag (His-tag) at the C-terminus of kappa light chain of MECA32-Fab-TF. The histidine-tag was introduced for purification purposes. CSRO2-Fab-TF does not require histidine-tag for purification. In both instances, the linker sequence (gly$_4$ser)$_3$ is identical to amino acid positions 225-239 of SEQ ID NO: 23.

In order to have a structurally well defined homogeneous therapeutic biologic with shorter half-life to limit off-target side effects, we developed a novel recombinant protein that consisted of Fab portion of anti-PLVAP mAb and extracellular domain of human tissue factor linked to the carboxyl end of the heavy chain constant domain 1. We then produced an anti-murine PLVAP MECA32-Fab-TF recombinant protein (MECA32-Fab-TF). A diagram depicting the structure of this recombinant protein is shown in FIG. 9.

Figure 10:
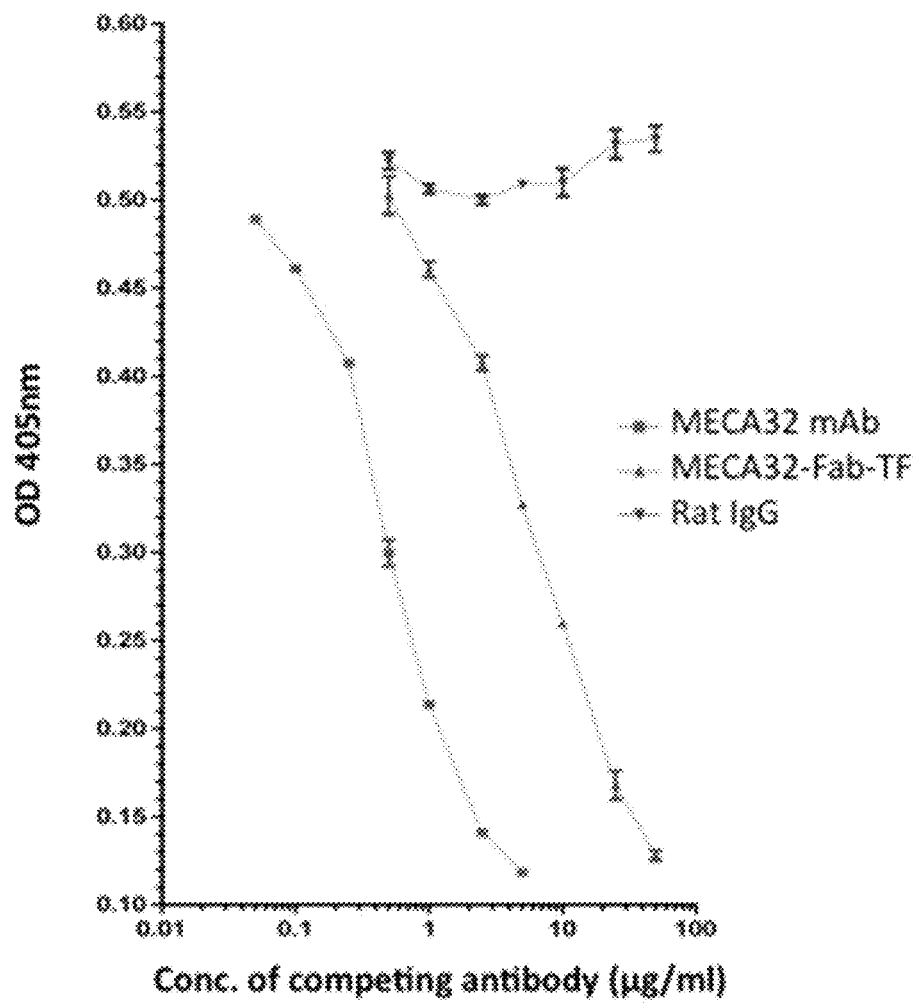
FIG. 10 is a line graph of OD405nm versus concentration of competing antibody, illustrating MECA32-Fab-TF binding to mouse PLVAP by competitive enzyme-linked immunoassay. ELISA plate wells were coated with recombinant water soluble mouse PLVAP (2.5 μg/ml) overnight. After blocking wells with buffer containing bovine serum albumin, increasing concentrations of rat IgG (0.5 μg/ml to 50 μg/ml), MECA32-Fab-TF (0.5 μg/ml to 50 μg/ml) or MECA32 mAb (0.05 μg/ml to 5 μg/ml) were incubated with 0.25 μg/ml of biotinylated MECA32 mAb. Binding of biotinylated MECA32 mAb to PLVAP was measured with streptavidin-alkaline phosphatase conjugate and chromogenic substrate. The results show that both MECA32 mAb and MECA32-Fab-TF could compete with biotinylated MECA32 mAb for binding to mouse PLVAP, but not rat IgG control. As expected MECA32 mAb was approximately one log more potent than MECA32-Fab-TF for their binding to mouse PLVAP, because the binding affinity of MECA32-Fab-TF is one log lower than MECA32 mAb.

Purified MECA32-Fab-TF was used to compete with biotinylated MECA32 mAb for binding to mouse PLVAP. These results indicated that MECA32-Fab-TF indeed retained its ability to bind to PLVAP (FIG. 10). Scatchard analyses of six different batches of MECA-32-Fab-TF also showed high binding affinity to mouse PLVAP with Kd of $5.7\pm1.4\times10^{-8}$M. The TF linked at the carboxyl terminus of MECA32 Fd was also functional and could interact with factor VIIa to activate factor X. The measured tissue factor specific activity was $90\pm22$ µg (n=6) in each milligram of MECA32-Fab-TF.

Effect of MECA32-Fab-TF on HEP3B Tumor Xenograft in SCID mice

Figure 11:
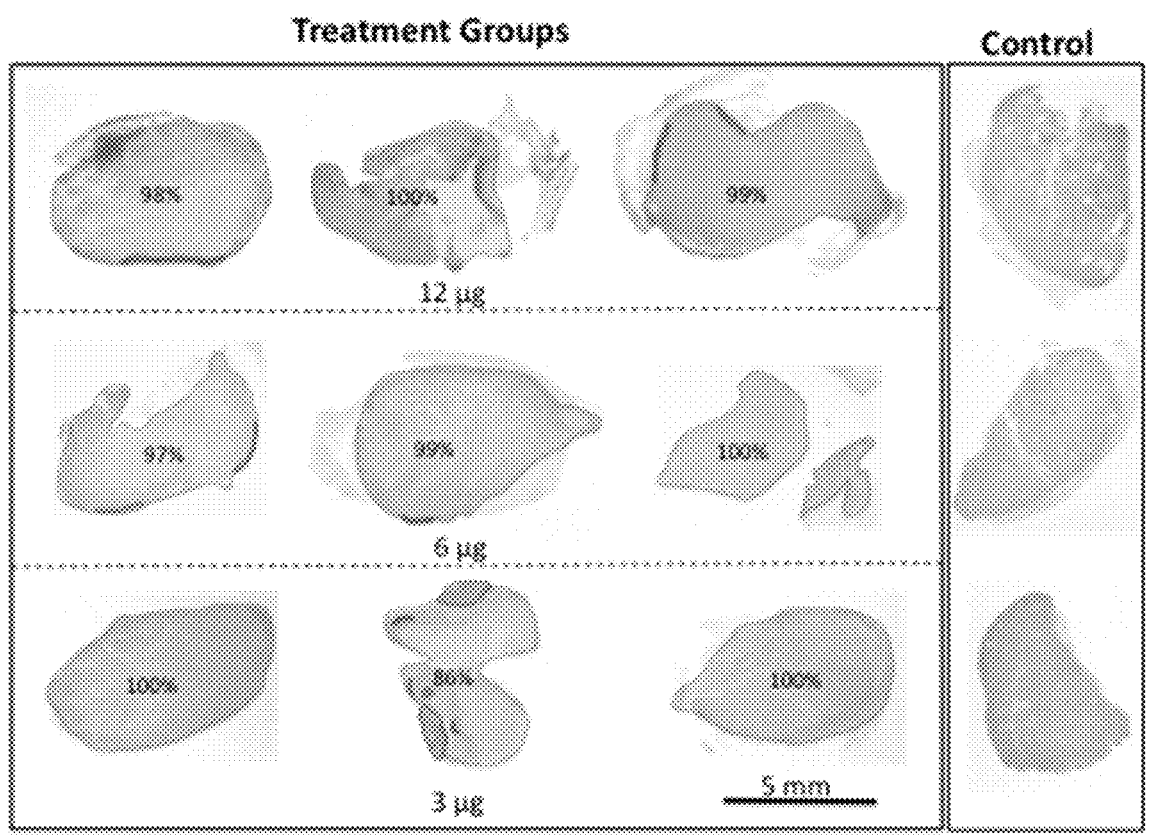
FIG. 11 is a set of micrographs illustrating induction of Hep3B tumor xenograft tumor necrosis by MECA32-Fab-TF (3, 6 and 12 μg) and control MECA32 monoclonal antibody (12 μg). After infusion of MECA32-Fab-TF or MECA32 mAb into tumor feeding artery, tumor xenografts were harvested 72 hours after treatment and submitted for histological sections. The micrographs shown illustrate massive necrosis of tumor (areas highlighted in pink) for all three different doses of MECA32-Fab-TF. The remaining areas of viable tumor tissue are highlighted in blue. All three tumors from the control group were 100% viable as shown at the right column. Areas of necrosis of the treated tumors were calculated by weighing cutouts of whole tumor images and necrotic areas, and were expressed in percentage. Tumor boundaries are outlined with red and blue lines. There were three mice in each treated group.
Figure 12:
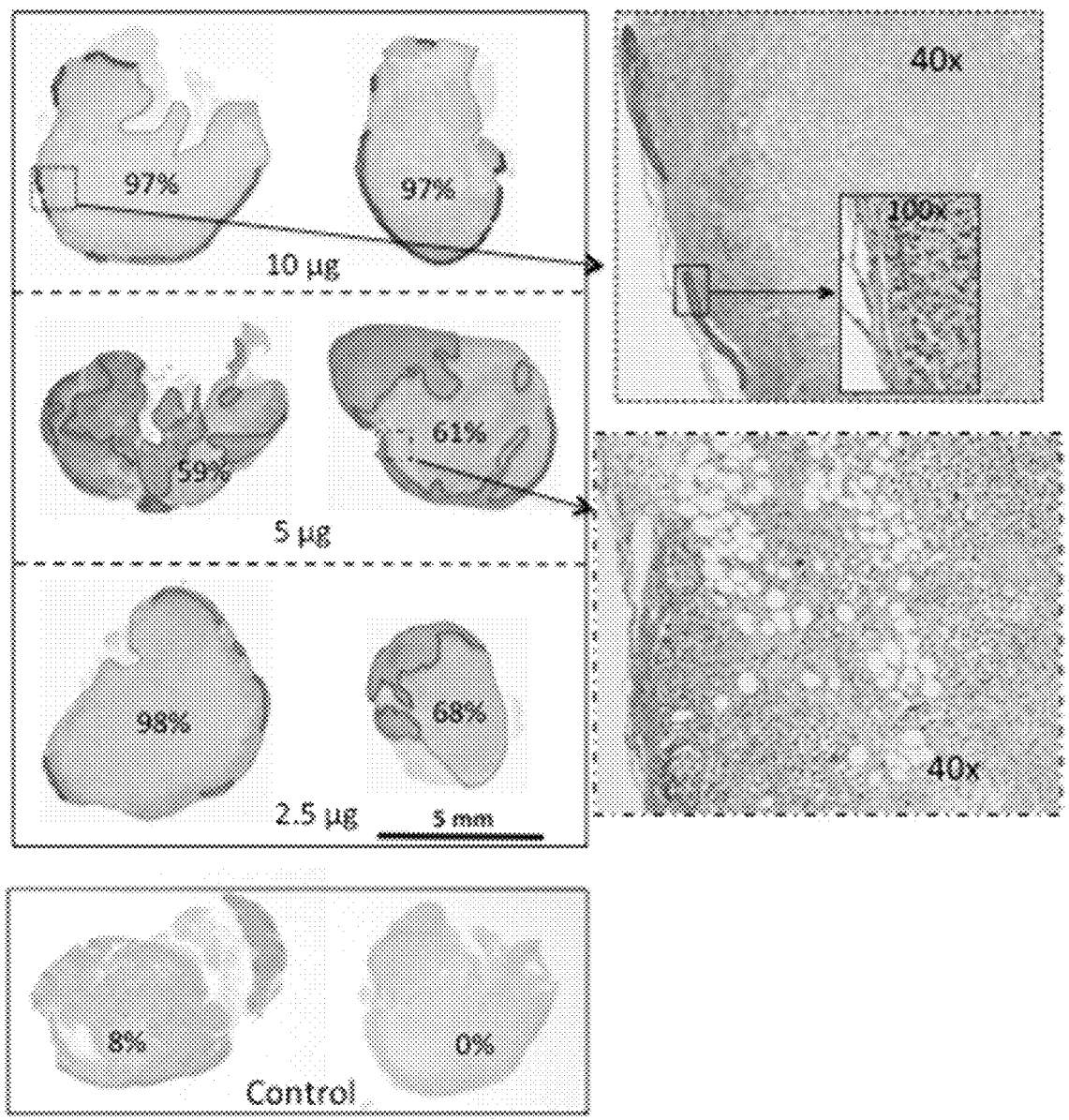
FIG. 12 is a set of micrographs illustrating induction of Hep3B tumor xenograft tumor necrosis by MECA32-Fab-TF (2.5, 5 and 10 μg) and control MECA32 monoclonal antibody (10 μg). This study was similar to that shown in FIG. 11. The main difference was the doses used to treat Hep3B tumor xenografts. Again, tumors were harvested 72 hours after infusion into tumor feeding arteries and submitted for histology sections. There were two mice in each group. Again, the results showed significant tumor necrosis at all three doses after treatment. Necrotic area in each treated tumor highlighted in pink was determined in percentage of whole tumor section as described in FIG. 11. Tumor boundary is outlined with red and blue lines. Areas of square were magnified (40× and 100×) and shown on the right to demonstrate residual viable tumor cells (arrows). Percentage shown in each tumor is the relative necrotic area to total tumor cross section.

To demonstrate the therapeutic efficacy of recombinant MECA32-Fab-TF, we first conducted two dose response studies. For both studies, MECA32-Fab-TF was infused into a tumor feeding femoral artery. Seventy-two hours after treatment, the treated mice were sacrificed and tumors were harvested for histological examination. For the first study, three different doses of MECA32-Fab-TF (3 µg, 6 µg and 12 µg) were used to treat tumor-bearing mice and the control group was treated with 12 µg MECA32 monoclonal antibody without tissue factor. There were three mice for each dose. For the second study, the doses of MECA32-Fab-TF used were 2.5 µg, 5 µg and 10 µg. There were two mice at each dose. The results of these two studies were summarized and shown in FIGS. 11 and 12. The results of these studies revealed that tumors from the mice treated with MECA32-Fab-TF developed massive ischemic necrosis at all doses. However, the dose of 10 µg or higher yielded more consistent results. No or minimal tumor necrosis was noted in the control groups. The results of these studies demonstrated that anti-PLVAP-Fab-TF was quite potent and could induce significant ischemic tumor necrosis as low as 2.5 µg per mouse within 72 hours.

Effect of Anti-mPLVAP MECA32-Fab-TF on Histology of HEP3B Tumor Xenografts at Different Time Points After Infusion The studies described above indicated that tumor developed frank ischemic necrosis 72 hour after treatment. In order to learn how necrosis was induced after treatment with anti-mPLVAP Fab coexpressing TF, we infused MECA32-Fab-TF into tumor feeding artery and harvested HEP3B tumors at 2 hours, 4 hours, 24 hours, 48 hours and 72 hours after infusion after infusion of 10 µg MECA32-Fab-TF. There were two tumor-bearing mice at each time point. Two mice without treatment were also sacrificed on the same day of this experiment as 0 hour base-line controls.

Figure 13A:
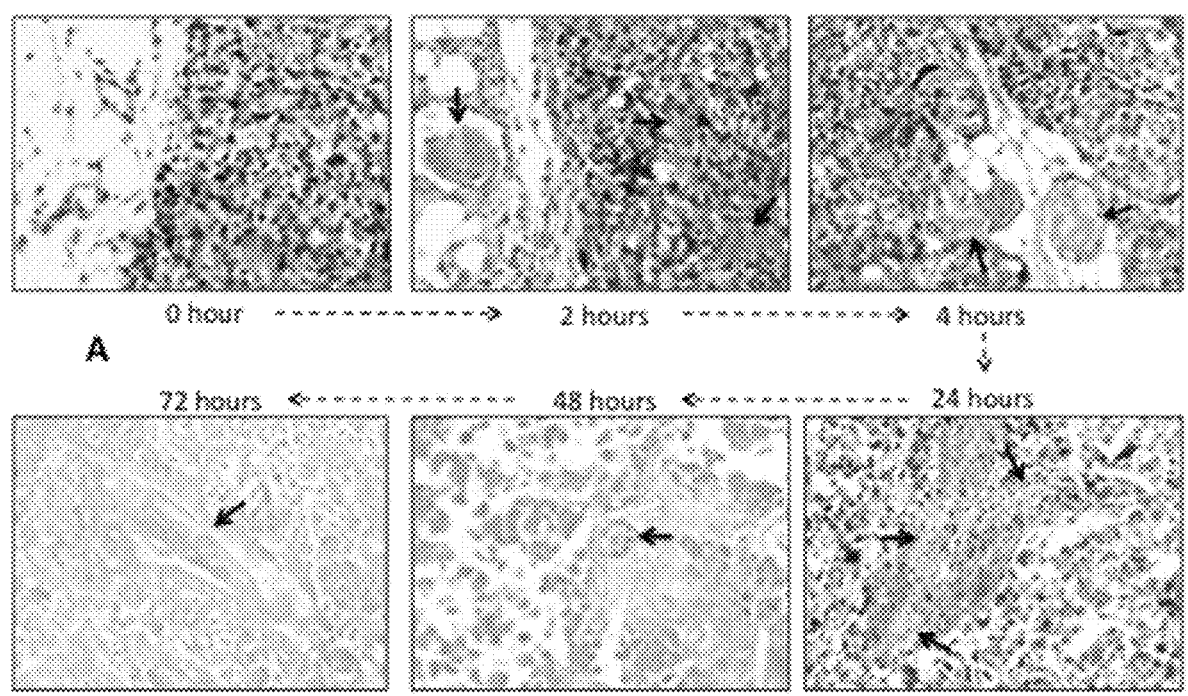
FIGS. 13A and 13B are sets of micrographs illustrating changes of tumor histology at 2, 4, 24, 48 and 72 hours after infusion of 10 μg MECA32-Fab-TF. The sections were stained with hematoxylin and eosin.
Figure 13B:
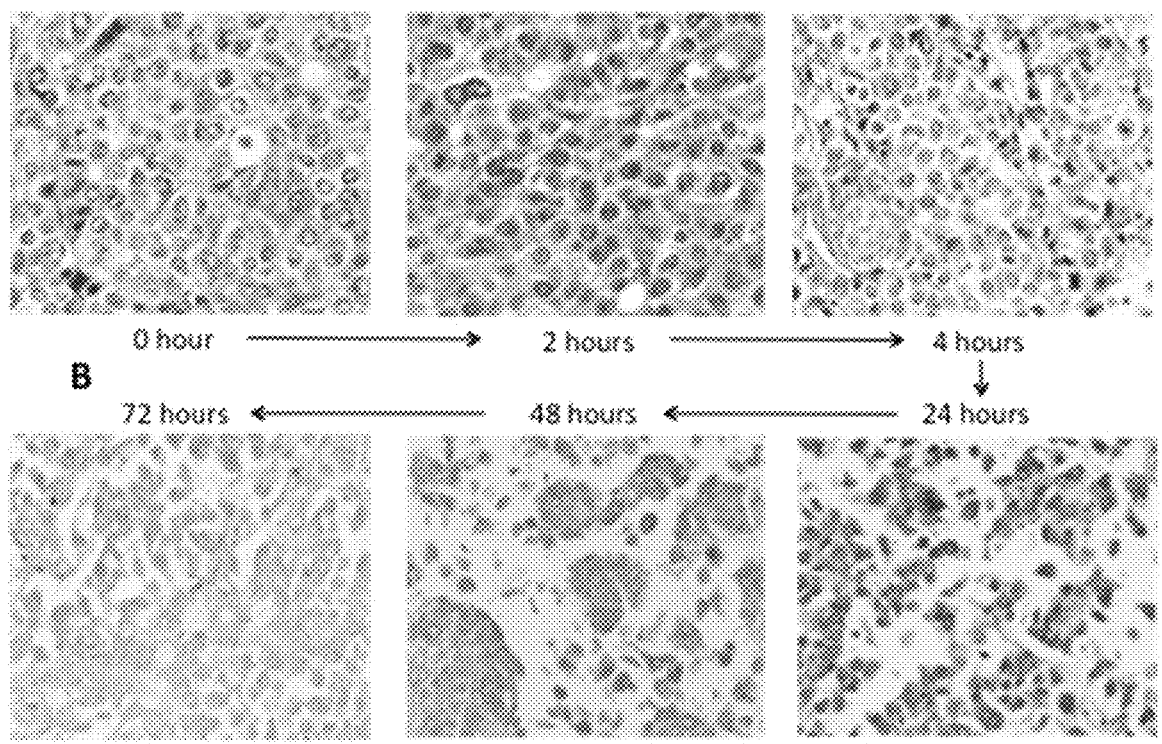
Figure 14:
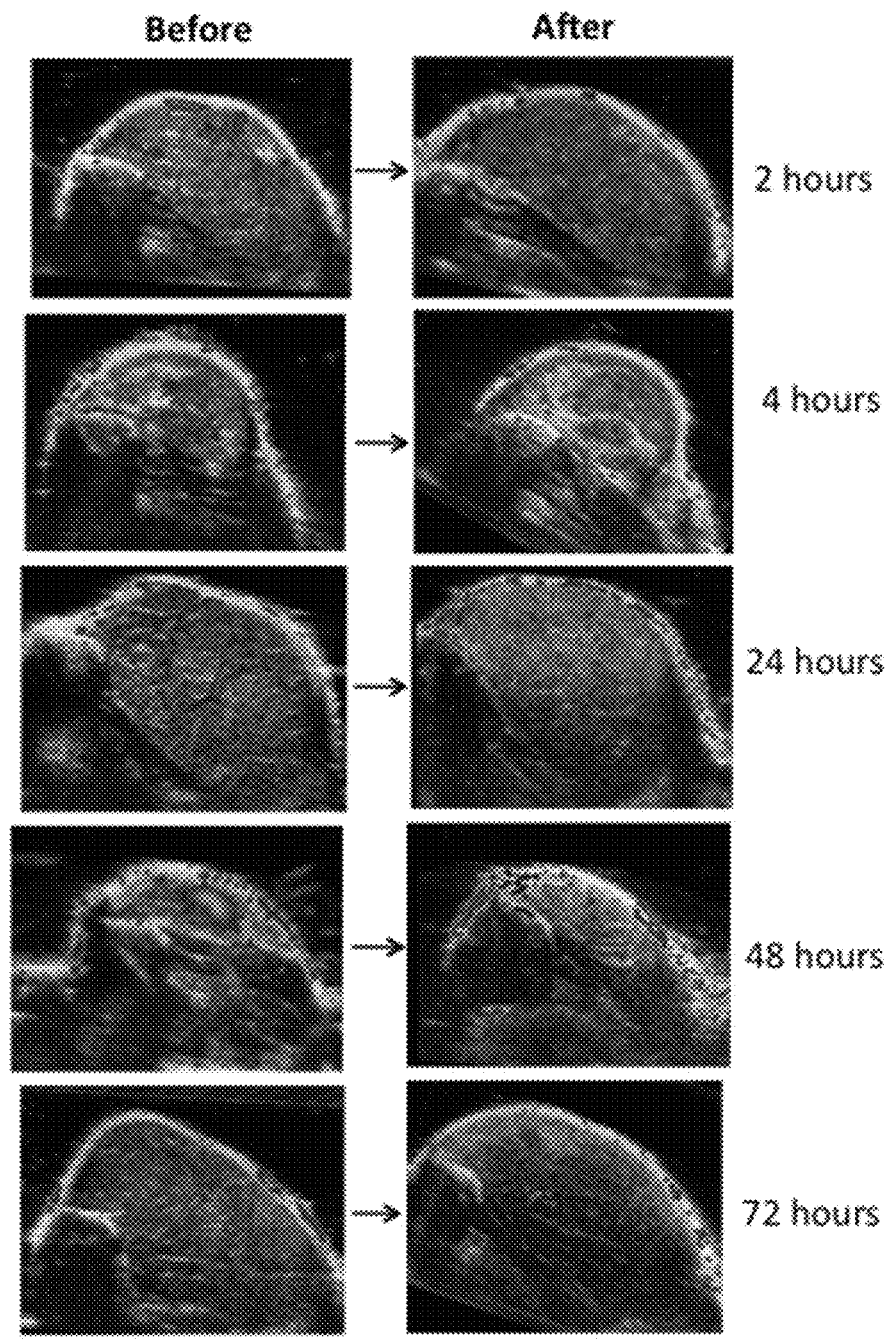
FIG. 14 is a set of photographs of tumor blood flow by sonography, illustrating changes of tumor blood flow at different time points after infusion of 10 μg MECA32-Fab-TF. Tumor blood flow was assessed by 3D power Doppler before and after treatment. There were two mice at each time point. Mice were euthanized immediately after post-treatment 3D power Doppler study. Sonographs with power Doppler signal (red) from one of the two mice at each time point before and after treatment were shown here. Sonographs of tumors collected 48 hours before treatment are shown on the left. After treatments are shown on the right, in which tumor blood flow signals disappeared at 2 hours and persisted up to 72 hours after treatment.

As shown in FIG. 13A, our results revealed that fibrin thrombi in tumor blood vessels could be found at 2 hours after treatment. The number of blood vessels containing fibrin thrombi became more evident at 4 hours and 24 hours after treatment. Tumor cells began to separate from each other with increased clear space at 4 hours and this change became more apparent at 24 hours (FIG. 13B). Frank ischemic necrosis with loss of nuclear staining was noted at 48 hours after treatment and became more pronounced at 72 hours (FIGS. 13A and 13B). No fibrin thrombi were noted in tumor blood vessels before treatment (0 hour) (FIG. 13A). Power Doppler study also revealed cessation of blood flow in major tumor blood vessels at 2 hours after infusion and lasted to 72 hours (FIG. 14). These findings support that anti-PLVAP-Fab-TF indeed could bind to PLVAP of tumor vascular endothelial cells, induced blood clot formation in tumor blood vessels, created blockage of blood flow and caused tumor necrosis.

Effect of Anti-PLVAP MECA32-Fab-TF on Growth of HEP3B Tumor Xenografts

Figure 15:
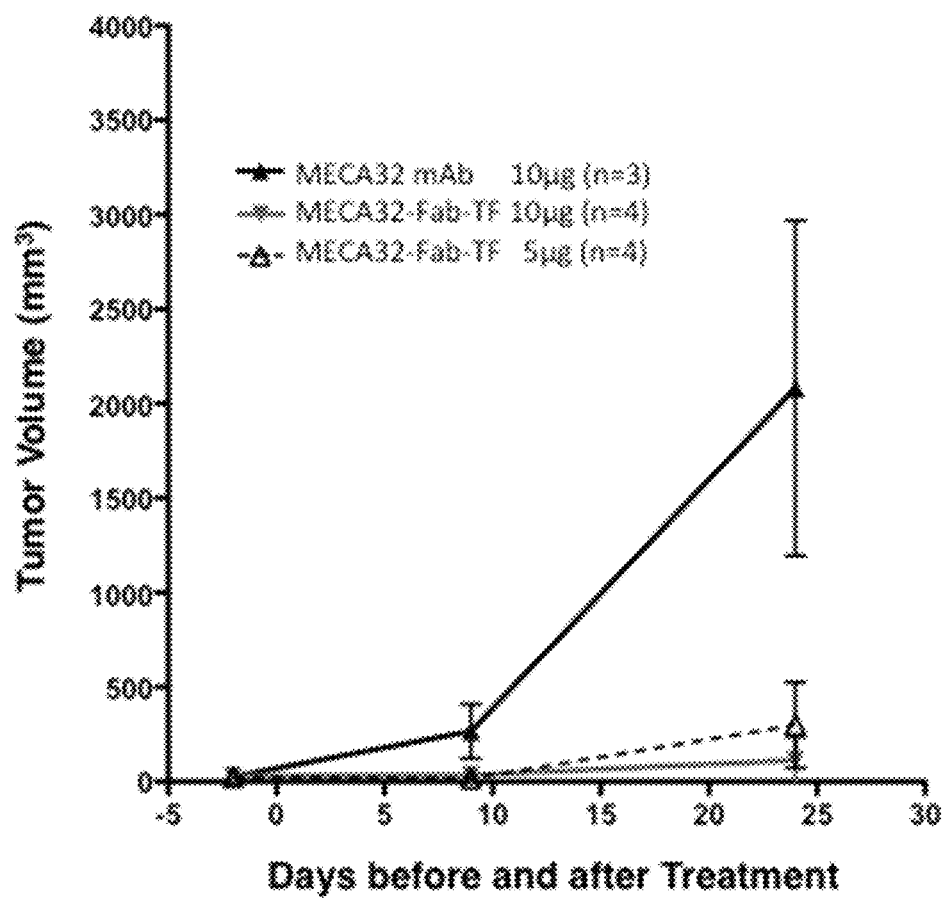
FIG. 15 is a line graph of tumor volume over time, illustrating the effect of intra-arterial infusion of MECA32-Fab-TF on growth of Hep3B tumor xenografts. SCID mice bearing Hep3B human hepatocellular carcinoma xenografts were treated with single infusion of 10 control MECA32 monoclonal antibody (mAb) and 5 or 10 μg MECA32-Fab-TF on day 0. Tumor volumes were measured using 3D sonography −2, 9, and 24 days from treatment on day 0. The average initial tumor volumes measured on day −2 for MECA32 mAb control group and two MECA32-Fab-TF treatment groups (10 and 5 μg) were 26.8, 29.0 and 23.1 mm$^3$, respectively. The tumor volume of each group is expressed as mean ±SD in mm$^3$. The different growth rates of the treatment groups and the control group were compared using linear mixed-effects model. P values were 0.0003 and 0.0001 for comparisons between the 5 μg treatment group and the control group, and the 10 μg treatment group and the control group, respectively.
Figure 16A:
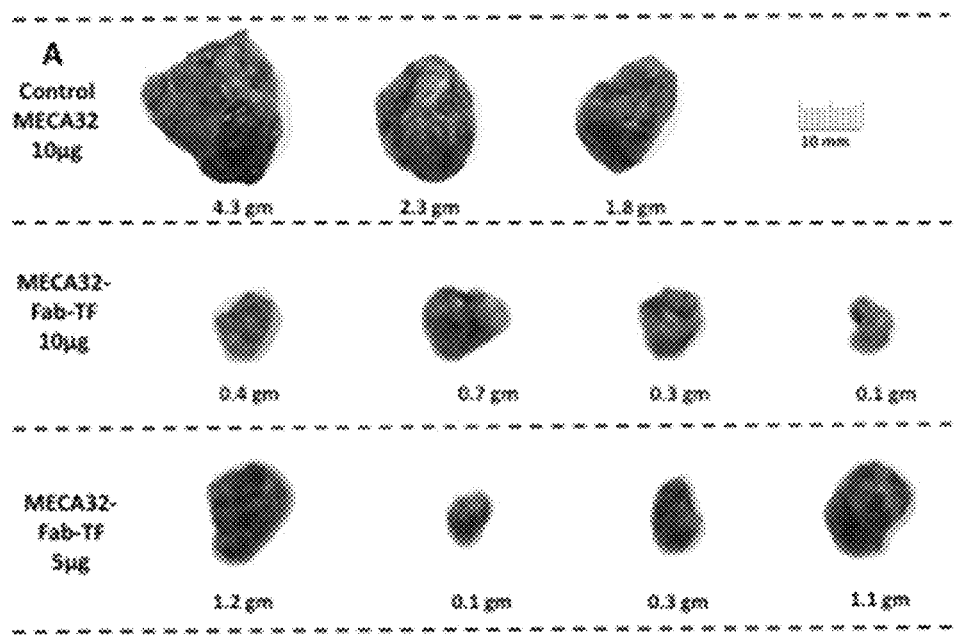
FIG. 16A shows photographs and weights of the excised Hep3B tumors 25 days after initial treatment with MECA32 mAb or MECA32-Fab-TF (panel A). The average tumor weights of each treatment group and the control groups (mean±SEM) are shown in FIG. 16B as bar graphs. Tumor weights of each MECA32-Fab-TF treatment group were compared with those of the control group by t-test. P values were 0.01 and 0.03 for 10 μg and 5 μg MECA32-Fab-TF treatment groups, respectively.
Figure 16B:
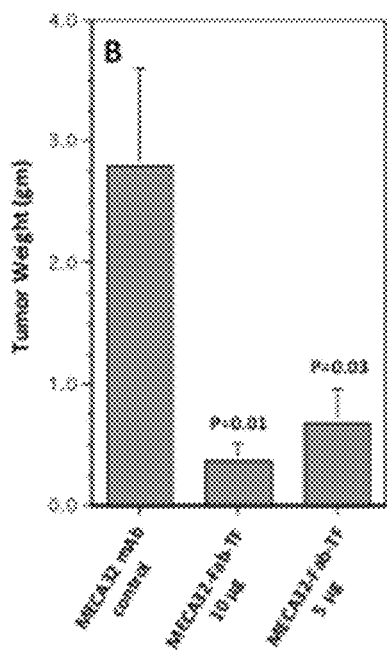

Next, we studied the therapeutic effect of anti-PLVAP Fab-TF treatment on tumor growth. Two different studies were conducted. The first study was to follow tumor growth for 25 days after treatment. The study was terminated 25 days after treatment, because the large sizes of tumors in the control group necessitated the stop of the study. Tumor sizes were followed using 3D-sonography. The results summarized in FIGS. 15, 16A and 16B showed that single infusion of 5 µg or 10 µg of MECA32-Fab-TF effectively suppressed the tumor growth but not by 10 µg control MECA32 antibody without TF.

Figure 17:
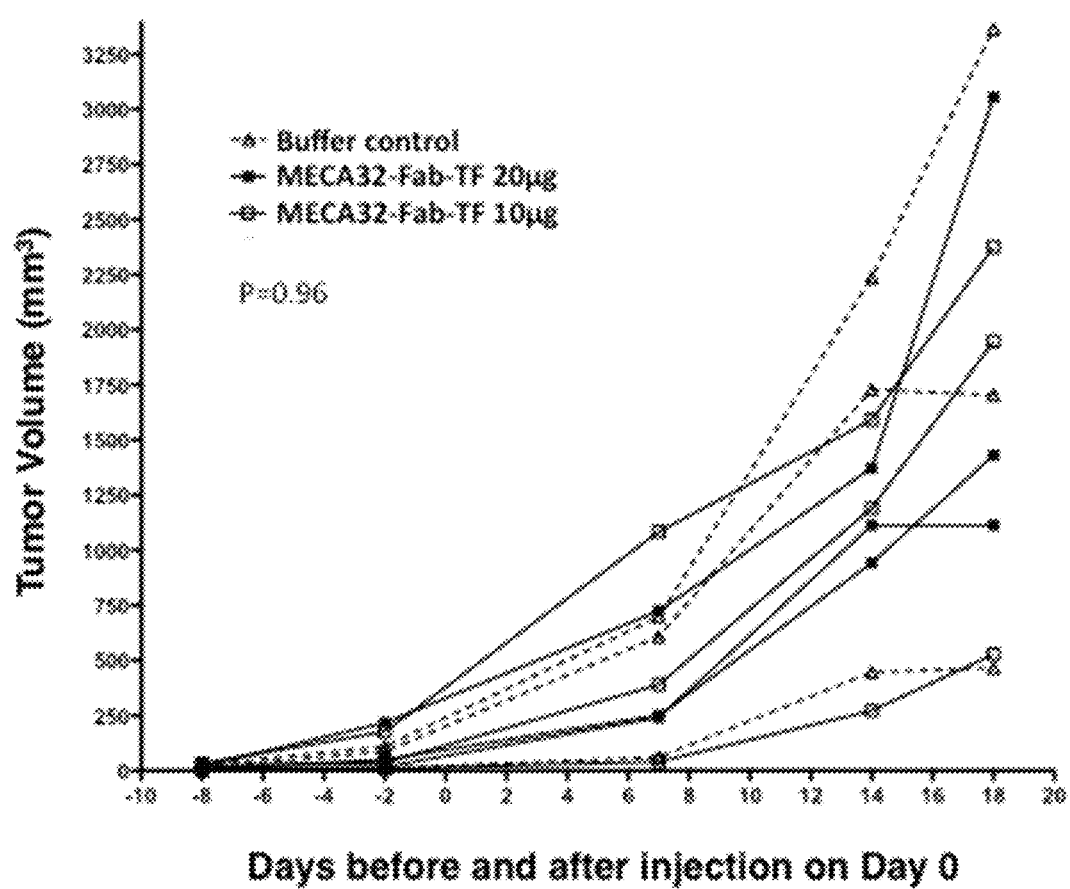
FIG. 17 is a line graph of tumor volume over time, illustrating the effect of systemic administration of MECA-32-Fab-TF on growth of Hep3B tumor xenografts. Mice were treated with systemic administration of MECA32-Fab-TF for treatment or phosphate buffered saline for control through a tail vein. Tumor growth was monitored by measurement of three perpendicular dimensions with a caliper before and after treatment on day 0. The final tumor volumes of all three groups were compared by ANOVA. The result showed no significant difference among all three groups with p value of 0.96. The average tumor volumes (mean±SEM) of these three groups were 1844±840 mm$^3$ (control), 1867±602 mm$^3$ (20 MECA32-Fab-TF) and 1617±559 mm$^3$ (10 μg MECA32-Fab-TF).

For the second study, SCID mice bearing HEP3B tumor xenografts were treated with intra-arterial infusion of 10 µg MECA32-Fab-TF (n=4) or 10 µg MECA32 monoclonal antibody (n=2). Tumor growth was followed with 3D sonography. When HEP3B tumors grew to approximately 2000 cubic millimeter, tumor-bearing mice were euthanized. This study allowed us to assess the delay of tumor growth in the treatment group. The results summarized in FIG. 17 showed that there was a significant delay of tumor growth after single infusion of 10 µg MECA32-Fab-TF into the tumor-feeding artery. It took 42 more days for the tumor in the treatment group to grow to 1600 mm$^3$ comparing to the control mice. The average days for tumors to grow to 1600mm$^3$ between the control and the treatment groups were $9.8\pm3.0$ days and $51.8\pm3.2$ days, respectively (FIG. 17).

In summary, the results of these two different studies further supported that infusion of anti-PLVAP-Fab-TF into tumor feeding artery was effective to induce tumor necrosis and control tumor growth.

Effect of systemic administration of anti-PLVAP-Fab-TF on tumor growth

In order to know whether systemic administration of MECA32-Fab-TF through a peripheral vein can also achieve the same therapeutic effect or not, we injected 10 μg or 20 μg of MECA32-Fab-TF into a tail vein of SCID mouse bearing HEP3B tumor xenograft and monitored tumor growth after injection. Control mice were injected with phosphate buffered saline. There were three mice in each treatment group. The results summarized in FIG. 17 showed that there was no statistically significant effect on tumor volume when MECA32-Fab-TF was administered through a tail vein. Therefore, infusion of anti-PLVAP MECA32-Fab-TF into a tumor feeding artery was necessary to induce tumor necrosis and achieve therapeutic effect. It is possible that systemic administration of MECA32-Fab-TF resulted in dilution of the injected MECA32-Fab-TF and binding of MECA32-Fab-TF to PLVAP on vascular endothelial cells of other organs (e.g., lungs, kidneys and gastrointestinal organs) before reaching to tumor blood vessels.

Development and characterization of anti-human PLVAP Fab-TF

In order to know whether a similar therapeutic agent could be developed against human PLVAP, a humanized anti-human PLVAP monoclonal antibody against an antigenic epitope residing in the amino acid sequence of PPA-GIPVAPSSG (SEQ ID NO: 25) at the carboxyl terminus of human PLVAP was used. This humanized anti-human PLVAP monoclonal antibody was developed previously and is described in U.S. Patent Application Publication No. US20110262349 A1. This anti-human PLVAP-Fab-TF conjugate was designated as CSRO2-Fab-TF (FIG. 9). We then conducted a series of studies to compare CSRO2-Fab-TF with MECA32-Fab-TF in terms of tissue factor specific activity and binding affinity to target PLVAP. The results of our studies showed that anti-human PLVAP CSRO2-Fab-TF appeared to have higher TF activity in each milligram of anti-PLVAP Fab-TF comparing to anti-mouse PLVAP MECA32-Fab-TF and both CSRO2-Fab-TF and MECA32-Fab-TF had similar binding affinities (Table 1). The findings indicated that CSRO2-Fab-TF like MECA32-Fab-TF could bind to their PLVAP targets with sufficient affinity and carried sufficient TF activity to initiate blood coagulation to achieve a therapeutic effect.

TABLE 1

Comparison of tissue factor (TF) specific activity on each milligram of anti-PLVAP Fab-TF and binding affinity to PLVAP between anti-human PLVAP CSRO2-Fab-TF and anti-mouse PLVAP MECA32-Fab-TF.

| | No. of batches | Tissue factor specific activity (μg/mg) mean ± SD | Kd (M) Mean ± SD |
|---|---|---|---|
| CSR02-Fab-TF | 3 | 156 ± 16 | $3.07 ± 1.25 \times 10^{-8}$ |
| MECA32-Fab-TF | 6 | 90 ± 22 | $5.72 ± 1.40 \times 10^{-8}$ |

As summarized in Table 1, three different batches of CSRO2-Fab-TF and six different batches of MECA32-Fab-TF were studied. Results indicated that both Fab-TF had similar binding affinities. Nevertheless, CSRO2-Fab-TF had higher specific TF activity than MECA32-Fab-TF. The results indicate that CSRO2-Fab-TF has sufficient binding affinity and tissue factor specific activity to achieve therapeutic effect like MECA32-Fab-TF for treatment of hepatocellular carcinoma.

Based on the average tumor volume at the time of treatment and the doses of MECA32-Fab-TF required to effectively induce tumor necrosis in our Hep3B xenograft model, we estimated that the effective therapeutic dose for anti-PLVAP-Fab-TF to treat HCC by infusion into tumor feeding artery is between 15 μg to 100 μg for each milliliter (cubic centimeter) of tumor.

Figure 18:
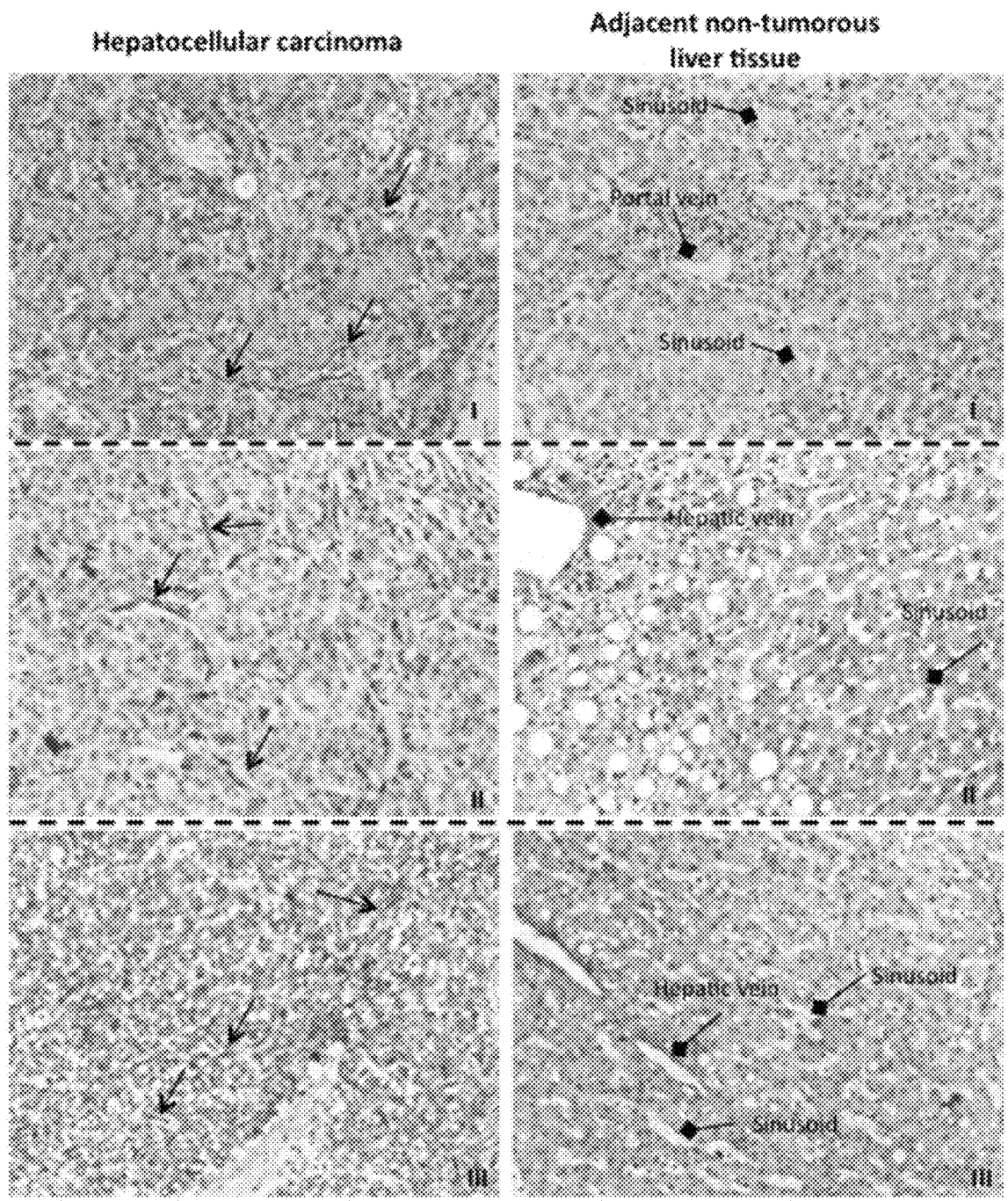
FIG. 18 is a set of micrographs, illustrating immunohistochemical staining of sections from three different cases of human hepatocellular carcinomas (HCC) and adjacent non-tumorous liver tissues with biotinylated CSRO2-Fab-TF. All blood vessels in three HCC sections shown on left column were stained positively (arrows) for PLVAP with brown color precipitate in vascular endothelial cells. In contrast, endothelial cells lining liver sinusoid, portal vein and hepatic veins (diamonds) showed negative staining without detectible PLVAP expression.

To further demonstrate that the developed CSRO2-Fab-TF can bind to vascular endothelial cells of human HCC, we biotinylated CSRO2-Fab-TF and used this Fab-TF to study its binding to vascular endothelial cells of human HCC. The results of our studies showed that biotinylated CSRO2-Fab-TF indeed bound to vascular endothelial cells of HCC and not to vascular endothelial cells of non-tumorous liver tissue (FIG. 18). The results of this study supported that CSRO2-Fab-TF like MECA32-Fab-TF could be used for treatment of HCC in patients through infusion into tumor feeding artery(ies).

Based on the knowledge that PLVAP is differentially expressed in blood vessels of HCC and not in those of non-tumorous liver tissues, we have developed a novel therapeutic agent for treatment of HCC by co-expressing human tissue factor protein on anti-PLVAP monoclonal antibody or its Fab fragment. We showed that both whole antibody and its Fab fragment carrying soluble extracellular domain of human tissue factor indeed could induce tumor necrosis and suppressed tumor growth after single infusion into a tumor feeding artery.

Because chemical conjugation of soluble tissue factor to anti-PLVAP antibody could not reproducibly control the same number of tissue factor cross-linked to each antibody at the same sites, we therefore created a recombinant Fab fragment of anti-PLVAP monoclonal antibody with carboxyl terminus of Fd chain co-expressing extracellular domain of human tissue factor and used this recombinant protein as a therapeutic agent for treatment of HCC. To demonstrate that such a therapeutic agent indeed could be used for treatment of HCC, SCID mice bearing tumor derived from HEP3B human hepatocellular carcinoma cell line were first established and used for the proof-of-concept study. We then developed a mouse version of anti-PLVAP-Fab-TF using MECA32 anti-mouse PLVAP hybridoma. It was necessary to develop a mouse version of anti-PLVAP-Fab-TF, because blood vessels growing into human HCC xenograft are derived from mice and express mouse PLVAP. We expressed human tissue factor on both human and mouse versions of anti-PLVAP Fab-TF, because human tissue factor can activate mouse coagulation factor VII and induce blood coagulation in mice. Our comparative study between CSRO2-Fab-TF and MECA32-Fab-TF confirmed that they both can bind to their PLVAP targets with sufficient affinity and carry sufficient tissue factor activity to trigger blood coagulation and achieve therapeutic effect.

The results of our studies demonstrated that the recombinant anti-PLVAP-Fab-TF developed by us had therapeutic effect for treatment of HCC through triggering blood clot formation in tumor blood vessels, blocking tumor flow and inducing tumor necrosis following infusion of this novel therapeutic agent directly into a tumor feeding artery, but not by systemic intravenous administration through a peripheral vein. The studies described in this application also support that anti-human PLVAP monoclonal antibody or its Fab fragment co-expressing tissue factor protein could be used to treat tumors showing expression of PLVAP restricted to tumor blood vessels, such as glioblastoma.

It should be understood that for all numerical bounds describing some parameter in this application, such as "about," "at least," "less than," and "more than," the description also necessarily encompasses any range bounded by the recited values. Accordingly, for example, the description at least 1, 2, 3, 4, or 5 also describes, inter alia, the ranges 1-2, 1-3, 1-4, 1-5, 2-3, 2-4, 2-5, 3-4, 3-5, and 4-5.

For all patents, applications, or other reference cited herein, such as non-patent literature and reference sequence information, it should be understood that it is incorporated by reference in its entirety for all purposes as well as for the proposition that is recited. Where any conflict exits between a document incorporated by reference and the present application, this application will control. All information associated with reference gene sequences disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures, Homologene entries, et cetera) as well as chemical references (e.g., Pub Chem compound, Pub Chem substance, or Pub Chem Bioassay entries, including the annotations therein, such as structures and assays, et cetera) are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention including the working examples. For example, particular experimental parameters exemplified in the working examples can be adapted for use in the claimed invention piecemeal without departing from the invention. For example, for materials that are disclosed, while specific reference of each various individual and collective combinations and permutation of these compounds may not be explicitly disclosed, each is specifically contemplated and described herein. Thus, if a class of elements A, B, and C are disclosed as well as a class of elements D, E, and F and an example of a combination of elements, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, elements of a composition of matter and steps of method of making or using the compositions.

The foregoing aspects of the invention, as recognized by the person having ordinary skill in the art following the teachings of the specification, can be claimed in any combination or permutation to the extent that they are novel and non-obvious over the prior art—thus to the extent an element is described in one or more references known to the person having ordinary skill in the art, they may be excluded from the claimed invention by, inter alia, a negative proviso or disclaimer of the feature or combination of features.

While this invention has been particularly shown and described with references to example embodiments thereof, it will be understood by those skilled in the art that various changes in form and details may be made therein without departing from the scope of the invention encompassed by the appended claims.

The invention claimed is:

1. A nucleic acid encoding a conjugate comprising a tissue factor (TF) comprising an amino acid sequence having at least 95% sequence identity to SEQ ID NO: 1 conjugated via a linker peptide to an antibody that binds an extracellular domain epitope of human plasmalemma vesicle associated protein (PLVAP), wherein the antibody comprises:
   a complementarity determining regions (CDRs) 1-3 of a heavy chain variable region (HCVR) comprising the amino acid sequence of SEQ ID NO: 3, and CDRs 1-3 of a light chain variable region (LCVR) comprising the amino acid sequence of SEQ ID NO: 4; or
   b) CDRs 1-3 of a HCVR comprising the amino acid sequence of SEQ ID NO: 5, and CDRs 1-3 of a LCVR comprising the amino acid sequence of SEQ ID NO: 6.

2. The nucleic acid of claim 1, wherein the antibody comprises a LCVR comprising the amino acid sequence of SEQ ID NO: 4 and a HCVR comprising the amino acid sequence of SEQ ID NO: 3, or a LCVR comprising the amino acid sequence of SEQ ID NO: 6 and a HCVR comprising the amino acid sequence of SEQ ID NO: 5.

3. The nucleic acid of claim 2, wherein the LCVR, or HCVR, or both, are humanized.

4. The nucleic acid of claim 3, wherein the LCVR and HCVR comprise:
   a) a HCVR sequence selected from SEQ ID NO: 7, 8, 9, 10, and 11; and a LCVR sequence selected from SEQ ID NO: 12, 13, and 14; or
   b) a HCVR sequence selected from SEQ ID NO: 15, 16, 17, 18, and 19; and a LCVR sequence selected from SEQ ID NO: 20, 21, and 22.

5. The nucleic acid of claim 1, wherein the tissue factor (TF) comprises the amino acid sequence of SEQ ID NO: 1.

6. The nucleic acid of claim 1, wherein the conjugate comprises an amino acid sequence identical to SEQ ID NO: 23.

7. The nucleic acid of claim 4, wherein the HCVR sequence comprises SEQ ID NO: 11 and the LCVR sequence comprises SEQ ID NO: 13; or the HCVR sequence comprises SEQ ID NO: 19 and the LCVR sequence comprises SEQ ID NO: 22.

8. A vector comprising the nucleic acid of claim 1.

9. A host cell comprising the nucleic acid of claim 1.

10. The host cell of claim 9, wherein the nucleic acid is included in a vector.

11. The host cell of claim 9, wherein the host cell is a bacterial cell.

12. The host cell of claim 11, wherein the bacterial cell is *Escherichia coli*.

13. The host cell of claim 9, wherein the host cell is a eukaryotic cell selected from a fungus, an insect cell, and a mammalian cell.

14. The host cell of claim 13, wherein the fungus is yeast.

15. The host cell of claim 13, wherein the insect cell is any one or more of Sf0 cell or Sf21 cell.

16. The host cell of claim 13, wherein the mammalian cell is any one or more of CHO cell, VERO cell, or COS cell.

17. A method of making a conjugate comprising a coagulating agent conjugated to an antibody that binds an extracellular domain epitope of human PLVAP, comprising culturing the host cell of claim 9 under conditions that support the expression of the conjugate by the host cell, and isolating the expressed conjugate.

18. The nucleic acid of claim 1, wherein the linker peptide comprises a sequence (Gly$_4$-Ser (SEQ ID NO: 49))$_n$, wherein n is 3, 4, 5, or 6.

19. The nucleic acid of claim 18, wherein the linker peptide comprises the sequence (Gly$_4$-Ser (SEQ ID NO: 49))$_n$

UNITED STATES PATENT AND TRADEMARK OFFICE
CERTIFICATE OF CORRECTION

| | |
|---|---|
| PATENT NO. | : 12,371,473 B2 |
| APPLICATION NO. | : 17/813857 |
| DATED | : July 29, 2025 |
| INVENTOR(S) | : Kuo-Jang Kao and Yun-Hsin Wang |

Page 1 of 1

It is certified that error appears in the above-identified patent and that said Letters Patent is hereby corrected as shown below:

In the Claims

In Claim 1, Column 45, Line 26, delete "a complementarity" and insert --a) complementarity--

Signed and Sealed this
Sixteenth Day of September, 2025

Coke Morgan Stewart
*Acting Director of the United States Patent and Trademark Office*